US007208576B2

(12) United States Patent
Mulroy et al.

(10) Patent No.: US 7,208,576 B2
(45) Date of Patent: Apr. 24, 2007

(54) NON-GLYCOSYLATED HUMAN ALPHA-FETOPROTEIN, METHODS OF PRODUCTION, AND USES THEREOF

(75) Inventors: Robert Mulroy, Cambridge, MA (US); Ian Krane, Westboro, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 541 days.

(21) Appl. No.: 10/624,380

(22) Filed: Jul. 22, 2003

(65) Prior Publication Data

US 2004/0098755 A1 May 20, 2004

(51) Int. Cl.
*C07K 14/47* (2006.01)
(52) U.S. Cl. ..................................... 530/350
(58) Field of Classification Search ...................... None
See application file for complete search history.

(56) References Cited

U.S. PATENT DOCUMENTS

| | | | | |
|---|---|---|---|---|
| 4,692,332 | A | 9/1987 | McMichael | 424/88 |
| 4,873,316 | A | 10/1989 | Meade et al. | 800/7 |
| 4,877,610 | A | 10/1989 | McMichael | 424/88 |
| 4,966,753 | A | 10/1990 | McMichael | 424/88 |
| 4,970,071 | A | 11/1990 | McMichael | 424/88 |
| 5,130,415 | A | 7/1992 | Tecce et al. | 530/324 |
| 5,206,153 | A | 4/1993 | Tamaoki et al. | 435/69.7 |
| 5,302,698 | A | 4/1994 | Morinaga et al. | 530/350 |
| 5,322,775 | A | 6/1994 | Clark et al. | 435/69.1 |
| 5,384,250 | A | 1/1995 | Murgita | 435/69.6 |
| 5,589,604 | A | 12/1996 | Drohan et al. | 800/7 |
| 5,633,076 | A | 5/1997 | DeBoer et al. | 800/25 |
| 5,639,940 | A | 6/1997 | Garner et al. | 800/7 |
| 5,648,243 | A | 7/1997 | Hurwitz et al. | 435/69.6 |
| 5,652,352 | A * | 7/1997 | Lichenstein et al. | 536/23.5 |
| 5,723,585 | A | 3/1998 | Baker et al. | 530/413 |
| 5,766,884 | A | 6/1998 | Townes et al. | 800/5 |
| 5,827,690 | A | 10/1998 | Meade et al. | 800/7 |
| 5,831,141 | A | 11/1998 | Lubon et al. | 800/7 |
| 5,843,705 | A | 12/1998 | Ditullio et al. | 800/7 |
| 5,843,776 | A | 12/1998 | Tamaoki et al. | 435/325 |
| 5,965,528 | A | 10/1999 | Murgita | 514/12 |
| 6,013,857 | A | 1/2000 | Deboer et al. | 800/15 |
| 6,288,034 | B1 | 9/2001 | Murgita | 514/12 |
| 6,331,611 | B1 | 12/2001 | Murgita | 530/350 |
| 2003/0143237 | A1 * | 7/2003 | Economou et al. | 424/185.1 |

FOREIGN PATENT DOCUMENTS

| | | |
|---|---|---|
| EP | 0 001 812 | 5/1979 |
| EP | 0 487 229 | 9/1997 |
| JP | 2005866 | 1/1990 |
| WO | WO 86/04241 | 7/1986 |
| WO | WO 93/05774 | 4/1993 |
| WO | WO 94/10199 | 5/1994 |
| WO | WO 95/00637 | 1/1995 |
| WO | WO 96/09377 | 3/1996 |
| WO | WO 96/22787 | 8/1996 |
| WO | WO 00/40693 | 7/2000 |
| WO | WO 01/15709 | 3/2001 |

OTHER PUBLICATIONS

Semeiuk et al. Evidence that Immunosuppression is an Intrinsic Property of the Alpha-Fetoprotein Molecule. Immunology or Proteins and Peptides VIII, M.Z. Atassie et al, eds. Plenum Press, New York, 1995, pp. 255-269.*
Pucci et al., "Human alpha-Fetoprotein Primary Structure: A Mass Spectrometric Study," *Biochemistry* 1991, 30, 5061-5066.*
Abramsky et al., "A Role of Alpha-Fetoprotein in Autoimmune Diseases," *Annals New York Academy of Sciences* 417:108-116 (1983).
Abramsky et al., "Alpha-Fetoprotein Suppresses Experimental Allergic Encephalomyelitis," *Journal of Neuroimmunology* 2:1-7 (1982).
Aoyagi et al., "Differential Reactivity of Alpha-Fetoprotein with Lectins and Evaluation of its Usefulness in the Diagnosis of Hepatocellular Carcinoma," *Gann* 75:809-815 (1984).
Bennett et al., "Similarity Between Natural and Recombinant Human Aplha-Fetoprotein as Inhibitors of Estrogen-Dependent Breast Cancer Growth," *Breast Cancer Research and Treatment* 45:169-179 (1997).
Biddle et al., "Specific Cytoplasmic Alpha-Fetoprotein Binding Protein in MCF-7 Human Breast Cancer Cells and Primary Breast Cancer Tissue," *Breast Cancer Research and Treatment* 10:279-286 (1987).
Birrer et al., "The Immunology of Alphafetoprotein," *Journal of Tumor Marker Oncology* 14:55-62 (1999).
Boismenu et al., "Expression of Domains of Mouse Alpha-Fetoprotein in *Escherichia coli*," *Life Sciences* 43:673-681 (1988).
Brenner et al., "Immunosuppression of Experimental Autoimmune Myasthenia Gravis by Alpha-Fetoprotein Rich Formation," *Immunology Letters* 3:163-167 (1981).
Brenner et al., "Influence of Alpha-Fetoprotein on the *in Vitro* and *in Vivo* Immune Response to Acetylcholine Receptor," *Annals New York Academy of Sciences* 377:208-221 (1981).
Brenner et al., "Inhibitory Effect of Alpha-Fetoprotein on the Binding of Myasthenia Gravis Antibody to Acetylcholine Receptor," *Proc. Natl. Acad. Sci. USA* 77:3635-3639 (1980).
Buamah et al., "Serum Alpha-Fetoprotein Heterogeneity as a Means of Differentiating Between Primary Hepatocellular Carcinoma and Hepatic Secondaries," *Clinica. Chimica. Acta.* 139:313-316 (1984).
Buschman et al., "Experimental Myasthenia Gravis Induced in Mice by Passive Transfer of Human Myasthenic Immunoglobulin," *Journal of Neuroimmunology* 13:315-330 (1987).
Caturla et al., "The Thyroid Hormone Down-Regulates the Mouse Alpha-Foetoprotein Promoter," *Molec. and Cell. Endocrin.* 135:139-145 (1997).
Cohen et al., "Suppression by Alpha-Fetoprotein of Murine Natural Killer Cell Activity Stimulated *in Vitro* and *in Vivo* by Interferon and Interleukin 2," *Scand. J. Immunol.* 23:211-223 (1986).
Dattwyler et al., "Binding of Alpha-Foetoprotein to Murine T Cells," *Nature* 256:656-657 (1975).

(Continued)

Primary Examiner—Robert A. Wax
(74) Attorney, Agent, or Firm—Clark & Elbing, LLP; Paul T. Clark

(57) ABSTRACT

The invention features non-glycosylated human alpha-fetoprotein, methods of production, and uses thereof.

3 Claims, 8 Drawing Sheets

OTHER PUBLICATIONS

Dudich et al., "Growth-Regulative Activity of Human Alpha-Fetoprotein for Different Types of Tumor and Normal Cells," *Tumor Biology* 19:30-40 (1998).

Galarneau et al., "The Alpha$_1$-Fetoprotein Locus is Activated by a Nuclear Receptor of the *Drosophila* FTZ-F1 Family," *Molec. and Cell. Biol.* 16:3853-3865 (1996).

Gershwin et al., "The Influence of Alpha-Fetoprotein on Moloney Sarcoma Virus Oncogenesis: Evidence for Generation of Antigen Nonspecific Suppressor T Cells," *The Journal of Immunology* 121:2292-2297 (1978).

Gibbs et al., "Structure, Polymorphism, and Novel Repeated DNA Elements Revealed by a Complete Sequence of the Human Alpha-Fetoprotein Gene," *Biochemistry* 26:1332-1343 (1987).

Giuliani et al., "Synthesis and Characterization of a Recombinant Fragment of Human Alpha-Fetoprotein with Antigenic Selectivity Versus Albumin," *Protein Engineering* 2:605-610 (1989).

Glazier et al., "Graft-Versus-Host Disease in Cyclosporin A-Treated Rats After Syngeneic and Autologous Bone Marrow Reconstitution," *J. Exp. Med.* 158:1-8 (1983).

Goidl et al., "Studies on the Mechanisms of Alpha-Fetoprotein Induction of Immune Suppressive Activity," from *Developmental Immunobiology, Proceedings of the Fifth Irwin Strasburger Memorial Seminar on Immunology* eds. Siskind et al., 35-55 (1979).

Hamel et al., "Phenotype and Function of Bone-Marrow-Derived T- and Non-T-Cells Activated *in Vitro* by Alpha-Fetoprotein," *Biological Activities of Alpha$_1$-Fetoprotein* eds. Mizejewski et al. 1:167-177 (1987).

Heyward et al., "Early Detection of Primary Hepatocellular Carcinoma by Screening for Alpha-Fetoprotein in High-Risk Families," *The Lancet* 2:1161-1162 (1983).

Hooper et al., "Human AFP Inhibits Cell Proliferation and NK-Like Cytotoxic Activity Generated in Autologous, but not in Allogeneic Mixed Lymphocyte Reactions," *Biological Activities of Alpha$_1$-Fetoprotein* eds. Mizejewski et al. 2:183-197 (1989).

Hooper et al., "Regulation of Murine T-Cell Responses to Autologous Antigens by Alpha-Fetoprotein," *Cellular Immunology* 63:417-425 (1981).

Hooper et al., "Selective Inhibition of Murine T-Cell Proliferation and Lymphokine-Activated Natural Killer Cell Function by Alpha-Fetoprotein," *Biological Activities of Alpha$_1$-Fetoprotein* eds. Mizejewski et al. 1:153-165 (1987).

Hooper et al., "Suppression of Primary and Secondary Autologous Mixed Lymphocyte Reactions by Murine Alphafetoprotein," *Oncodevelopmental Biology and Medicine* 3:151-160 (1982).

Hoskin et al., "Analysis of Pregnancy-Associated Immunoregulatory Pathways," *Alpha-Fetoprotein and Congenital Disorders* 59-78 (1985).

Hoskin et al., "*In Vitro* Activation of Bone Marrow-Derived T-and Non-T-Cell Subsets by Alpha-Fetoprotein," *Cellular Immunology* 96:163-174 (1985).

Hoskin et al., "Specific Maternal Anti-Fetal Lymphoproliferative Responses and Their Regulation by Natural Immunosuppressive Factors," *Clin. Exp. Immunol.* 76:262-267 (1989).

Innis et al., "Amplification of Alpha-Fetoprotein Complementary DNA by Insertion into a Bacterial Plasmid," *Archives of Biochemistry and Biophysics* 195:128-135 (1979).

Ishiguro et al., "Serum Alpha-Fetoprotein Subfractions in Patients with Primary Hepatoma or Hepatic Metastasis of Gastric Cancer," *Cancer* 55:156-159 (1985).

Jacobson et al., "Inhibition of Estrogen-Dependent Breast Cancer Growth by a Reaction Product of Alpha-Fetoprotein and Estradiol," *Cancer Research* 50:415-420 (1990).

Jiang et al., "Role of CD8+ T Cells in Murine Experimental Allergic Encephalomyelitis," *Science* 256:1213-1215 (1992).

Keller et al., "Immunosuppressive Properties of AFP: Role of Estrogens," from *Onco-Developmental Gene Expression* eds. Fishman et al. 287-295 (1976).

Kerr et al., "The Bladder as a Bioreactor: Urothelium Production and Secretion of Growth Hormone into Urine," *Nat. Biotechnol.* 16:75-79 (1998).

Kikutani et al., "The Murine Autoimmune Diabetes Model: NOD and Related Strains," *Advances in Immunology* 51:285-322 (1992).

Koyama et al., "Lectin Affinity Electrophoretic Demonstration of Tissue Specificity and Malignant Alteration of Human α-Fetoprotein Isoforms Produced in Transgenic Mice," *Biochemical and Biophysical Research Communications* 223:757-761 (1996).

Line et al., "Medical Potential of AFP as a Tumor Imaging Agent," *Biological Activities of Alpha-Fetoprotein* eds. Mizejewski et al. 2:139-148 (1989).

Lu et al., "Alpha-Fetoprotein Inhibits Macrophage Expression of Ia Antigens," *The Journal of Immunology* 132:1722-1727 (1984).

Masuda et al., "Selective Antitumor Effect of Thioether-Linked Immunotoxins Composed of Gelonin and Monoclonal Antibody to Alpha-Fetoprotein or its F(ab')$_2$ Fragment," *Tumor Biol.* 15:175-183 (1994).

Mizejewski, "Alpha-Fetoprotein Testing: Regulatory and Technical Considerations," *Laboratory Management* (1987).

Morinaga et al., "Primary Structures of Human Alpha-Fetoprotein and its mRNA," *Proc. Natl. Acad. Sci. USA* 80:4604-4608 (1983).

Moro et al., "Monoclonal Antibodies Directed Against a Widespread Oncofetal Antigen: The Alpha-Fetoprotein Receptor," *Tumor Biol.* 14:116-130 (1993).

Murgita et al., "Adult Murine T Cells Activated *in Vitro* by Alpha-Fetoprotein and Naturally Occurring T Cells in Newborn Mice: Identity in Function and Cell Structure Differentiation Antigens," *Proc. Natl. Acad. Sci. USA* 75:2897-2901 (1978).

Murgita et al., "Alpha-Fetoprotein Induces Suppressor T Cells *in Vitro*," *Nature* 267:257-259 (1977).

Murgita et al., "Characterization of Murine Newborn Inhibitory T Lymphocytes: Functional and Phenotypic Comparison with an Adult T Cell Subset Activated *in Vitro* by Alpha-Fetoprotein," *Eur. J. Immunol.* 11:957-964 (1981).

Murgita et al., "Effects of Human Alpha-Foetoprotein on Human B and T Lymphocyte Proliferation *in Vitro*," *Clin. Exp. Immunol.* 33:347-356 (1978).

Murgita et al., "The Effects of Mouse Alpha-Fetoprotein on T-Cell-Dependent and T-Cell-Independent Immune Responses *in Vitro*," *Scand. J. Immunol.* 5:1215-1220 (1976).

Murgita, "The Immunosuppressive Role of Alpha-Fetoprotein During Pregnancy," *Scand. J. Immunol.* 5:1003-1014 (1976).

Murgita et al., "Regulation of Immune Functions in the Fetus and Newborn," *Prog. Allergy* 29:54-133 (1981).

Murgita et al., "Selective Immunoregulatory Properties of Alpha-Fetoprotein," *La Ricerca Clin. Lab.* 9:327-342 (1979).

Murgita et al., "Suppression of the Immune Response by Alpha-Fetoprotein I. The Effect of Mouse Alpha-Fetoprotein on the Primary and Secondary Antibody Response," *The Journal of Experimental Medicine* 141:269-286 (1975).

Murgita et al., "Suppression of the Immune Response by Alpha-Fetoprotein II. The Effect of Mouse Alpha-Fetoprotein on Mixed Lymphocyte Reactivity and Mitogen-Induced Lymphocyte Transformation," *The Journal of Experimental Medicine* 141:440-452 (1975).

Nelson et al., "Maternal-Fetal Disparity in HLA Class II Alloantigens and the Pregnancy-Induced Amelioration of Rheumatoid Arthritis," *The New England Journal of Medicine* 329:466-471 (1993).

Nishi et al., "Expression of Rat Alpha-Fetoprotein cDNA in *Escherichia coli* and in Yeast," *J. Biochem.* 104:968-972 (1988).

O'Neill et al., "Regulation of Human Lymphocyte Activation by Alpha-Fetoprotein: Evidence for Selective Suppression of Ia-Associated T-Cell Proliferation *in Vitro*," *Oncodevelopmental Biology and Medicine* 3:135-150 (1982).

Peck et al., "Cellular and Genetic Restrictions in the Immunoregulatory Activity of Alpha-Fetoprotein I. Selective Inhibition of Anti-Ia-Associated Proliferative Reactions," *J. Exp. Med.* 147:667-683 (1978).

Peck et al., "Cellular and Genetic Restrictions in the Immunoregulatory Activity of Alpha-Fetoprotein II. Alpha-Fetoprotein-Induced Suppression of Cytotoxic T Lymphocyte Development," *J. Exp. Med.* 148:360-372 (1978).

Peck et al., "Cellular and Genetic Restrictions in the Immunoregulatory Activity of Alpha-Fetoprotein III. Role of the MLC-Stimulating Cell Population in Alpha-Fetoprotein-Induced Suppression of T Cell-Mediated Cytotoxicity," *J. of Immunology* 128:1134-1140 (1982).

Sambrook et al., "Expression of Cloned Genes in *Escherichia coli*," *Molecular Cloning* 17:1-44 (1989).

Sell, "Alphafetoprotein," *Cancer Markers Diagnostic and Developmental Significance* 249-293 (1980).

Semeniuk et al., "Immunoregulation by Recombinant Alpha-Fetoproteins Produced in Eukaryotic and Prokaryotic Expression Systems," Abstract 2799, *Experimental Biology 94™* (1994).

Soto et al., "Control of Growth of Estrogen-Sensitive Cells: Role for Alpha-Fetoprotein," *Proc. Natl. Acad. Sci. USA* 77:2084-2087 (1980).

Van Oers, et al., "Isolation and Characterization of a Distinct Immunoregulatory Isoform of Alpha-Fetoprotein Produced by the Normal Fetus," *J. Exp. Med.* 170:811-825 (1989).

Van Oers et al., "Analytical- and Preparative-Scale Separation of Molecular Variants of Alpha-Fetoprotein by Anion-Exchange Chromatography on Monobead™ Resins," *Journal of Chromatography* 525:59-69 (1990).

Villacampa et al, "Alpha-Fetoprotein Receptors in a Human Breast Cancer Cell Line," *Biochemical and Biophysical Research Communications* 122:1322-1327 (1984).

Yamamoto et al., "Expression of Human Alpha-Fetoprotein in Yeast," *Life Sciences* 46:1679-1686 (1990).

Database EMBL, "Expression of Human Alpha-Fetoprotein in Mammalian Cells," retrieved from EBI accession No. EM_PAT: BD267648, Aug. 13, 2003.

Database EMBL, "Human mRNA Encoding Alpha-Fetoprotein (AFP). AFP is a Major Serum Protein (MG: 70000) Synthesized During Fetal Life," retrieved from EBI accession No. V01514, Dec. 6, 1983 (abstract).

Database UniProt, "Alpha-Fetoprotein (AFP)," retrieved from UniProt accession No. Feta-Protein, database accession No. p02771, Jul. 21, 1986 (abstract).

Mizejeweski, Gerald J., "Alpha-Fetoprotein Structure and Function: Relevance to Isoforms, Epitopes, and Conformational Variants," *Experimental Biology and Medicine* 226: 377-408, 2001.

Morinaga et al., "Primary Structures of Human Alpha-Fetoprotein and its mRNA," *Proc. Natl. Acad. Sci. USA* 80: 4604-4608, 1983.

* cited by examiner

NON-GLYCOSYLATED HUMAN ALPHA-FETOPROTEIN, METHODS OF PRODUCTION, AND USES THEREOF

BACKGROUND OF THE INVENTION

This invention relates to non-glycosylated human alpha-fetoprotein, its production in transgenic animals and plants, and uses thereof.

Alpha-fetoprotein (AFP) is a 70 kDa glycoprotein produced by the yolk sac and fetal liver. AFP is present in fetal serum at milligram levels, and, at birth, declines to the nanogram levels normally found in adult serum: increased levels of AFP in adult serum are indicative of a yolk sac tumor, a hepatoma, or of liver regeneration. The role of AFP during fetal development is not known, although it has been suggested that AFP protects a gestating fetus from a maternal immune attack or from the effects of maternal estrogen.

In vitro and in vivo experiments have shown that AFP has both cell growth-stimulatory and -inhibitory activities, depending upon the target cell, the relative concentration of AFP, and the presence of other cytokines and growth factors. For example, AFP can inhibit the growth of many types of tumor cells, and, in particular, inhibits estrogen-stimulated cell growth. Conversely, AFP stimulates the growth of normal embryonal fibroblasts. AFP has also been shown to have both immunosuppressive and immunoproliferative effects.

In order to exploit the various biological properties of AFP, it will be necessary to obtain sufficient quantities of this molecule in an efficient and cost-effective manner. Expression of AFP in recombinant systems has proven difficult because expression of wild-type AFP in eukaryotic cells generally results in the production of several isoforms due to differential glycosylation of AFP at a single asparagine residue (amino acid 233). Expression of AFP in prokaryotic systems typically produces misfolded and inactive protein that is aggregated and does not have the correct internal disulfide bonds. This misfolded AFP must be purified and refolded under conditions that allow for the formation of 16 disulfide bonds, a difficult and time-consuming process, which results in a very low overall yield of active, useful protein. Because the non-glycosylated form of AFP exhibits the same biological properties as the glycosylated form and allows for a more standardized, consistent product due to the lack of glycosylation variability, non-glycosylated AFP is preferred for commercial production. Therefore, there exists a need for an efficient method to produce non-glycosylated human AFP for commercial and therapeutic applications.

SUMMARY OF THE INVENTION

The invention features a substantially pure nucleic acid molecule encoding non-glycosylated human alpha-fetoprotein (ng.HuAFP) or a non-glycosylated fragment thereof. In an embodiment, the nucleic acid molecule encoding ng.HuAFP includes nucleotides 45–1874 of the nucleic acid sequence set forth in SEQ ID NO: 5.

The invention also features a polypeptide comprising non-glycosylated human alpha-fetoprotein. In an embodiment of this feature of the invention, the polypeptide is substantially pure and has the amino acid sequence set forth in SEQ ID NO: 6. In another embodiment, the polypeptide is substantially pure and has the amino acid sequence set forth in SEQ ID NO: 8.

The invention further includes biologically active fragments and analogs of non-glycosylated recombinant HuAFP. In an embodiment, the biologically active fragments of non-glycosylated recombinant HuAFP include the amino acid sequence set forth in SEQ ID NO: 15 (Domain II), SEQ ID NO: 16 (Domain I+II), or SEQ ID NO: 17 (Domain II+III), or two or more of the amino acid sequences.

The invention also features a substantially pure nucleic acid molecule that includes (i) a nucleic acid molecule encoding ng.HuAFP including nucleotides 45 through 1874 of the nucleic acid sequence set forth in SEQ ID NO: 5, (ii) a promoter that is operably linked to the ng.HuAFP-encoding sequence and that enables expression of ng.HuAFP, and (iii) a leader sequence encoding a protein secretory signal that enables secretion of ng.HuAFP by a cell. In an embodiment, the cell is a prokaryotic cell (e.g., E. coli) or a eukaryotic cell (e.g., a yeast cell (e.g., Pichia pastoris) or an animal cell (e.g., a mammalian cell, such as a Chinese hamster ovary (CHO) cell). In a desired embodiment, the cell secretes ng.HuAFP into cell culture medium (i.e., a non-biological fluid). In another embodiment, the eukaryotic cell is in a transgenic animal (e.g., a mammal, such as a goat, sheep, camel, cow, pig, rabbit, horse, or llama). In yet another embodiment, the cell is a biological fluid-producing cell in a transgenic animal, the promoter enables expression of ng.HuAFP in the biological fluid-producing cell, and the leader sequence enables secretion of ng.HuAFP into a biological fluid (e.g., milk, urine, blood, or lymph) of the transgenic animal.

In an embodiment, the cell expressing ng.HuAFP is in a transgenic animal, the promoter driving expression of ng.HuAFP is a milk-producing cell-specific promoter that enables expression of ng.HuAFP in a milk-producing cell of the animal, and the leader sequence enables secretion of ng.HuAFP into the milk of the animal. In another embodiment, the cell expressing ng.HuAFP is in a transgenic animal, the promoter driving expression of ng.HuAFP is a urine-producing cell-specific promoter that enables expression of ng.HuAFP in a urine-producing cell of the animal, and the leader sequence enables secretion of ng.HuAFP into the urine of the animal. In yet another an embodiment, the cell expressing ng.HuAFP is in a transgenic animal, the promoter driving expression of ng.HuAFP is a blood-producing cell-specific promoter that enables expression of ng.HuAFP in a blood-producing cell of the animal, and the leader sequence enables secretion of ng.HuAFP into the blood of the animal. In still another embodiment, the cell expressing ng.HuAFP is in a transgenic animal, the promoter driving expression of ng.HuAFP is a lymph-producing cell-specific promoter that enables expression of ng.HuAFP in a lymph-producing cell of the animal, and the leader sequence enables secretion of ng.HuAFP into the lymph of the animal.

Another feature of the invention is a non-human transgenic organism that expresses and secretes ng.HuAFP into a biological fluid (e.g., milk, urine, saliva, seminal or vaginal fluid, synovial fluid, lymph fluid, amniotic fluid, the fluid within the yolk sac, the chorion, or the allantois of an egg, blood, sweat, and tears; or an aqueous solution produced by a plant, including, for example, exudates or guttation fluid, xylem, phloem, resin, and nectar). In an embodiment, the transgenic organism is a mammal (e.g., a goat, sheep, camel, cow, pig, rabbit, horse, or llama), a bird, a reptile, an amphibian, or a plant. In another embodiment, the ng.HuAFP is expressed from a transgene that includes: (i) a nucleic acid molecule encoding ng.HuAFP including nucleotides 45 through 1874 of the nucleic acid sequence set forth in SEQ ID NO: 5, (ii) a promoter that is operably linked to the ng.HuAFP-encoding sequence such that the promoter enables expression of ng.HuAFP by cells of the organism that secrete a protein into a biological fluid, and (iii) a leader sequence encoding a protein secretory signal that enables secretion of ng.HuAFP into the biological fluid by the cells of the organism. In yet another embodiment, the promoter is a milk-, urine-, blood-, or lymph-specific promoter and the leader sequence enables secretion of ng.HuAFP into the milk, urine, blood, or lymph, respectively, of the organism. In still another embodiment, the organism is a mouse or a goat.

The invention also features a non-human mammal's milk, urine, blood, or lymph that includes ng.HuAFP. In an embodiment, the ng.HuAFP is soluble and is produced by a non-human transgenic mammal whose milk-, urine-, blood-, or lymph-producing cells express a transgene that comprises: (i) a nucleic acid molecule encoding ng.HuAFP including nucleotides 45 through 1874 of the nucleic acid sequence set forth in SEQ ID NO: 5, (ii) a milk-, urine-, blood-, or lymph-specific promoter such that the promoter is operably linked to the ng.HuAFP-encoding sequence and enables expression of ng.HuAFP by the milk-, urine-, blood-, or lymph-producing cells of the mammal, and (iii) a leader sequence encoding a protein secretory signal that enables secretion of ng.HuAFP by the milk-, urine-, blood-, or lymph-producing cells into milk, urine, blood, or lymph, respectively, of the mammal.

The invention also features a method of producing ng.HuAFP by the following steps: (a) providing a cell transduced with a transgene that comprises: (i) a nucleic acid molecule encoding ng.HuAFP including nucleotides 45 through 1874 of the nucleic acid sequence set forth in SEQ ID NO: 5, (ii) a promoter that is operably linked to the ng.HuAFP-encoding sequence such that the promoter enables expression of ng.HuAFP by the cell, and (iii) a leader sequence encoding a protein secretory signal that enables secretion of ng.HuAFP by the cell; and (b) growing the transduced cell such that the cell expresses and secretes ng.HuAFP.

In an embodiment, the cell is a prokaryotic cell (e.g., *E. coli*) or a eukaryotic cell (e.g., a yeast cell (e.g., *Pichia pastoris*) or a mammalian cell (e.g., a CHO cell, or a milk-, urine-, blood-, or lymph-producing cell)).

The invention also features a method of producing ng.HuAFP by the following steps: (a) providing a transgenic organism (e.g., a mammal (e.g., a goat, sheep, camel, cow, pig, rabbit, horse, or llama), a bird, a reptile, an amphibian, or a plant) that includes a transgene having (i) a nucleic acid molecule encoding ng.HuAFP including nucleotides 45 through 1874 of the nucleic acid sequence set forth in SEQ ID NO: 5, (ii) a promoter that is operably linked to the ng.HuAFP-encoding sequence such that the promoter enables expression of ng.HuAFP in a biological fluid-producing cell of the transgenic organism, and (iii) a leader sequence encoding a protein secretory signal that enables secretion of ng.HuAFP by the biological fluid-producing cell into a biological fluid of the transgenic organism; and (b) collecting the biological fluid that includes ng.HuAFP from the transgenic organism.

In an embodiment, the biological fluid is milk, urine, saliva, seminal or vaginal fluid, synovial fluid, lymph fluid, amniotic fluid, the fluid within the yolk sac, the chorion, or the allantois of an egg, blood, sweat, or tears; or an aqueous solution produced by a plant, including, for example, exudates or guttation fluid, xylem, phloem, resin, and nectar. In a desired embodiment, the biological fluid is milk, urine, blood, or lymph, and ng.HuAFP is purified from the milk, urine, blood, or lymph, respectively. In another embodiment, the promoter is a milk-, urine-, blood-, or lymph-specific promoter that enables expression of ng.HuAFP in milk-, urine-, blood-, or lymph-producing cells, respectively, of the transgenic organism. In yet another embodiment, the transgenic organism expresses and secretes ng.HuAFP in two or more biological fluids (e.g., milk and urine, milk and blood, urine and blood, or milk, urine, and blood).

Another feature of the invention is a method of treating a patient in need of ng.HuAFP by administering to the patient a therapeutically-effective amount of ng.HuAFP that is purified from a cell culture medium.

Another feature of the invention is a method of treating a patient in need of ng.HuAFP by administering to the patient a therapeutically-effective amount of a biological fluid (e.g., milk, urine, saliva, seminal or vaginal fluid, synovial fluid, lymph fluid, amniotic fluid, the fluid within the yolk sac, the chorion, or the allantois of an egg, blood, sweat, and tears; or an aqueous solution produced by a plant, including, for example, exudates or guttation fluid, xylem, phloem, resin, and nectar), or extract thereof, that includes ng.HuAFP that is obtained from a transgenic non-human organism (e.g., a mammal (e.g., a mouse, goat, sheep, camel, cow, pig, rabbit, horse, ox, or llama), a bird, a reptile, an amphibian, or a plant). In a desired embodiment, n.g.HuAFP has the sequence set forth in SEQ ID NO: 8. In another embodiment, the biological fluid is milk. In yet another embodiment, ng.HuAFP is purified from the transgenic non-human organism's biological fluid (e.g., ng.HuAFP purified from the milk, urine, blood, or lymph of a mammal). In various desired embodiments, the method may be used to inhibit or treat an immunologic disorder, e.g., infection with the human immunodeficiency virus (HIV), cancer cell growth, to induce bone marrow cell proliferation (for example, after a bone marrow transplant or after administration of a myelotoxic treatment such as chemotherapy or radiation treatment), or as an immunosuppressive agent (for example, to inhibit autoreactive immune cell proliferation, to inhibit rejection of a transplanted organ (e.g., graft-versus-host disease), or to inhibit or treat an autoimmune disorder, e.g., rheumatoid arthritis, muscular dystrophy, systemic lupus erythematosus, myasthenia gravis, multiple sclerosis, insulin-dependent diabetes mellitus, or psoriasis).

The invention also features a therapeutic composition that includes ng.HuAFP having the amino acid sequence set forth in SEQ ID NO: 8.

The invention also features the use of ng.HuAFP having the amino acid sequence set forth in SEQ ID NO: 8 in the manufacture of a medicament for treating an individual diagnosed with or suffering from a disease (e.g., cancer, rheumatoid arthritis, muscular dystrophy, systemic lupus erythematosus, myasthenia gravis, multiple sclerosis, insulin-dependent diabetes mellitus, or psoriasis).

The invention also features the use of ng.HuAFP having the amino acid sequence set forth in SEQ ID NO: 8 in the manufacture of a medicament for enhancing cell proliferation (e.g., to induce bone marrow cell proliferation (for example, after a bone marrow transplant or after administration of a myelotoxic treatment such as chemotherapy or radiation treatment)).

The invention also features the use of ng.HuAFP having the amino acid sequence set forth in SEQ ID NO: 8 in the manufacture of a medicament for use as an immunosuppressive agent (for example, to inhibit autoreactive immune cell proliferation; or to inhibit rejection of a transplanted organ (e.g., graft-versus-host disease)).

In an embodiment of all features of the invention, the ng.HuAFP is recombinant (r.ng.HuAFP).

In all of the features of the invention, the organism is an animal (e.g., a mammal, bird, reptile, or amphibian) or a plant. Exemplary mammals include goats, sheep, camels, cows, pigs, rabbits, horses, and llamas. Exemplary birds include chickens, turkeys, geese, ostriches, quails, and ducks. Exemplary plants include species from the genera *Arabidopsis, Medicago, Fragaria, Vigna, Lotus, Onobrychis, Trifolium, Trigonella, Citrus, Linum, Geranium, Manihot, Daucus, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum,* or *Datura*. The plant can also be selected from the group consisting of a Conifer, Petunia, Tomato, Potato, Tobacco, Lettuce, Sunflower, Oilseed rape, Flax, Cotton, Sugarbeet, Celery, Soybean, Alfalfa, Lotus, Cucumber, Carrot, Eggplant, Cauliflower, Horseradish, Morning Glory, Poplar, Walnut, Apple, Grape, Asparagus, Rice, Maize, Millet, Onion, Barley, Orchard grass, Oat, Rye, Wheat, corn, alfalfa, turgrass, azolla, floating rice, water hyacinth, and watermelon, or it can be selected from aquatic plants capable of vegetative multiplication or flowering plants that grow submerged in water.

In other desired embodiments of the invention, the biological fluid is milk, urine, saliva, seminal fluid, vaginal fluid, synovial fluid, lymph fluid, amniotic fluid, fluid surrounded by the yolk sac, the chorion, or the allantois of an egg, blood, sweat, tears, plant exudates, guttation fluid, xylem, phloem, resin, or nectar. Desirably, the biological fluid is milk.

In other desired embodiments of the invention, the organism is a mammal and ng.HuAFP is expressed by cells of the mammal that are responsible for producing proteins that are secreted into a biological fluid of the organism (e.g., milk-producing cells, urine-producing cells, blood-producing, or lymph-producing cells). In desired embodiments, ng.HuAFP is expressed by milk-producing cells of the mammal under the control of a milk-specific promoter, which can be selected from the group consisting of an alpha S-1 casein promoter, an alpha S2-casein promoter, a beta casein promoter, a gamma casein promoter, a kappa casein promoter, a whey acidic protein (WAP) promoter, an alpha-lactalbumin promoter, a beta-lactoglobulin promoter, and a long terminal repeat (LTR) promoter of the mouse mammary tumor virus (MMTV). Expression of ng.HuAFP under control of any one of these promoters enables secretion of the polypeptide into milk of the mammal.

In other desired embodiments, ng.HuAFP is expressed by urine-producing cells of the mammal under the control of an urine-specific promoter, which can be selected from the group consisting of an uroplakin II promoter and an uromodulin promoter. Expression of ng.HuAFP under control of any one of these promoters enables secretion of ng.HuAFP into urine of the mammal.

In yet other desired embodiments, ng.HuAFP is expressed by blood-producing cells of the mammal under the control of a blood-specific promoter (e.g., an albumin promoter and an alpha-fetoprotein promoter). In yet another desired embodiment, ng.HuAFP is expressed by blood-producing cells of the mammal under the control of a lymphocyte-specific promoter. Expression of ng.HuAFP under control of any one of these promoters enables secretion of ng.HuAFP into blood of the mammal.

In still other desired embodiments, ng.HuAFP is expressed by lymph-producing cells of the mammal under the control of a lymph-specific promoter. Expression of ng.HuAFP under control of a lymph-specific promoter enables secretion of ng.HuAFP into lymph of the mammal.

In still other embodiments, the organism is a bird and ng.HuAFP is expressed by cells of the bird under the control of an avian-specific promoter, which can be selected from the group consisting of an ovalbumin promoter or an apo-B promoter. Expression of ng.HuAFP under the control of any one of these promoters enables secretion of ng.HuAFP into amniotic fluid, or fluid surrounded by the yolk sac, the chorion, or the allantois of an egg.

In still further embodiments of the invention the organism is a plant and ng.HuAFP is expressed by cells of the plant under the control of a plant-specific promoter, which can be selected from the group consisting of the Cauliflower Mosaic Virus (CaMV) 35S promoter, the CaMV 19S promoter, the T-DNA mannopine synthetase promoter, the glutathione-S-transferase isoform II (GST-II-27) promoter, the dexamethasone (DEX) promoter, the cell promoter, the chalcone synthase (CHS) promoter, the PATATIN promoter, the nopaline synthase (NOS) promoter, the octopine synthase (OCS) promoter, the *Solanum tuberosum* leaf/stem (ST-LS)1 promoter, the soybean heat shock protein hsp17.5-E, the hsp17.3-B promoter, the *Parasponia andersoni* hemoglobin promoter, the phenylalanine ammonia-lyase promoter, the *petunia* 5-enolpyruvylshikimate-3-phosphate synthase gene promoter, the sucrose synthase promoter, the chlorophyll a/b (Cab) promoter, the maize rbcS promoter, the pea rbcS-3A promoter, the light-inducible promoter from the small subunit of ribulose bisphosphate carboxylase (ss-RUBICSO), the abscisic acid (ABA) responsive gene sequence promoter, the ABA-inducible HVA1 promoter, the ABA-inducible HVA22 promoter, the rd29A promoter, the 23-kDa zein gene promoter, the French bean β-phaseolin gene promoter, the vegetative storage protein (vspB) promoter, the *Arabidopsis* cdc2a promoter, the *Arabidopsis* SAG12 promoter, the pathogen-inducible PR-1 promoter, the b-1,3 glucanase promoter, the alcohol dehydrogenase (ADH) I promoter, the ADH II promoter, the *Rhizobium meliloti* FIXD gene promoter, the rol A promoter, the rol B promoter, and the rol C promoter. Expression of ng.HuAFP under any one of these plant-specific promoters enables production of ng.HuAFP in the leaf, stem, root, or fruit of the plant, as well as secretion of ng.HuAFP into an exudate or guttation fluid of the plant, or the xylem, phloem, resin, or nectar of the plant.

In other embodiments, ng.HuAFP is expressed under the control of an inducible promoter, thereby providing temporal and/or spatial control over expression. In a desired embodiment, an inducible promoter is selected from the group consisting of a heat shock protein promoter, a metallothionien promoter, a MMTV-LTR promoter, and an ecdysone promoter. Other modes of regulating expression of ng.HuAFP include the use of muristerone A and tetracycline/doxycycline selection.

Other features and advantages of the invention will be apparent from the following detailed description, and from the claims.

Definitions

By "biological fluid" is meant an aqueous solution produced by an organism, such as a mammal, bird, amphibian, or reptile, which contains proteins that are secreted by cells that are bathed in the aqueous solution. Examples of a biological fluid include, for example, milk, urine, saliva, seminal fluid, vaginal fluid, synovial fluid, lymph fluid, amniotic fluid, the fluid within the yolk sac, the chorion, and the allantois of an egg, blood, sweat, and tears; as well as an aqueous solution produced by a plant, including, for example, exudates and guttation fluid, xylem, phloem, resin, and nectar. Further included are extracts of animal tissue, as well as plant extracts, which include aqueous or organic extractions of any plant structure, including the shoot, leaf, root, stem, and seed. Plant extracts can also be derived from exudates or guttation fluids.

By "biological-fluid producing cell" is meant a cell that is bathed by a biological fluid and that secretes a protein into the biological fluid.

By "blood-producing cell" is meant a cell (e.g., a liver epithelial cell, a spleen epithelial cell, a bone marrow cell, a thymus epithelial cell, a blood vessel endothelial cell, a bone marrow cell (e.g., a lymphocyte (e.g., a B or T lymphocyte), and a red blood cell)) that secretes a protein into blood.

By "blood-specific promoter" is meant a promoter that naturally directs expression of a gene in a cell that secretes a protein into blood (e.g., a liver epithelial cell, a spleen epithelial cell, a bone marrow cell, a thymus epithelial cell, a blood vessel endothelial cell, and a lymphocyte (e.g., a B or T lymphocyte)). An example of a blood-specific promoter is the albumin promoter/enhancer, which has been described and can be used to achieve liver-specific expression of an exogenous gene (see, e.g., Shen et al., DNA 8:101–108, 1989; Tan et al., Dev. Biol. 146:24–37, 1991; McGrane et al., TIBS 17:40–44, 1992; Jones et al., J. Biol. Chem. 265:14684–14690, 1990; and Shimada et al., FEBS Letters 279:198–200, 1991). The alpha-fetoprotein gene promoter is also particularly useful.

By "embryonal cell" is meant a cell that is capable of being a progenitor to all the somatic and germ-line cells of an organism. Exemplary embryonal cells are embryonic stem cells (ES cells) and fertilized oocytes. Preferably, the embryonal cells of the invention are mammalian embryonal cells.

By "exogenous," as used herein in reference to a gene or a polypeptide, is meant a gene or polypeptide that is not normally present in an animal. For example, ng.HuAFP is exogenous to a goat.

By "expression vector" is meant a genetically engineered plasmid or virus, derived from, for example, a bacteriophage, adenovirus, retrovirus, poxvirus, herpesvirus, or artificial chromosome, that is used to transfer an ng.HuAFP coding sequence, operably linked to a promoter, into a host cell, such that the encoded r.ng,HuAFP is expressed within the host cell.

By "human alpha-fetoprotein" or "HuAFP" or "rHuAFP" is meant a polypeptide having substantially the same amino acid sequence as the mature alpha-fetoprotein (amino acids 19–609) set forth in Genbank Accession No. V01514 (SEQ ID NO: 4) and encoded by nucleotides 99–1874 of the cDNA sequence set forth in Genbank Accession No. V01514 (SEQ ID NO: 3) and reported in Morinaga et al. (Proc. Natl. Acad. Sci. USA 80:4604–4608, 1983).

By "fragment" as applied to a non-glycosylated HuAFP polypeptide, is meant at least 5 contiguous amino acids, preferably at least 10 contiguous amino acids, more preferably at least 20, 50, or 100 contiguous amino acids, and most preferably at least 200 to 400 or more contiguous amino acids in length and desirably includes a glutamine residue in place of an asparagine residue at amino acid position 233 of SEQ ID NO: 4. HuAFP fragments and analogs preferably retain biological activity. Fragments and analogs of HuAFP are described in, e.g., U.S. Pat. Nos. 5,965,528 and 5,384,250.

Recombinant HuAFP fragments of interest include, but are not limited to, Domain I (amino acids 1 (Arg)-198 (Ser), SEQ ID NO: 9), Domain II (amino acids 199 (Ser)-390 (Ser), SEQ ID NO: 15), Domain III (amino acids 391 (Gln)-591 (Val), SEQ ID NO: 11), Domain I+II (amino acids 1 (Arg)-390 (Ser), SEQ ID NO: 16), Domain II+III (amino acids 199 (Ser)-591 (Val), SEQ ID NO: 17), and rHuAFP Fragment I (amino acids 267 (Met)-591 (Val), SEQ ID NO: 14). The numbering of the recombinant HuAFP fragments described above is based on the sequence of mature AFP lacking amino acids 1–18 of the signal sequence. Therefore, the arginine residue at position 1 of the HuAFP fragments corresponds to amino acid 19 of precursor AFP. The HuAFP fragments described above can be generated as non-glycosylated fragments by substituting the asparagine residue at position 233 of SEQ ID NO: 4 with, e.g., a glutamine. Activity of a fragment is evaluated experimentally using conventional techniques and assays.

By "human alpha-fetoprotein precursor" is meant a polypeptide having substantially the same amino acid sequence as amino acids 1–609 set forth in Genbank Accession No. V01514 (SEQ ID NO: 2) and encoded by nucleotides 45–1874 of the cDNA sequence set forth in Genbank Accession No. V01514 (SEQ ID NO: 1).

By a "leader sequence" or a "signal sequence" is meant a nucleic acid sequence that encodes a protein secretory signal, and, when operably linked to a downstream nucleic acid molecule encoding ng.HuAFP, directs ng.HuAFP secretion. The leader sequence may be the native human alpha-fetoprotein leader, an artificially-derived leader, or may obtained from the same gene as the promoter used to direct transcription of the ng.HuAFP coding sequence, or from another protein that is normally secreted from a cell.

By "lymph-producing cell" is meant a cell (e.g., epithelial cells of the lymphatic vessels and cells of the lymph node, lymphocytes (e.g., B and T lymphocytes), and macrophages) that secretes a protein into lymphatic fluid.

By "lymph-specific promoter" is meant a promoter that naturally directs expression of a gene in a cell that secretes a protein into lymphatic fluid (e.g., epithelial cells of the lymphatic vessels and cells of the lymph node, lymphocytes (e.g., B and T lymphocytes), and macrophages).

By "milk-producing cell" is meant a cell (e.g., a mammary epithelial cell) that secretes a protein into milk.

By "milk-specific promoter" is meant a promoter that naturally directs expression of a gene in a cell that secretes a protein into milk (e.g., a mammary epithelial cell) and includes, for example, the casein promoters, e.g., alpha casein promoter (e.g., alpha S-1 casein promoter and alpha S2-casein promoter), beta casein promoter (e.g., the goat beta casein gene promoter (DiTullio, BioTechnology 10:74–77, 1992), gamma casein promoter, and kappa casein promoter; the whey acidic protein (WAP) promoter (Gorton et al., BioTechnology 5: 1183–1187, 1987); the beta-lactoglobulin promoter (Clark et al., BioTechnology-7: 487–492, 1989); and the alpha-lactalbumin promoter (Soulier et al., FEBSLetts. 297:13, 1992). Also included are promoters that are specifically activated in mammary tissue and are thus useful in accordance with this invention, for example, the long terminal repeat (LTR) promoter of the mouse mammary tumor virus (MMTV).

By "operably linked" is meant that a gene and one or more regulatory sequences are connected in such a way as to permit gene expression when the appropriate molecules (e.g., transcriptional activator proteins) are bound to the regulatory sequences.

By "plant" is meant a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

By "promoter" is meant a minimal sequence sufficient to direct transcription. Also included in the invention are those promoter elements which are sufficient to render promoter-dependent gene expression controllable for cell type-specific, tissue-specific, temporal-specific, or inducible by external signals or agents; such elements may be located in the 5' or 3' or intron sequence regions of the native gene.

By "purified" or "substantially pure" is meant that ng.HuAFP secreted into a biological fluid (e.g., milk, urine, blood, lymph, amniotic fluid, fluid surrounded by the yolk sac, the chorion, or the allantois of an egg, guttation fluid, xylem, phloem, resin, or sap) is partially or completely separated from other components (e.g., proteins, lipids, and water) naturally found in the biological fluid, thus increasing the effective concentration of ng.HuAFP relative to unpurified ng.HuAFP found in a biological fluid.

By "non-glycosylated human alpha-fetoprotein" or "ng.HuAFP" is meant a polypeptide having substantially the same amino acid sequence as the mature human alpha-fetoprotein described above, except including a mutation at amino acid position 233 of SEQ ID NO: 4 from an asparagine residue to a glutamine residue (as set forth in SEQ ID NO: 6), thereby eliminating the single glycosylation site. The nucleic acid sequence of the precursor non-glycosylated human alpha-fetoprotein includes nucleotides 45 through 1874 of the sequence set forth in SEQ ID NO: 5.

By "ng.HuAFP secretory signal" or "ng.HuAFP signal peptide" or "ng.HuAFP leader" or "ng.HuAFP signal sequence" is meant a polypeptide having substantially the same amino acid sequence as amino acids 1–18 set forth in Genbank Accession No. V01514 (encoded by nucleotides 45–98). The protein secretory signal is cleaved from ng.HuAFP during protein maturation and extracellular secretion.

By "substantially pure nucleic acid molecule" is meant a nucleic acid molecule that is free of the genes which, in the naturally-occurring genome of the organism from which the nucleic acid molecule of the invention is derived, flank the gene. The term therefore includes, for example, a recombinant DNA molecule that is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA that is part of a hybrid gene containing a nucleotide sequence not native to the gene or encoding additional polypeptide sequence, as well as the corresponding mRNA.

By "therapeutically-effective amount" is meant an amount of non-glycosylated human alpha-fetoprotein or a fragment thereof that, when administered to a patient, inhibits or stimulates a biological activity modulated by human alpha-fetoprotein. Such biological activities include inhibiting the proliferation of a neoplasm or an autoreactive immune cell, or stimulating proliferation of a cell (e.g., a bone marrow cell). The therapeutically-effective amount may vary depending upon a number of factors, including medical indication, the length of time of administration, and the route of administration. For example, ng.HuAFP can be administered systemically in the range of 0.1 ng–10 g/kg body weight, preferably in the range of 1 ng–1 g/kg body weight, more preferably in the range of 10 ng–100 mg/kg body weight, and most preferably in the range of 25 µg–10 mg/kg body weight.

By "transformation," "transfection," or "transduction" is meant any method for introducing foreign molecules into a cell. Lipofection, DEAE-dextran-mediated transfection, microinjection, nuclear transfer (see, e.g., Campbell et al. Biol. Reprod. 49:933–942, 1993; Campbell et al., Nature 385:810–813, 1996), protoplast fusion, calcium phosphate precipitation, transduction (e.g., bacteriophage, adenoviral retroviral, or other viral delivery), electroporation, and biolistic transformation are just a few of the methods known to those skilled in the art which may be used.

By "transformed cell," "transfected cell," or "transduced cell," is meant a cell (or a descendent of a cell) into which a nucleic acid molecule encoding ng.HuAFP has been introduced by means of recombinant DNA techniques. The nucleic acid molecule may be stably incorporated into the host chromosome, or may be maintained episomally.

By "transgene" is meant any piece of a nucleic acid molecule that is inserted by artifice into a cell, or an ancestor thereof, and becomes part of the genome of the animal which develops from that cell. Such a transgene may include a gene which is partly or entirely exogenous (i.e., foreign) to the transgenic animal, or may represent a gene having identity to an endogenous gene of the animal.

By "transgenic" is meant any cell that includes a nucleic acid molecule that has been inserted by artifice into a cell, or an ancestor thereof, and becomes part of the genome of the animal which develops from that cell. Preferably, the transgenic animals are transgenic mammals (e.g., mice, goats, sheep, camels, cows, pigs, rabbits, horses, oxen, or llamas). Preferably the nucleic acid molecule (transgene) is inserted by artifice into the nuclear genome (i.e., a chromosome), although the transgene may also be episomally maintained (e.g., carried on a vector that contains an origin of replication such as the Epstein-Barr Virus oriP).

By "urine-producing cell" is meant a cell (e.g., a bladder or kidney epithelial cell) that secretes a protein into urine.

By "urine-specific promoter" is meant a promoter that naturally directs expression of a gene in a cell that secretes a protein into urine (e.g., a bladder epithelial cell). Examples of a urine-specific promoter are the uroplakin II gene promoter and the uromodulin gene promoter.

μL-1:40); Lane 9: BC934-1-63, d9, (4 μL-1:40); Lane 10: BC934-1-64, d9, (4 μL-1:40).

Figure 4:
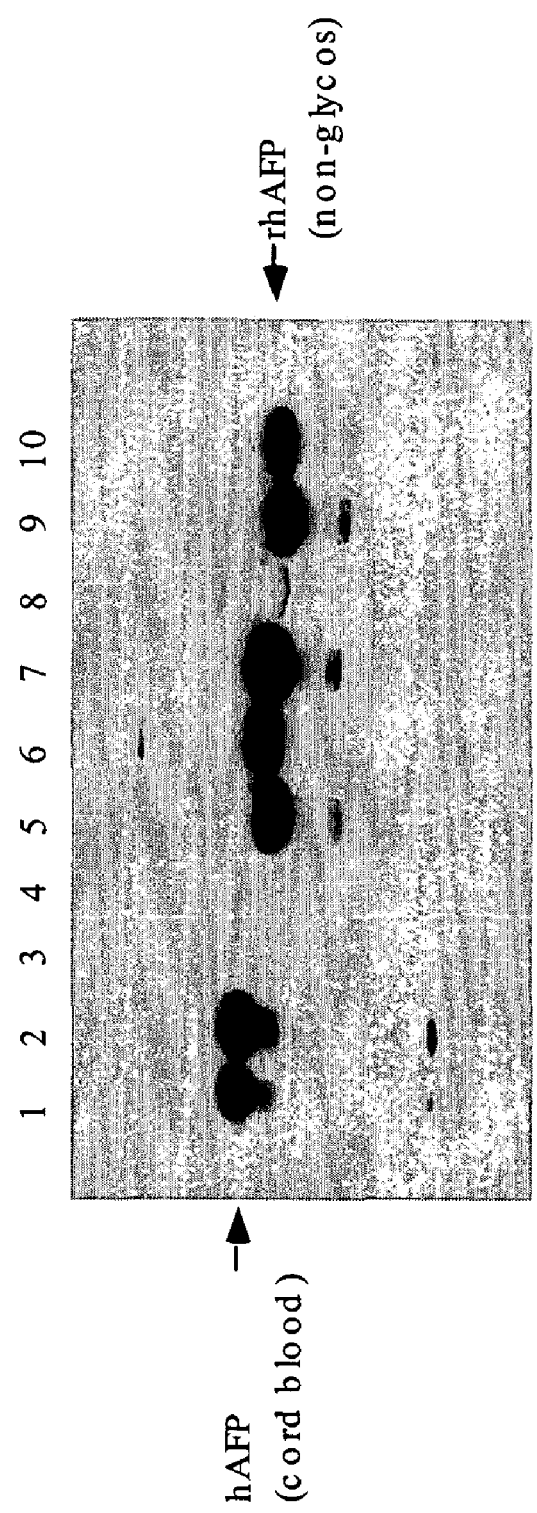

FIG. 4 is an image of a Western blot showing the presence of ng.HuAFP in transgenic mouse milk samples. Lane 1: hAFP (50 ng); Lane 2: hAFP (100 ng); Lane 3: Molecular weight standard; Lane 4: Negative (nontransgenic) mouse milk; Lanes 5–10: ng.HuAFP. Lane 5: BC1055-1-9 (4 μL-1:40); Lane 6: BC1055-1-10 (4 μL-1:400); Lane 7: BC1055-1-37 (4 μL-1:400); Lane 8: BC1055-1-44 (4 μL-1:40); Lane 9: BC1055-1-74 (4 μL-1:40); Lane 10: BC1055-1-85 (4 μL-1:40).

Figure 5:
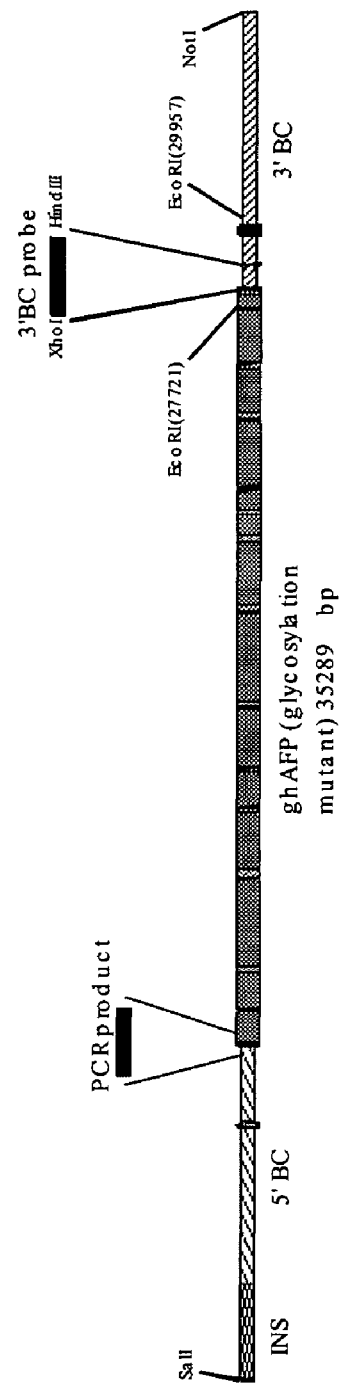

FIG. 5 is a diagram showing a schematic of the BC1055 (ng.HuAFP) construct and the position of a 332 bp PCR product (labeled "PCR Product") that spans the junction of the 5' β-casein and the 5' ng.HuAFP sequences. Also indicated is the position of the PCR primer 3' BC probe, which is used for Southern blot analysis.

Figure 6:
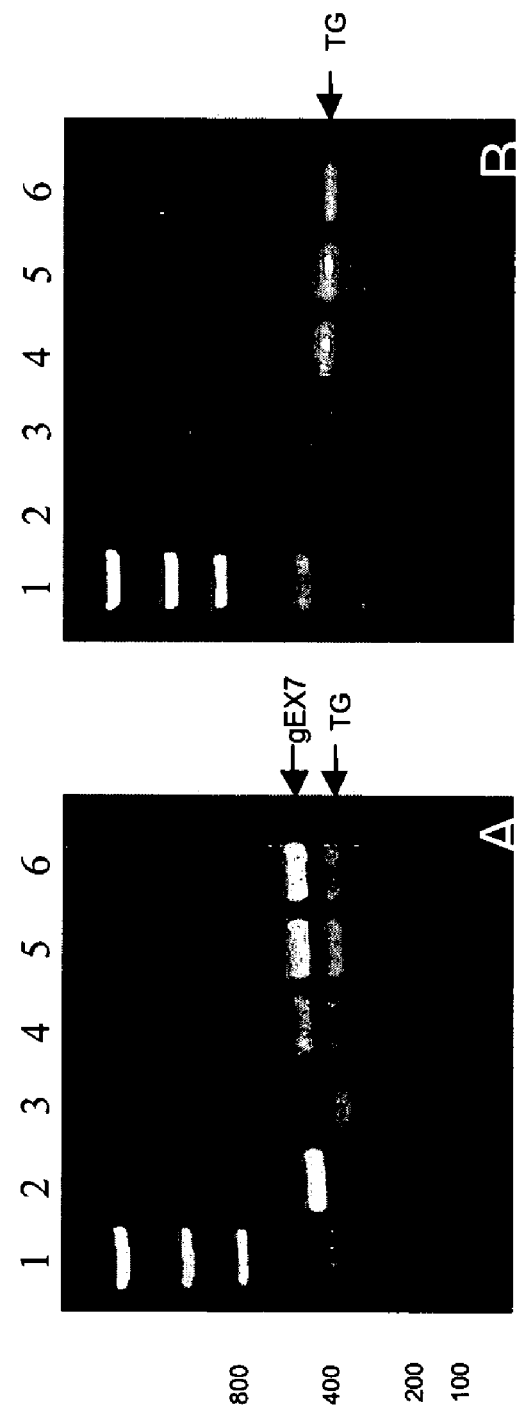

FIGS. 6A and 6B are photographs showing the result of PCR analysis of blood and ear tissue taken from Founder Goat F093 containing the ng.HuAFP transgene. FIG. 6A shows the result of duplex PCR analysis using the goat exon 7 primer pair (410 bp product) with a hAFP-specific primer pair (332 bp product). FIG. 6B shows the result of PCR analysis using the hAFP-specific primer pair alone. The template DNA in both experiments were the same. Lane 1: DNA size standards; Lane 2: Non-transgenic goat blood sample; Lane 3: hAFP positive goat cell line (clone 7); Lane 4: Ear tissue from hAFP-positive abortus, F026; Lane 5: Blood tissue from F093; and Lane 6: Ear tissue from F093.

Figure 7:
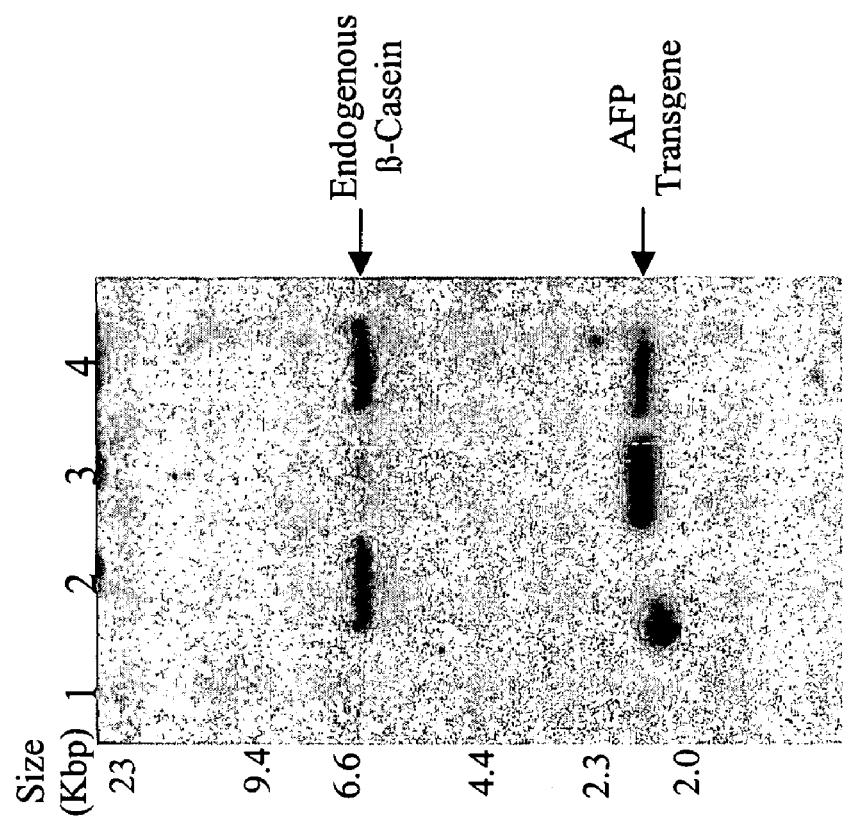

FIG. 7 is an image showing the result of a Southern blot analysis of Founder Goat F093. Five μg of DNA was digested with EcoRI, separated by electrophoresis, and blotted to Genescreen Plus (New England Nuclear). The blot was then hybridized with a goat β-casein probe, washed, and autoradiographed. Lane 1: λHindIII, molecular weight markers; Lane 2: Non-transgenic goat ear tissue DNA; Lane 3: F026, hAFP-positive abortus ear tissue DNA; Lane 4: F093, founder goat blood DNA.

FIGS. 8A and 8B are photographs showing the result of fluorescence in situ hybridization (FISH) analysis of Founder Goat F093. FIG. 8A shows a representative example of metaphase chromosomes of F093 cultured leukocytes. The transgene signal is indicated by the white dot and the arrow. The chromosomes are visualized with DAPI stain. Magnification: 1000×. FIG. 8B shows a representative field of interphase nuclei of F093 cultured leukocytes. The transgene signals are white and indicated by the arrows. The DNA in the nuclei is visualized with DAPI stain. Magnification: 1000×.

DETAILED DESCRIPTION OF THE INVENTION

The present invention features biologically-active non-glycosylated human alpha-fetoprotein (ng.HuAFP), the nucleic acid sequence encoding ng.HuAFP, and methods for producing ng.HuAFP. The methods of the invention include production of ng.HuAFP in a cell (e.g., a prokaryotic cell (e.g., *E. coli*) or a eukaryotic cell (e.g., a yeast cell (e.g., *Pichia pastoris*) or a mammalian cell)). Methods for the production of rHuAFP in prokaryotic cells, which can be used to produce ng.HuAFP, can be found in U.S. Pat. Nos. 5,384,250 and 6,331,611, hereby incorporated by reference. Methods that can be used to produce ng.HuAFP in mammalian cells can be found in U.S. Ser. No. 09/936,020. A detailed description of the various mammalian expression systems and methods for expressing recombinant proteins in mammalian cells are provided in Ausubel et al. (Current Protocols in Molecular Biology, John Wiley and Sons, Inc., New York, N.Y., pp. 16.12.1–16.20-16 and A.5.23–A.5.30, 1997).

The methods of the invention also include production of ng.HuAFP in a transgenic organism, particularly a mammal, such as a ruminant (e.g., a cow, a sheep, and a goat), a horse, a camel, an ox, a llama, a pig, a rabbit, and a mouse, but also including birds (e.g., chickens, turkeys, geese, quail, ducks, and ostriches), amphibians, reptiles, and plants. The transgene contains ng.HuAFP, which includes the human AFP coding region altered to contain a substitution of an asparagine for a glutamine at position 251 of the precursor AFP or at position 233 of the mature AFP lacking a signal sequence. The ng.HuAFP coding region is fused downstream of a nucleic acid sequence containing a transcriptional promoter. Between the promoter and the protein coding region is a leader sequence encoding a protein secretory signal. Depending upon the promoter and secretory signal employed, expression of ng.HuAFP enables secretion into a biological fluid, for example milk, urine, blood, lymph, amniotic fluid, the fluid surrounded by the yolk sac, the chorion, or the allantois of an egg, or guttation fluid of the transgenic organism. Additional nucleic acid elements, such as transcriptional enhancers, transcriptional and translational terminator sequences, 3' untranslated regions that enhance mRNA stability, and introns that enhance expression may also be included in the transgenic construct. The ng.HuAFP is expressed in the transgenic animal, secreted into a biological fluid (e.g., milk, urine, blood, lymph, etc.), which can be collected, and purified from the fluid.

Secretion of ng.HuAFP into a biological fluid of a transgenic organism (e.g., milk, urine, and lymph) facilitates its purification and obviates removal of blood products and culture medium additives, some of which may be toxic, carcinogenic, or infectious. Moreover, milk containing ng.HuAFP may be directly consumed by humans or other mammals. Expression of ng.HuAFP in urine allows the use of both male and female animals for ng.HuAFP production. In addition, ng.HuAFP is produced as soon as the animals begin to produce urine. Finally, purification of ng.HuAFP from urine is relatively straightforward, as urine normally contains a low protein content.

Transgene Constructs

Useful promoters for the expression of a ng.HuAFP transgene in mammary tissue include promoters that naturally drive the expression of mammary-specific proteins, such as milk proteins, although any promoter that permits secretion of the transgene product into milk may be used. These include, e.g., the promoters that naturally direct expression of whey acidic protein (WAP), alpha S1-casein, alpha S2-casein, beta-casein, kappa-casein, beta-lactoglobulin, and alpha-lactalbumin (see, e.g., Drohan et al., U.S. Pat. No. 5,589,604; Meade et al. U.S. Pat. No. 4,873,316; and Karatzas et al., U.S. Pat. No. 5,780,009).

Useful promoters for the expression of a ng.HuAFP transgene in urinary tissue are the uroplakin and uromodulin promoters (Kerr et al., Nat. Biotechnol. 16:75–79, 1998; and Zbikowska et al., Transgenic Res. 11:425–435, 2002), although any promoter that permits secretion of the transgene product into urine may be used.

The transgene construct preferably includes a leader sequence downstream from the promoter. The leader sequence is a nucleic acid sequence that encodes a protein secretory signal, and, when operably linked to a downstream nucleic acid molecule encoding ng.HuAFP, directs ng.HuAFP secretion. The leader sequence may be obtained from the same gene as the promoter used to direct transcription of the nucleic acid molecule encoding ng.HuAFP (for example, a gene that encodes a milk-specific protein). Alternatively, a leader sequence encoding the native human AFP protein secretory signal (amino acids 1–19 of Genbank Accession No. V01514) may be employed; nucleotides 45–101 of Genbank Accession No. V01514 encode the native human AFP protein secretory signal. Other options include use of a leader sequence that encodes a protein secretory signal from any other protein that is normally secreted from a cell, an artificial leader sequence that encodes an artificial protein secretory signal, or a hybrid leader sequence (e.g., a fusion of the goat β-casein and human AFP leader sequences).

In addition, the transgene construct preferably includes a transcription termination site, a signal for polyadenylation of the transcribed mRNA, and a translation termination signal. The transgene may also encode any 3' untranslated region (UTR), which increases stability of the ng.HuAFP mRNA, for example, a 3' UTR from the bovine growth hormone gene, a milk protein gene, or a globin gene.

The transgene construct may also include a transcriptional enhancer upstream or downstream from the transcribed region of the transgene, such as an enhancer from a viral (e.g., SV40) or mammalian (e.g., casein) gene.

The transgene construct may further include an intron that increases the level of expression of the transgene. The intron may be placed between the transcription initiation site and the translational start codon, 3' of the translational stop codon, or within the coding region of the transgene. The intron should include a 5' splice site (i.e., a donor site), a 3' splice site (i.e., an acceptor site), and preferably, at least 100 nucleotides between the two sites. Any intron that is known in the art to increase expression of a transgene (e.g., an intron from a ruminant casein gene) may be used.

The ng.HuAFP transgene may be carried within a circular plasmid, a cosmid vector, or other vector, such as a vector derived from a virus. The vector may contain additional sequences that facilitate its propagation in prokaryotic and eukaryotic cells, for example, drug-selectable markers (e.g., for ampicillin resistance in *E. coli*, or G-418 resistance in mammalian cells) and origins of replication (e.g., colE1 for replication in prokaryotic cells, and oriP for replication in mammalian cells).

Animal Promoters

Useful promoters for the expression of ng.HuAFP in mammary tissue include promoters that naturally drive the expression of mammary-specific polypeptides, such as milk proteins, although any promoter that permits secretion of ng.HuAFP into milk can be used. These include, e.g., promoters that naturally direct expression of whey acidic protein (WAP), alpha S1-casein, alpha S2-casein, beta-casein, kappa-casein, beta-lactoglobulin, alpha-lactalbumin (see, e.g., Drohan et al., U.S. Pat. No. 5,589,604; Meade et al., U.S. Pat. No. 4,873,316; and Karatzas et al., U.S. Pat. No. 5,780,009), and others described in U.S. Pat. No. 5,750,172. Whey acidic protein (WAP; Genbank Accession No. X01153), the major whey protein in rodents, is expressed at high levels exclusively in the mammary gland during late pregnancy and lactation (Hobbs et al., J. Biol. Chem. 257:3598–3605, 1982). For additional information on desired mammary gland-specific promoters, see, e.g., Richards et al., J. Biol. Chem. 256:526–532, 1981 (α-lactalbumin rat); Campbell et al., Nucleic Acids Res. 12:8685–8697, 1984 (rat WAP); Jones et al., J. Biol. Chem. 260:7042–7050, 1985 (rat β-casein); Yu-Lee & Rosen, J. Biol. Chem. 258:10794–10804, 1983 (rat γ-casein); Hall, Biochem. J. 242:735–742, 1987 (human α-lactalbumin); Stewart, Nucleic Acids Res. 12:3895–3907, 1984 (bovine α-s1 and κ-casein cDNAs); Gorodetsky et al., Gene 66:87–96, 1988 (bovine β-casein); Alexander et al., Eur. J. Biochem. 178:395–401, 1988 (bovine κ-casein); Brignon et al., FEBS Lett. 188:48–55, 1977 (bovine α-S2 casein); Jamieson et al., Gene 61:85–90, 1987, Ivanov et al., Biol. Chem. Hoppe-Seyler 369:425–429, 1988, and Alexander et al., Nucleic Acids Res. 17:6739, 1989 (bovine β-lactoglobulin); and Vilotte et al., Biochimie 69:609–620, 1987 (bovine α-lactalbumin). The structure and function of the various milk protein genes are reviewed by Mercier & Vilotte, J. Dairy Sci. 76:3079–3098, 1993. If additional flanking sequences are useful in optimizing expression, such sequences can be cloned using the existing sequences as probes. Mammary-gland specific regulatory sequences from different organisms can be obtained by screening libraries from such organisms using known cognate nucleotide sequences, or antibodies to cognate proteins as probes.

Useful signal sequences for expression and secretion of ng.HuAFP into milk are milk-specific signal sequences. Desirably, the signal sequence is selected from milk-specific signal sequences, i.e., from a gene which encodes a product secreted into milk. Most desirably, the milk-specific signal sequence is related to a milk-specific promoter described above. The size of the signal sequence is not critical for this invention. All that is required is that the sequence be of a sufficient size to effect secretion of ng.HuAFP, e.g., in the mammary tissue. For example, signal sequences from genes coding for caseins, e.g., alpha, beta, gamma, or kappa caseins, beta lactoglobulin, whey acidic protein, and lactalbumin are useful in the present invention. Signal sequences from other secreted proteins, e.g., proteins secreted by liver cells, kidney cell, or pancreatic cells can also be used.

Useful promoters for the expression of a recombinant polypeptide transgene in urinary tissue are the uroplakin and uromodulin promoters (Kerr et al., Nat. Biotechnol. 16:75–79, 1998; Zbikowska, et al., Biochem. J. 365:7–11, 2002; and Zbikowski et al., Transgenic Res. 11:425–435, 2002), although any promoter that permits secretion of the transgene product into urine may be used.

A useful promoter for the expression and secretion of ng.HuAFP into blood by blood-producing or serum-producing cells (e.g., liver epithelial cells) is the albumin promoter (see, e.g., Shen et al., DNA 8:101–108, 1989; Tan et al., Dev. Biol. 146:24–37, 1991; McGrane et al., TIBS 17:40–44, 1992; Jones et al., J. Biol. Chem. 265:14684–14690, 1990; and Shimada et al., FEBS Letters 279:198–200, 1991), although any promoter that permits secretion of the transgene product into blood may be used. The native alpha-fetoprotein promoter can also be used (see, e.g., Genbank Accession Nos.: AB053574; AB053573; AB053572; AB053571; AB053570; and AB053569).

Useful promoters for the expression of ng.HuAFP in semen are described in U.S. Pat. No. 6,201,167.

Useful avian-specific promoters are the ovalbumin promoter and the apo-B promoter. Other avian-specific promoters are known in the art. The ovalbumin promoter can be used to direct expression of ng.HuAFP that is then deposited in the egg white of the egg. The apo-B promoter can also be used to direct expression of a recombinant polypeptide in the liver, where it will eventually be deposited into the egg yolk. Avian eggs are an optimal vehicle for expressing large quantities of recombinant polypeptides for the following reasons: (1) a large amount of protein is packed into each egg, (2) eggs are easy to collect non-invasively and can be stored for extended periods of time, and (3) eggs are sterile and, unlike milk, do not contain bacterial contaminants. Specifically, for each egg, a bird can produce three grams of albumin in the oviduct, of which greater than 50% is ovalbumin. Another three grams is produced in the liver (serum lipoproteins) and deposited in the egg yolk. In addition, since birds do not typically recognize mammalian proteins immunologically because of their evolutionary distance from mammals, the expression of ng.HuAFP in birds is less likely to have any deleterious effect on the viability and health of the bird.

Other promoters that are useful in the methods of the invention include inducible promoters. Generally, recombinant proteins are expressed in a constitutive manner in most eukaryotic expression systems. The addition of inducible promoters or enhancer elements provides temporal or spatial control over expression of ng.HuAFP, and provides an alternative mechanism of expression. Inducible promoters include heat shock protein, metallothionien, and MMTV-LTR, while inducible enhancer elements include those for ecdysone, muristerone A, and tetracycline/doxycycline.

The Tet-On and Tet-Off Gene Expression Systems (Clontech) is one example of an inducible system that is useful in the methods of the invention. This system uses a tetracycline (Tc) responsive element to maintain ng.HuAFP expression in either an on (constitutively off, induced with Tc) or off (constitutively on, repressed with Tc or doxycycline) mode.

Selectable markers can also be incorporated into the ng.HuAFP transgene for easy identification of cells that have been transformed. Selectable markers generally fall into two functional categories: recessive and dominant. The recessive markers are usually genes that encode products that are not produced in the host cells (cells that lack the "marker" product or function). Marker genes for thymidine kinase (TK), dihydrofolate reductase (DHFR), adenine phosphoribosyl transferase (APRT), and hypoxanthine-guanine phosphoribosyl transferase (HGPRT) are in this category. Dominant markers include genes that encode products that confer resistance to growth-suppressing compounds (antibiotics, drugs) and/or permit growth of the host cells in metabolically restrictive environments. Commonly used markers within this category include a mutant DHFR gene that confers resistance to methotrexate; the gpt gene for xanthine-guanine phosphoribosyl transferase, which permits host cell growth in mycophenolic acid/xanthine containing media; and the neo gene for aminoglycoside 3'-phosphotransferase, which can confer resistance to G418, gentamycin, kanamycin, and neomycin.

Generation of Transgenic Animals

Transgenic constructs are usually introduced into cells by microinjection (Ogata et al., U.S. Pat. No. 4,873,292). A microinjected embryo is then transferred to an appropriate female resulting in the birth of a transgenic or chimeric animal, depending upon the stage of development of the embryo when the transgene integrated. Chimeric animals can be bred to form true germline transgenic animals.

In some methods of transgenesis, transgenes are introduced into the pronuclei of fertilized oocytes. For some animals, such as mice, fertilization is performed in vivo and fertilized ova are surgically removed. In other animals, the ova can be removed from live, or from newly-dead (e.g., slaughterhouse) animals and fertilized in vitro.

Alternatively, transgenes can be introduced into embryonic stem cells (ES cells). Transgenes can be introduced into such cells by electroporation, microinjection, nuclear transfer, or any other techniques used for the transfection of cells which are known to the skilled artisan. Transformed cells are combined with blastocysts from the animal from which they originate. The transformed cells colonize the embryo, and in some embryos these cells form the germline of the resulting chimeric animal (Jaenisch, R., Science 240: 1468–1474, 1988).

ES cells containing a ng.HuAFP transgene may also be used as a source of nuclei for transplantation into an enucleated fertilized oocyte, thus giving rise to a transgenic animal. More generally, any diploid cell derived from embryonic, fetal, or adult tissue and containing a rHuAFP transgene may be introduced into an enucleated unfertilized egg. The cloned embryo is implanted and gestated within an appropriate female, thus resulting in a fully transgenic animal (Wilmut et al., Nature 385:810–813, 1997).

In general, expression of any transgene depends upon its integration position and copy number. After a transgenic animal having the appropriate transgene expression level and tissue-specific transgene expression pattern is obtained by traditional methods (e.g., pronuclear injection or generation of chimeric embryos), the animal is bred in order to obtain progeny having the same transgene expression level and pattern. There are several limitations to this approach. First, transmission of the transgene to offspring does not occur in transgenic chimeras lacking transgenic germ cells. Second, because a heterozygous transgenic founder is bred with a non-transgenic animal, only half of the progeny will be transgenic. Third, the number of transgenic progeny is further limited by the length of the gestation period and number of offspring per pregnancy. Finally, the number of useful transgenic progeny may be further limited by gender: for example, only female animals are useful for producing ng.HuAFP expressed in milk. In view of these limitations, nuclear transfer technology provides the advantage of allowing, within a relatively short time period, the generation of many female transgenic animals that are genetically identical.

Animals expressing ng.HuAFP in their milk also may be generated by direct transfer of the transgene into the mammary tissue of post-partum animals (Karatzas et al., U.S. Pat. No. 5,780,009). Such animals do not contain the transgene within their germline, and hence do not give rise to transgenic progeny.

Any animal can be usefully employed in this invention. Desirably, animals that produce large volumes of a biological fluid (e.g., milk) are preferred. Desired animals are birds, reptiles, and amphibians, as well as ruminants, ungulates, domesticated mammals, and dairy animals. Suitable birds include chickens, geese, turkeys, quail, ducks, and ostriches. Particularly desired animals include: mice, goats, sheep, camels, cows, pigs, rabbits, horses, oxen, and llamas. Of course, each of these animals may not be as effective as the others with respect to expression of ng.HuAFP. For example, a particular biological fluid-specific promoter (e.g., milk-, urine-, blood-, or lymph-specific promoter) or signal sequence may be more effective in one mammal than in others. However, one of skill in the art can easily make such choices by following the teachings of this invention and the teachings found in the prior art. Where the ng.HuAFP is secreted into the milk, urine, blood, or lymph of a transgenic animal, the animal should be able to produce at least 1 liter, more desirably at least 10, 25, or 50 liters or more, most desirably 100, 500, 1000, or 10,000 liters or more of milk, urine, blood, or lymph per year. Desirably, ng.HuAFP is recovered from a product produced by the organism, e.g., milk, urine, blood, amniotic fluid, or fluid surrounded by the yolk sac, the chorion, or the allantois of an egg, but can also be recovered from seeds, hair, tissue, or eggs.

A transgenic animal may be generated that produces ng.HuAFP in two or three biological fluids (e.g., in milk and urine, in milk and blood, or in milk, urine, and blood). One method for constructing such an animal is to transform an embryonal cell of the animal with up to three constructs, in which the constructs are selected from a ng.HuAFP nucleic acid molecule that is directed by a promoter capable of expressing and secreting the recombinant polypeptide from either a milk-producing cell, a urine-producing cell, or a blood-producing cell. In this method, the doubly- or triply-transformed cell is used to generate a transgenic animal capable of expressing ng.HuAFP in one or more of its biological fluids.

Hence, mammalian (e.g., ruminant) zygotes are microinjected (or co-microinjected) with two or three nucleic acid molecules that express ng.HuAFP under the control of one or more of, e.g., a milk-specific promoter, a urine-specific promoter, a blood-specific promoter, or a lymph-specific promoter. The generated transgenic animal will secrete/produce ng.HuAFP in one or more of its milk, urine, blood, or lymph. This will increase the total output of ng.HuAFP produced per transgenic animal unit.

A second method for producing such an animal capable of producing ng.HuAFP in one or more biological fluids is to separately generate an embryonic stem cell carrying a construct capable of expressing and secreting ng.HuAFP in a biological fluid-producing cell (e.g., a milk-producing, urine-producing, blood-producing, or lymph-producing cell). One or more of the transformed ES cell types are then combined with blastocysts from the animal from which they originated to produce chimeric animals, which may then be bred to homozygosity.

This type of double- or triple-expressing animal has a number of advantages. First, animals of both genders will produce ng.HuAFP in, e.g., the urine or blood, on a continual basis from birth, and female animals will then be able to additionally produce the ng.HuAFP in, e.g., milk, as a lactating adult. Second, the amount of ng.HuAFP produced by any individual female animal may be increased (by inducing lactation) or reduced (by not inducing lactation) as the need for the recombinant polypeptide changes.

Protocols for the production of transgenic animals can be found in, for example, White and Yannoutsos, Current Topics in Complement Research: 64th Forum in Immunology, pp. 88–94; Bader and Ganten, Clinical and Experimental Pharmacology and Physiology, Supp. 3:S81–S87, 1996; Transgenic Animal Technology, A Handbook, 1994, ed., Carl A. Pinkert, Academic Press, Inc; U.S. Pat. No. 5,523,226; U.S. Pat. No. 5,530,177; U.S. Pat. No. 5,573,933; PCT Application WO93/25071; and PCT Application WO95/04744. Other methods for making transgenic animals are known in the art (see, e.g., Love et al., Biotechnology 12:60–63, 1994; Naito et al., Mol. Reprod. Dev. 39:153–161, 1994; Chang et al., Cell Biol. Int. 21:495–499, 1997; Carscience et al., Development 117:669–675, 1993; Pain et al., Cell, Tissues, Organs 165:212–219, 1999; Pettite et al., Development 108:185–189, 1990; Pettite et al., in Transgenic Animal Research Conference III (Tahoe City), pp. 32–33, 2001; Wright et al. BioTechnology 9:830–83, 1991; Pursel et al., J. Anim. Sci. 71 Suppl 3:1–9, 1993; Wall et al., Theriogenology 5:57–968, 1996; Campbell et al., Nature 380:64–66, 1996; Wilmut et al., Nature 385:810–813, 1997; Cibelli et al., Science 280: 1256–1258, 1998; and Wakayama et al., Nature 394: 369–374, 1998).

Screening for Transgenic Animals Expressing ng.HuAFP

After the candidate transgenic animals are generated, they must be screened in order to detect animals whose cells contain and express the transgene. The presence of a transgene in animal tissues is typically detected by Southern blot analysis or by employing PCR-amplification of DNA from candidate transgenic animals (see, e.g., Ausubel et al., Current Protocols in Molecular Biology, John Wiley & Sons, New York, N.Y., 1998; see also Lubon et al., U.S. Pat. No. 5,831,141). ng.HuAFP expression in milk, urine, blood, or lymph may be determined by any standard immmunological assay, for example, ELISA or Western blotting analysis, using an antibody directed against human AFP (see, e.g., Murgita et al., U.S. Pat. No. 5,384,250 and Ausubel et al., supra). For a working example of ELISA-based detection of transgene-encoded protein in milk, see Drohan et al., U.S. Pat. No. 5,589,604.

Transgenic Plants

Any of a number of plant hosts can be used to produce ng.HuAFP using the constructs of the invention, including, without limitation, algae, tree species, ornamental species, temperate fruit species, tropical fruit species, vegetable species, legume species, crucifer species, monocots, dicots, or in any plant of commercial or agricultural significance. Particular examples of suitable plant hosts include, but are not limited to, Conifers, *Petunia*, Tomato, Potato, Tobacco, Lettuce, Sunflower, Oilseed rape, Flax, Cotton, Sugarbeet, Celery, Soybean, Alfalfa, *Lotus*, Cucumber, Carrot, Eggplant, Cauliflower, Horseradish, Morning Glory, Poplar, Walnut, Apple, Grape, *Asparagus*, Rice, *Maize*, Millet, Onion, Barley, Orchard grass, Oat, Rye, Wheat, corn, alfalfa, turgrass, aquatic plants capable of vegetative multiplication, azolla, floating rice, water hyacinth, watermelon, flowering plants that grow submerged in water, and species from the genera *Arabidopsis, Medicago, Vigna, Fragaria, Lotus, Onobrychis, Trifolium, Trigonella, Citrus, Linum, Geranium, Manihot, Daucus, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Plant extracts may be derived from any transgenic plant capable of producing ng.HuAFP. In addition, as is discussed below, transgene constructs may be expressed in a plant for the production of ng.HuAFP that can be isolated from plant tissue, or from a secretion of the plant.

Plant Promoters

Various plant promoters have been identified and isolated from different plants, as described in various patents, such as U.S. Pat. Nos. 5,391,725; 5,536,653; 5,589,583; 5,608,150; 5,898,096; 6,072,050; 6,184,440; and 6,331,663. Desired plant promoters include strong and non tissue- or developmental-specific plant promoters (e.g., a promoter that strongly expresses in many or all plant tissue types). Desired plant promoters include the Cauliflower Mosaic Virus 35S (CaMV 35S) and 19S (CaMV 19S) gene promoters, which enable expression at a high level in virtually all plant tissues (Benefey et al., Science 250:959–966, 1990; Odell et all, Nature 313:810–812, 1985; Jensen et al., Nature 321:669–674, 1986; Jefferson et al., EMBO J. 6: 3901–3907, 1987; and Sanders et al., Nuc. Acids Res. 14:1543–1558, 1987). Within the CaMV 35S promoter, expression conferred by domain A (−90 to +8) was found to be particularly strong in root tissue, whereas expression conferred by domain B (−343 to −90) appeared to be strongest in the cotyledons of seeds and seedlings and in the vascular tissue of the hypocotyl (Benfey et al., EMBO J. 8:2195–2202, 1989). Moreover, activity of this promoter can be further increased (i.e., between 2–10 fold) by duplication of the CaMV 35S promoter (see e.g., Kay et al., Science 236:1299, 1987; Ow et al., Proc. Natl. Acad. Sci., U.S.A. 84: 4870, 1987; and Fang et al., Plant Cell 1:141, 1989).

Other desirable plant promoters include, for example, the T-DNA mannopine synthetase promoter and various derivatives; an inducible promoter, such as the maize glutathione-S-transferase isoform II (GST-II-27) gene promoter, which is activated in response to application of exogenous safener (WO93/01294, ICI Ltd); the GST-II-27 gene promoter, which has been shown to be induced by certain chemical compounds which can be applied to growing plants; the dexamethasone (DEX) promoter (Aoyama et al., Plant Journal 11:605–612, 1997); an elongating tissue specific promoter (e.g., cell promoter); the chalcone synthase promoter (CHS); and the PATATIN promoter from potato (Rocha-Sosa et al., EMBO J. 8:23–29, 1989), which can be used when expression in elongating tissues and organs is desired.

Other suitable plant promoters include, for example, the nopaline synthase (NOS) and octopine synthase (OCS) promoters (which are carried on tumor inducing plasmids of *Agrobacterium tumefaciens*; Ha and An, Nucleic Acids Res. 17:215–224, 1989; and An et al., Plant Physiol. 88:547–552, 1988); the *Solanum tuberosum* leaf/stem (ST-LS)1 gene of potato (Stockhaus et al., Plant Cell 1:805–814, 1989); the soybean heat shock protein hsp17.5-E or hsp17.3-B promoters (Gurley et al., Mol. Cell Biol. 6:559–565, 1986); the *Parasponia andersoni* hemoglobin promoter (Landsmann et al., Mol. Gen. Genet. 214:68–73, 1988); the phenylalanine ammonia-lyase promoter, which appears to be active in specific cell types that accumulate phenylpropanoid derivatives in response to wounding and also during normal development of the xylem and flower (Bevan et al., EMBO J. 8:1899–1906, 1989); the *petunia* 5-enolpyruvylshikimate-3-phosphate synthase gene promoter (Benfey and Chua, Science 244:174–181, 1989); and the sucrose synthase promoter. All of these promoters have been used to create various types of DNA constructs which have been expressed in plants (see, for example, PCT publication WO84/02913).

For certain applications, it may be desirable to regulate the production of ng.HuAFP in an appropriate plant tissue, at an appropriate level, or at an appropriate developmental time. For this purpose, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Takahashi and Komeda, Mol. Gen. Genet. 219:365–372, 1989; light-regulated gene expression (e.g., the *Arabidopisis* Cab2 photosynthetic, leaf specific promoter; the maize rbcS promoter described by Schaffner and Sheen, Plant Cell 3:997–1012, 1991; the pea rbcS-3A; the light-inducible promoter from the small subunit of ribulose bisphosphate carboxylase (ss-RUBISCO, a very abundant plant polypeptide; Coruzzi et al., EMBO J. 3:1671–1679, 1984; and Herrera-Estrella et al., Nature 310:115–120, 1984); the chlorophyll a/b binding protein (Cab) of the light-harvesting chlorophyll-protein complex (Apel et al., Eur. J. Biochem. 85:581–588, 1978; Stiekema et al., Plant Physiol. 72:717–724, 1983; Thompson et al., Planta 158: 487–500, 1983; and Jones et al., EMBO J. 4:2411–2418, 1985); or the cholorphyll a/b-binding protein gene found in pea described by Simpson et al., EMBO J. 4: 2723, 1985); hormone-regulated gene expression (for example, the abscisic acid (ABA) responsive sequences from the Em gene of wheat described by Marcotte et al., Plant Cell 1: 969–976, 1989; the ABA-inducible HVA1 and HVA22, and rd29A promoters described for barley and *Arabidopsis* by Straub et al., Plant Mol. Biol. 26:617–630, 1994, Shen et al., Plant Cell 7:295–307, 1995; and wound-induced gene expression (for example, of wunI described by Siebertz et al., Plant Cell 1:961–968, 1989), organ-specific gene expression; the 23-kDa zein gene from maize; or the French bean β-phaseolin gene described by Bustos et al., *Plant Cell* 1:839–853, 1989; the vegetative storage protein promoter (soybean vspB) described by Sadka et al., Plant Cell 6:737–749, 1994), cycling promoters (e.g., the *Arabidopsis* cdc2a promoter described by Hemerly et al., Proc. Natl. Acad. Sci. USA 89:3295–3299, 1992); senescence-specific promoters (e.g., the *Arabidopsis* SAG 12 promoter described by Gan et al, Science 270:1986–1988, 1995); seed-specific promoters (for example, endosperm-specific or embryo-specific promoters); or pathogen-inducible promoters (for example, PR-1 or b-1,3 glucanase promoters).

Two other promoters that have been widely used in plant cell transformations are those of the genes encoding alcohol dehydrogenase, AdhI and AdhII. Both genes are induced after the onset of anaerobiosis. In yet another embodiment of the present invention, it may be advantageous to transform a plant with ng.HuAFP transgene construct operably linked to a modified or artificial plant promoter. Typically, such promoters, constructed by recombining structural elements of different plant promoters, have unique expression patterns and/or levels not found in natural plant promoters (see, Salina et al., Plant Cell 4:1485–1493, 1992, for examples of artificial promoters constructed by combining cis-regulatory elements with a promoter core).

Certain bacterial promoters have also been observed to be expressed in plants, including the *Rhizobium meliloti* FIXD gene promoter described in U.S. Pat. No. 4,782,022. Several promoter sequences, termed the rol A, B and C promoters, have been identified in *Agrobacterium rhizogenes* (see, e.g., Schmulling et al., Plant Cell 1:665–670, 1989; and Sugaya et al., Plant Cell Physiol. 30:649–654, 1989). The rol C promoter described by Sugaya et al., supra, located on the bacterial Ri plasmid, has been observed to be expressed in phloem cells. Other suitable promoters will be well known to those skilled in the art.

Also according to the invention, ng.HuAFP may be secreted from the expressing plant cells which is achieved by fusing the ng.HuAFP nucleic acid sequence to any suitable secretion signal peptide.

Materials for expressing the ng.HuAFP transgene constructs of the invention are available from a wide range of sources including the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.).

Methods for the generation of transgenic plants are described, e.g., in Ausubel et al., supra; Weissbach and Weissbach, Methods for Plant Molecular Biology, Academic Press, 1989; Gelvin et al., Plant Molecular Biology Manual, Kluwer Academic Publishers, 1990; Kindle, Proc. Natl. Acad. Sci., USA 87:1228–1232, 1990; Potrykus, Annu. Rev. Plant Physiol. Plant Mol. Biology 42: 205, 1991; and BioRad (Hercules, Calif.) Technical Bulletin #1687 (Biolistic Particle Delivery Systems). Expression vehicles may be chosen from those provided, e.g., in Cloning Vectors: A Laboratory Manual (Pouwels et al., 1985, Supp. 1987);

Clontech Molecular Biology Catalog (Catalog 1992/93 Tools for the Molecular Biologist, Palo Alto, Calif.); and the references cited above. Other expression constructs are described by Fraley et al. (U.S. Pat. No. 5,352,605).

A number of vectors suitable for the establishment of transgenic plants are available to the public; such vectors are described in Pouwels et al., supra, Weissbach and Weissbach, supra, and Gelvin et al., supra. These plant expression vectors can be modified for use in the invention and include (1) a nucleic acid sequence encoding ng.HuAFP, (2) a promoter (for example, one conferring inducible or constitutive, pathogen- or wound-induced, environmentally- or developmentally-regulated, or cell- or tissue-specific expression), (3) a signal sequence directing secretion of ng.HuAFP, (4) a dominant selectable marker, (5) a transcription initiation start site, (6) a ribosome binding site, (7) an RNA processing signal, (8) a transcription termination site, and/or (9) a polyadenylation signal. The promoter and signal sequence are operably linked to the ng.HuAFP nucleic acid sequence.

For applications where developmental, cell, tissue, hormonal, or environmental expression is desired, appropriate 5' upstream non-coding regions are obtained from other genes, for example, from genes regulated during meristem development, seed development, embryo development, or leaf development.

Plant expression vectors can also optionally include RNA processing signals, e.g., introns, which have been shown to be important for efficient RNA synthesis and accumulation (Callis et al., Genes and Dev. 1:1183–1200, 1987). The location of the RNA splice sequences can dramatically influence the level of ng.HuAFP transgene expression in plants. In view of this fact, an intron may be positioned upstream or downstream of the regulator encoding sequence in the ng.HuAFP transgene to modulate levels of gene expression.

In addition, the expression vectors can include 5' and 3' regulatory control sequences which are generally present in the 5' and 3' regions of plant genes (An et al., Plant Cell 1:115–122, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide BASTA® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 μg/mL (kanamycin), 20–50 μg/mL (hygromycin), or 5–10 μg/mL (bleomycin). A useful strategy for selection of transformants for herbicide resistance is described, e.g., by Vasil I. K., Cell Culture and Somatic Cell Genetics of Plants, Vol I, II, III Laboratory Procedures and Their Applications Academic Press, New York, 1984.

Plant Transformation

Upon construction of the plant expression vector, several standard methods are available for introduction of the vector into a plant host, thereby generating a transgenic plant. See, in general, Methods in Enzymology Vol. 153 ("Recombinant DNA Part D") 1987, Wu and Grossman Eds., Academic Press and European Patent Application EP 693554. These methods include (1) *Agrobacterium*-mediated transformation (*A. tumefaciens* or *A. rhizogenes*) (see, e.g., Lichtenstein and Fuller, In: Genetic Engineering, vol 6, P W J Rigby, ed, London, Academic Press, 1987; Lichtenstein, C. P., and Draper, J, In: DNA Cloning, Vol II, D. M. Glover, ed, Oxford, IRI Press, 1985; Horsch et al., Science 233:496–498, 1984; and Fraley et al., Proc. Natl. Acad. Sci. USA 80:4803, 1983); (2) the particle delivery system (see, e.g., Gordon-Kamm et al., Plant Cell 2: 603, 1990; and Klein et al., Nature 327:70–73, 1987); or BioRad Technical Bulletin 1687, supra); (3) microinjection protocols (see, e.g., Green et al., supra); (4) polyethylene glycol (PEG) procedures (see, e.g., Draper et al., Plant Cell Physiol. 23:451, 1982; Paszkowski et al., EMBO J. 3:2712–2722, 1984; and Zhang and Wu, Theor. Appl. Genet. 76:835, 1988); (5) liposome-mediated DNA uptake (see, e.g., Freeman et al., Plant Cell Physiol. 25:1353, 1984); (6) electroporation protocols (see, e.g., Gelvin et al., supra; Dekeyser et al., supra; Fromm et al., Proc. Natl. Acad Sci. USA 82:5824, 1985; Fromm et al., Nature 319: 791, 1986; Sheen, Plant Cell 2:1027, 1990; and Jang and Sheen, Plant Cell 6:1665, 1994); and (7) the vortexing method (see, e.g., Kindle, supra), and floral dip method (see, e.g., Clough and Bent, Plant J. 16:735–743, 1998). The method of transformation is not critical to the invention. Any method which provides for efficient transformation may be employed. As newer methods are available to transform crops or other host cells, they may be directly applied.

The following is an example outlining one particular technique, an *Agrobacterium*-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells is now routine practice to those skilled in the art, and has become a major tool in gene expression studies in plants and to produce improved plant varieties of agricultural or commercial interest.

Transgenic lines can be evaluated for levels of ng.HuAFP expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using specific antibodies (see, e.g., Ausubel et al., supra). In addition, in situ hybridization and immunocytochemistry according to standard protocols can be done using ng.HuAFP-specific nucleotide probes and antibodies, respectively, to localize sites of expression within transgenic tissue.

Transgenic Plant Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil et al., supra; Green et al., supra; Weissbach and Weissbach, supra; Gelvin et al., supra; Methods in Enzymology Vol. 153, Wu and Grossman Eds., Academic Press, 1987; and Methods in Enzymology, Vol. 118, Wu and Grossman Eds., Academic Press, 1987. Plant regeneration from cultural protoplasts is described in Evans et al., Handbook of Plant Cell Cultures 1: 124–176, MacMillan Publishing Co. New York, 1983; Davey, Protoplasts (1983)-Lecture Proceedings, pp. 12–29, Birkhauser, Basal, 1983; Dale, Protoplasts (1983)-Lecture Proceedings, pp. 31–41, Birkhauser, Basel, 1983; and Binding, Plant Protoplasts, pp. 21–73, CRC Press, Boca Raton, 1985.

Purification of AFP from a Biological Fluid

The ng.HuAFP may be purified from the biological fluid of a transgenic organism using standard protein purification techniques, such as affinity chromatography (see, e.g., Ausubel et al., Current Protocols in Molecular Biology, John Wiley & Sons, New York, N.Y., 1998; see also Lubon et al., U.S. Pat. No. 5,831,141) or other methods known to those skilled in the art of protein purification. Once isolated, the ng.HuAFP can, if desired, be further purified by e.g., by high performance liquid chromatography (HPLC; e.g., see Fisher, Laboratory Techniques In Biochemistry And Molecular Biology, eds. Work and Burdon, Elsevier, 1980). Following purification, the ng.HuAFP is at least 80% pure, preferably 90% pure, more preferably 95% pure, and most preferably 99% pure.

Use of ng.HuAFP Purified from the Biological Fluid of a Transgenic Organism

The ng.HuAFP that is secreted into a biological fluid (e.g., milk, urine, blood, or lymph) of a transgenic organism (e.g., a mammal) or that is purified from a biological fluid may be used as a therapeutic agent. For example, ng.HuAFP produced by the methods of the invention may be administered to a patient in need thereof to inhibit cancer cell growth, to induce bone marrow cell proliferation (for example, after a bone marrow transplant or after administration of a myelotoxic treatment such as chemotherapy or radiation treatment), or as an immunosuppressive agent (for example, to inhibit autoreactive immune cell proliferation, to inhibit rejection of a transplanted organ (e.g., graft-versus-host disease), or to treat rheumatoid arthritis, muscular dystrophy, systemic lupus erythematosus, myasthenia gravis, or insulin-dependent diabetes mellitus).

The ng.HuAFP present in or purified from a biological fluid (e.g., milk, urine, blood, or lymph) may be administered in an effective amount either alone or in combination with a pharmaceutically acceptable carrier or diluent, or in combination with other therapeutic agents by any convenient means known to skilled artisans.

Pharmaceutical formulations of a therapeutically-effective amount of ng.HuAFP, or a pharmaceutically acceptable salt-thereof, can be administered orally, parenterally (e.g., intramuscularly, intraperitoneally, intravenously, or intradermally; by subcutaneous injection; by inhalation; or through the use of optical drops or an implant), nasally, vaginally, rectally, sublingually, or topically, in admixture with a pharmaceutically acceptable carrier adapted for the route of administration. Pharmaceutical formulations containing a therapeutically-effective amount of ng.HuAFP are desirably administered subcutaneously, intramuscularly, or intravenously.

Methods well known in the art for making formulations are found, for example, in Remington's Pharmaceutical Sciences (18th edition), ed. A. Gennaro, 1990, Mack Publishing Company, Easton, Pa. Compositions intended for oral use may be prepared in solid or liquid forms according to any method known to the art for the manufacture of pharmaceutical compositions. The composition may optionally contain sweetening, flavoring, coloring, perfuming, and/or preserving agents in order to provide a more palatable preparation. Solid dosage forms for oral administration include capsules, tablets, pills, powders, and granules. In such solid forms, the ng.HuAFP is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings. Compositions intended for oral use may be prepared with an enhancer to facilitate absorption of the ng.HuAFP into the bloodstream of the recipient.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of ng.HuAFP or other active compounds in the composition. Other potentially useful parenteral delivery systems for a composition that contains ng.HuAFP include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

Compositions for rectal or vaginal administration are desirably suppositories that may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of ng.HuAFP present in the composition can be varied. One skilled in the art will appreciate that the exact individual dosages may be adjusted somewhat depending upon a variety of factors, including the time of administration, the route of administration, the nature of the formulation, the rate of excretion, the nature of the subject's conditions, and the age, weight, health, and gender of the patient. Generally, dosage levels of between 0.1 µg/kg to 100 mg/kg of body weight are administered daily as a single dose or divided into multiple doses. For most treatments, it is envisioned that a parenteral dose of between 10 µg/kg to 5.0 mg/kg of body weight will be administered once or twice per week. High dose administration (up to 5 mg/kg) for some diseases is envisioned to allow up to once a month dosing. Wide variations in the needed dosage are to be expected in view of the differing efficiencies of the various routes of administration and the disease to be treated. For instance, oral administration generally would be expected to require higher dosage levels than administration by intravenous injection. Variations in these dosage levels can be adjusted using standard empirical routines for optimization, which are well known in the art. In general, the precise therapeutically-effective dosage of ng.HuAFP will be determined by the attending physician in consideration of the above identified factors.

The ng.HuAFP can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or over-acute disorder, a treatment with an immediate release form will be desired over a prolonged release composition. Alternatively, for preventative or long-term treatments, a sustained released composition will generally be desired.

EXAMPLE

The following example is meant to illustrate the invention. It is not meant to limit the invention in any way.

Example I

Generation of Transgenic Animals Expressing Recombinant Human AFP (rHuAFP) and Non-glycosylated Human AFP (ng.HuAFP)

Materials and Methods

Recombinant DNA Procedures

Recombinant DNA procedures were performed following Sambrook, Fritsch, and Maniatis (Molecular Cloning: A Laboratory Manual, Cold Spring Harbor Laboratory, 1989). Genomic and cDNA libraries were screened with radiolabeled oligonucleotide probes derived from coding exons at the beginning (5'), middle, and end (3') of the human AFP gene (GenBank Accession #M16110). The sequences of these three probes are shown below:

```
                                         (SEQ ID NO: 18)
    AFP1:    5'-ATGAAGTGGGTGGAATCAATTTTTTTAATT-3'

(SEQ ID NO: 19)
    AFP2:    5'-ATTCATTTATGAGATAGCAAGAAGGCAT-3'

(SEQ ID NO: 20)
    AFP3:    5'-AAAAAATCATGTCCTACATATGTTCTCAA-3'
```

Human AFP Gene Cloning

The gene for human AFP spans roughly 19 kb and contains 15 exons (14 coding) separated by 14 introns. The complete sequence of the human AFP gene has been reported by Gibbs et al. (*Biochemistry* 26:1332–1343, 1987) and set forth in GenBank Accession No. M16610. The gene was initially cloned in two fragments of approximately 15 kb, which were then combined, to generate the expressed protein.

Figure 2:
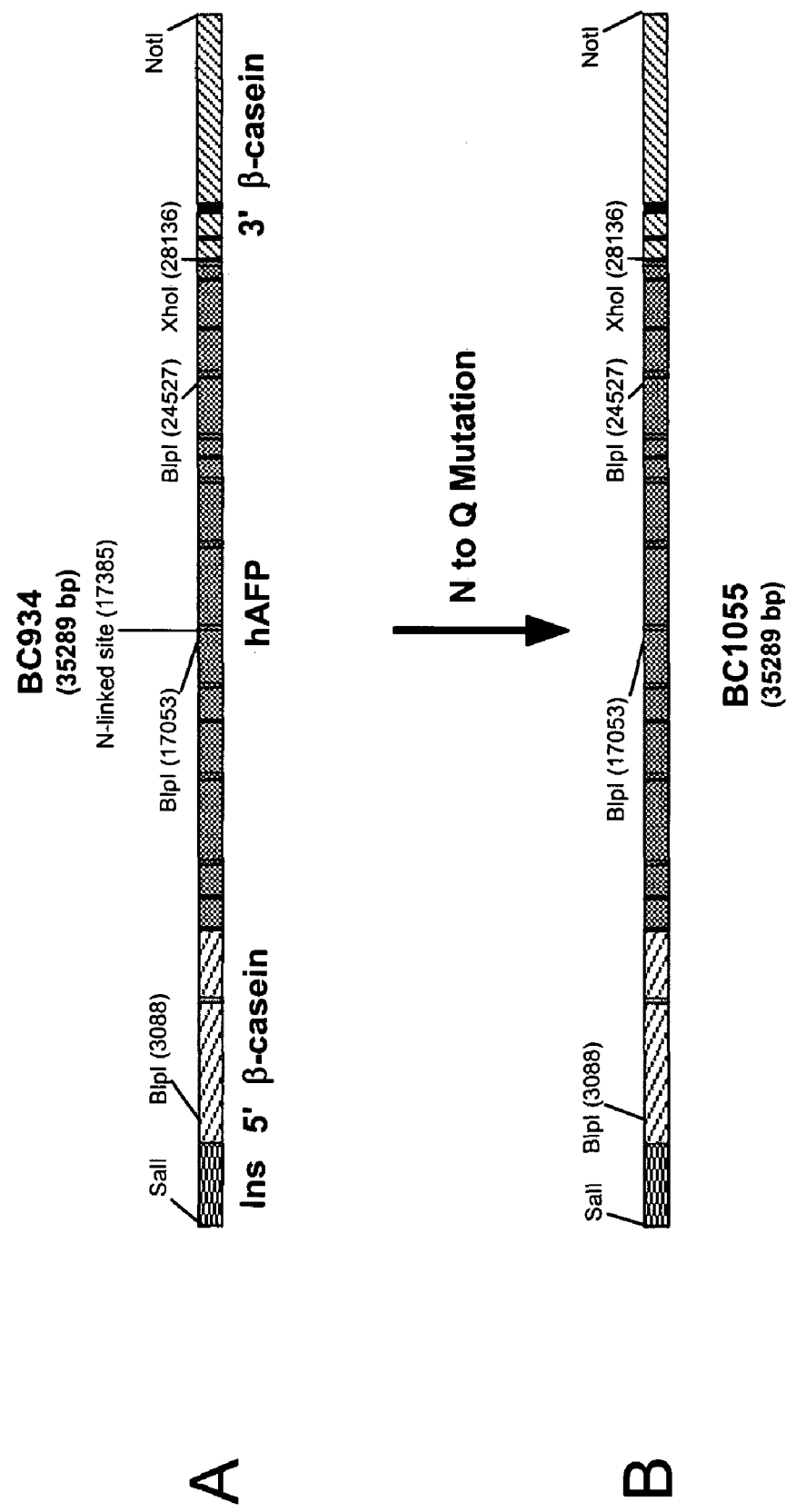
FIGS. 2A and 2B are diagrams showing the structure of a goat β-casein/rHuAFP transgene (FIG. 2A) and β-casein/ng.HuAFP transgene (FIG. 2B) for expression and secretion of rHuAFP or ng.HuAFP into milk.

A human placental genomic library (Stratagene, La Jolla, Calif.), with an average insert size of between 9 and 23 kb, was initially screened with a series of complementary oligonucleotide probes which recognize exons at the beginning, middle, and end of the human AFP gene. The first screen did not produce any positive clones. Two larger DNA probes were then made by using the polymerase chain reaction (PCR) to amplify regions of the beginning and end of the AFP gene from human genomic DNA. Subsequent screening of the library with these probes produced two overlapping lambda (λ) phage clones, of approximately 15 kb, which together span the length of the human AFP gene (FIG. 2).

A DNA fragment containing the full length coding region of human AFP and lacking the translational start sequence is obtained by performing polymerase chain reaction (PCR) amplification using a plasmid containing the HuAFP cDNA (Genbank Accession No. J00077), such as pHuAFP (described in Murgita et al., U.S. Pat. No. 5,384,250) as a template and the following oligonucleotide primers:

NH₂ (5'-AAA CTC GAG AAG TGG GTG GAA-3';   SEQ ID NO: 21) and

COOH (5'-AAA CTC GAG TTA AAC TCC CAA AGC-3';   SEQ ID NO:22).

Each PCR reaction contains 34 μl DNA template, 10 μl of 10 pmol/μl 5'-primer, 10 μl 10× reaction buffer, 20 μl 1 mM dNTPs, 2 μl DMSO and 1 μl DNA template, 10 μl of 10 pmol/μl of 10 pmol/μl 5' primer, 10 μl of 10 pmol/μl 3' primer, 1 μl glycerol, 10 μl DMSO and 1 μl Pfu DNA polymerase. Annealing, extension, and denaturation temperatures are 50° C., 72° C. and 94° C., respectively, for 30 cycles, using the Gene Amp PCR System 9600. The 1783-bp DNA obtained from the PCR reactions is digested with Xho I and then purified by isolating the fragment from a 0.7% TAE agarose gel, followed by gel extraction employing the Geneclean method (Bio 101; Vista, Calif.) according to the manufacturer's instructions.

Construction of Genomic DNA Constructs

Figure 1:
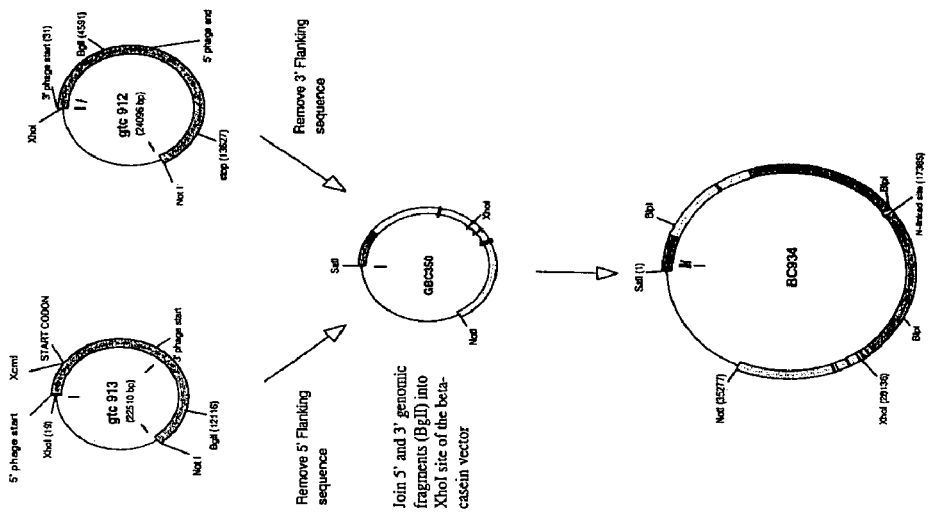
FIG. 1 is a diagram showing manipulation of vectors containing hAFP to produce the genomic hAFP β-casein expression construct BC934.

Two overlapping lambda phage clones were identified that span the length of the rHuAFP coding sequence. These phage inserts were subcloned into a supercos vector for subsequent manipulations (FIG. 1, gtc913 and gtc912). Extra sequences from the 5'-flanking region, upstream of the initiator ATG in gtc913, and extra 3'-flanking sequences downstream of the last exon in gtc912 were removed. In addition, at the 5' end, a Kozak sequence was added to ensure efficient initiation of translation. This was accomplished by inserting restriction enzyme "linkers" into the gene sequences for the subsequent excision of the appropriate sequences, leaving the flanking sequences intact (FIG. 1). Second, the 5' and 3' pieces were excised from their respective vectors using an enzyme common to the two inserts which allows them to be joined together to form the complete gene. The enzyme BglI, was used since it cuts once at the 3' end of the 5' piece and once, at the same site, at the 5' end of the 3' piece. The resulting two fragments were then joined in the β-casein expression vector (GBC350) at the XhoI site to create BC934. By separately manipulating the internal BlpI fragment of BC934, the normal glycosylation site at position 233 was changed (N to Q) through the use of gapped mutagenesis. The three BlpI fragments were then re-ligated in proper orientation to create BC1055 (FIGS. 2A and 2B).

The transgene vector (see FIG. 1; see Meade et al., U.S. Pat. No. 5,827,690) contains an altered goat β-casein gene with an Xho I site in place of the coding portion of the gene. The portion deleted from the goat β-casein gene extends from the Taq I site in exon 2 to the Ppu MI site in exon 7. Exon 2 contains the translational start codon in addition to a 15 amino acid secretion signal. To generate the goat β-casein/human AFP transgene, the Xho I/Xho I HuAFP cDNA is ligated between exons 2 and 7 of the goat β-casein gene at the Xho I site. The complete transgene contains 6.2 kb of 5' goat β-casein sequence, the 1.8 kb HuAFP cDNA, and the 7.1 kb 3' goat β-casein flanking sequence.

Preparation of DNA for Microinjection and Transfection

Transgene DNA was separated from the vector backbone by digesting the plasmid to completion with SalI and NotI (New England Biolabs, Beverly, Mass.). Digests were then electrophoresed in an agarose gel, using 1× TAE (Maniatis et. al., 1982) as running buffer. The region of the gel containing the DNA fragment corresponding to the expression cassette was visualized under UV light (long wave). The band containing the DNA of interest was excised, and the DNA isolated by electro-elution in 1× TAE. This procedure was applied for each expression cassette.

Following electro-elution, DNA fragments were concentrated and further purified. The final elution was performed using 125 μL of microinjection buffer (10 mM Tris pH 7.5, 0.2 mM EDTA). The stock solution aliquots for microinjection were diluted in microinjection buffer just prior to microinjection so that the final concentration of each fragment was 0.5 ng/mL.

Transgenic Mouse Generation: Embryo Collection, Nuclear Transfer, and Embryo Transfer For nuclear transfer, somatic cells were isolated from either fetal tissues or skin biopsies, transduced, and further characterized as described above. The transduced and characterized somatic cells containing the rHuAFP or ng.HuAFP constructs were placed into culture for use in the nuclear transfer procedure. The male pronuclei were microinjected with DNA diluted in microinjection buffer.

CD1 female mice were superovulated and fertilized ova were retrieved from the oviduct. The retrieved oocytes were enucleated through mechanical removal of the metaphase plate of the MII oocyte. The enucleated oocytes (cytoplast) were then reconstructed with an individually isolated transduced somatic cell (karyoplast). Once reconstructed, the couplet (enucleated oocyte and somatic cell) was fused together by an electrical pulse which simultaneously activated the reconstructed embryo. The activated embryo was then placed into culture. The reconstructed embryo was then maintained in culture for 24–48 hours (in CZB media) and assessed for embryo viability and development prior to embryo transfer, or were transferred immediately into the oviduct of pseudo-pregnant recipient CD1 female mice.

Following the nuclear transfer procedure and embryo culture, viable and developing embryos were transferred to suitable recipient animals. Twenty to thirty 2-cell or forty to fifty 1-cell embryos were transferred to each recipient female into the oviduct, ipsilateral to a CL, in a small volume of media by precise cannulation of the oviduct with a glass pipette, and allowed to proceed to term.

Identification of Founder Animals

Genomic DNA was isolated from mouse tail tissue by proteinase K digestion followed by NaCl extraction and ethanol precipitation and analyzed by polymerase chain reaction (PCR) to detect the β-casein/alpha-fetoprotein junction DNA sequences present only in the transgenes. Goat ear tissue and white blood cells were processed in a similar way but DNA was extracted successively with saturated phenol, phenol:isoamyl alcohol, and chloroform before ethanol precipitation. For the PCR reactions, approximately 250 ng of genomic DNA was diluted in 50 mL of PCR buffer (20 mM Tris pH 8.3, 50 mM KCl, and 1.5 mM MgCl₂, 100 mM deoxynucleotide triphosphates, and each primer at a concentration of 600 nM) with 1.0 unit of Taq polymerase, and amplified in a MJ Research DNA Engine using standard PCR cycling conditions. The following primers were used in the PCR reactions:

```
Oligo GTC17
GATTGACAAGTAATACGCTGTTTCCTC;        (SEQ ID NO: 23)

Oligo AFP-PCR3
TTTGTAAACCTCTTGTAAAGTTACAAG;        (SEQ ID NO: 24)

Oligo GEX7F
CCAGGCACAGTCTCTAGTCTA;              (SEQ ID NO: 25)

Oligo GEX7R
GGACAGGACCAAGTACAGGCT.              (SEQ ID NO: 26)
```

Southern Blot Analysis

Five µg genomic DNA was digested with 100 units EcoRI followed by electrophoresis through a 0.8% agarose gel. The gel was then blotted to a charged Nylon membrane (Genescreen Plus, New England Nuclear) by capillary action in 0.4N NaOH and UV crosslinked (Stratalinker, Sratagene). After prehybridization in hybridization buffer (5×SSC, 50% formamide, 10% dextran sulfate, 20 mM sodium phosphate, 1× Denhardt's, 0.5% SDS) containing 20 µg/mL denatured herring sperm DNA, probe was added and the blot incubated overnight at 42° C. Blots were washed as follows: one time in 1×SSC, 1% SDS at room temperature for 20 minutes, one time in 0.5×SSC, 0.5×SDS at room temperature for 20 minutes, and three times in 0.1×SSC, 0.1% SDS at 65° C. for 20 minutes each time. Following the washes, the blots were autoradiographed.

Western Blotting

The immunoblotting procedures of Harlow and Lane (Antibodies: A Laboratory Manual, Cold Spring Laboratory, 1988) were used for the immuno-detection of proteins. Milk samples were diluted 1:20 in PBS, then mixed 1:1 with 2×SDS gel loading buffer (50 mM Tris HCl, pH 6.8, 2% SDS, 10% glycerol, 10% β-mercaptoethanol), heated at 65° C. for two minutes, and subjected to SDS-PAGE. The proteins in the gel were transferred onto Immobilon P membranes in transfer buffer (50 mM Tris, 380 mM glycine, 0.1% SDS, 20% methanol) by electroblotting. For immunostaining, the membrane was incubated with a blocking buffer (4% Non-fat Dry Milk, BioRad, Hercules, Calif., in PBS containing 0.01%Tween-20) at room temperature (RT) for 1 hour. Membranes were then incubated with the anti-hAFP antibody (1:5000 in blocking buffer) for 1 hour at RT. Following three short washes in dH$_2$O, membranes were incubated with the secondary antibody (1:10000 in blocking buffer) for 1 hour at RT. Membranes were then washed three times in dH$_2$O for 4 min. each, one time in PBS/Tween-20, and finally, six more times in dH$_2$O before development with the chemiluminescent substrate (ECL) followed by autofluorography.

Analysis of Transgenic Mice Derived from Genomic DNA Constructs

Figure 3:
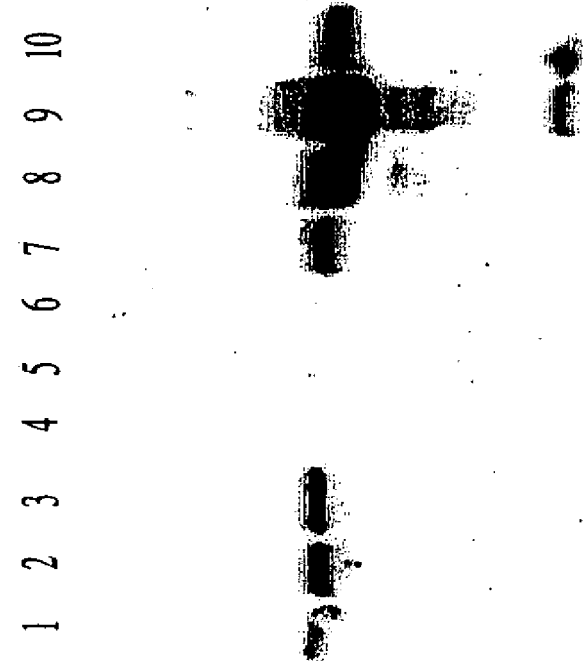
FIG. 3 is an image of a Western blot showing the presence of rHuAFP in transgenic mouse milk samples. Lanes 1–3: hAFP. Lane 1: 50 ng HAFP (0.5 mg/mL equivalent); Lane 2: 100 ng hAFP (1.0 mg/mL equiv.); Lane 3: 200 ng hAFP (2.0 mg/mL equiv.); Lane 4: Negative (nontransgenic) mouse milk; Lanes 5–10: rHuAFP. Lane 5: BC934-1-7, d9, (4 µL-1:40); Lane 6: BC934-1-8, d9, (4 µL-1:40); lane 7: BC934-1-56, d9, (4 µL-1:40); Lane 8: BC934-1-59, d9, (4

Transgenic female mice derived from the genomic construct, BC1055 were identified by PCR and are listed in Table I. Milk from these animals was analyzed by Western blot and expression levels were estimated by comparison to hAFP standards of known concentration. Results of this expression analysis are shown in Table I and II and in FIGS. 3 (rHuAFP) and 4 (ng.HuAFP). Expression analysis is normally carried out on second-generation females of the original founder animals to test for transmission of the transgene and mosaicism. Reduced levels of expression in the second generation is thought to be due to the segregation of multiple transgene integration sites with the lower expressing site in these cases passed on to the next generation.

TABLE I

Mouse Milk Expression Results - BC934 Construct

| 1$^{st}$ Generation Mouse ID # | 2$^{nd}$ Generation Mouse ID # | Expression Level (mg/mL) |
| --- | --- | --- |
| 8F | | <1 |
| 56F | | 1 |
| 59F | | 2–4 |
| 63F | | 10–20 |
| 64F | | 4 |
| 98F | | <1 |
| 130F | | <1 |
| 134F | | 20 |
| 141F | | 10 |
| 175F | | <1 |
| 185F | | <1 |
| 204F | | 5 |

TABLE II

Mouse Milk Expression Results - BC1055 Construct

| 1$^{st}$ Generation Mouse ID # | 2$^{nd}$ Generation Mouse ID # | Expression Level (mg/mL) |
| --- | --- | --- |
| 9F | | 1 |
| 10F | | 10 |
| | 109 | 2 |
| | 110 | 2 |
| | 111 | 1 |
| | 112 | 1 |
| 37F | | 10–20 |
| | 116 | 2 |
| | 118 | 5 |
| 44 | | <1 |
| | 120 | 4 |
| | 121 | 4 |
| 74F | | 2 |
| | 129 | 1 |
| 85F | | 1 |

Isolation of Goat Fetal Fibroblasts and Transfection of the ng.HuAFP Transgene

Goat fetal fibroblast cells were isolated from goat fetal tissue from pregnant goats (Genzyme Transgenic Corporation). The DNA fragments of the ng.HuAFP transgene (BC1055) and neomycin resistance gene were prepared, and co-transduced into the goat fetal fibroblasts using LipofectAmine at 1–2 µg of transgene DNA fragments/10$^6$ cells. Colonies of neomycin-resistant cells were isolated following G418 selection. Isolated clones were expanded and selected cell lines were cryo-preserved. These cell lines were subjected to PCR analysis using BC1055 specific primers to determine the presence of the transgene. In addition, FISH analysis of the cell lines was carried out to confirm the integration of the transgenes (see below).

Generation of Trangenic Founder Goats

Transgenic goats were generated by injecting, into the pronucleus of collected embryos, the 15.1 kb fragment of the goat β-casein-HuAFP purified free from prokaryotic DNA at a concentration of 1.0 µg/ml in 10 mM Tris, pH 7.5, 0.1 mM EDTA. Injected embryos were then transferred to recipient females. A founder (F$_o$) transgenic goat was identified by analyzing genomic DNA from blood by polymerase chain reaction (PCR) and by Southern blot analysis in order to detect the presence of the transgene. For PCR analysis, the same two oligonucleotides that were employed to generate the HuAFP cDNA were used in the reaction. For Southern blot analysis, the DNA was fractionated on a 1% TBE agarose gel, blotted onto nitrocellulose, and probed with a random-primed $^{32}$P-labelled 1.8 kb HuAFP cDNA. The identified founder can now be bred to a nontransgenic animal to produce transgenic offspring. Alternatively, transgenic offspring may be obtained by nuclear transfer, as described above. Transmission of the transgene can be detected by analyzing genomic DNA from blood and other tissues as described above.

Genetic Analysis of Founder Goat F093

A healthy female goat (F093) was born Mar. 11, 2002. To determine if this goat carries the ng.HuAFP transgene, PCR analysis of blood and ear tissue was performed. Initially, two PCR primer pairs were used at the same time. The first pair, as is shown in the diagram in FIG. 5, is specific to the transgene, and the resultant 332 bp product spans the junction of the 5' β-casein and the 5' ng.HuAFP sequences. The second primer pair recognizes goat β-casein exon seven which is not present in the transgene construct and gives a product of 439 bp. FIGS. 6A and 6B shows that the ng.HuAFP transgene is present in goat F093, in both the blood and ear samples. A transduced cell line that had been characterized earlier was used as a positive control. Ear tissue from an abortus that had been shown to carry the ng.HuAFP transgene was also used as a positive control.

After confirming the genotype, Southern Blot Analysis was performed to estimate copy number and rule out gross transgene rearrangements (FIG. 7). The DNA probe used was a XhoI/HindIII fragment of the 3' β-casein gene (FIG. 2, 3' BC probe) found in the transgene and the endogenous goat β-casein gene. By comparing the relative intensities of the transgene and the endogenous gene, one can estimate the transgene copy number. The endogenous gene signal represents two copies of the gene in a diploid genome. As can be seen in FIG. 7, the two bands in the F093 sample appear quite similar in intensity. Scanning densitometry (Molecular Dynamics) confirms a one-to-one ratio (the F026 abortus has a 13:1 ratio by densitometry).

Fluorescence In Situ Hybridization (FISH) Analysis

Standard culture and preparation procedures were used to obtain metaphase and interphase nuclei from cultured blood lymphocytes from goat F093. Nuclei were deposited onto slides and were hybridized with a digoxigenin-labeled probe derived from a construct containing 8 kb of the genomic sequence for human AFP. Bound probe was amplified using a horseradish peroxidase-conjugated antibody and detected with tyramide-conjugated fluorescein isothiocyanate (FITC, green fluorochrome). Nuclei were counterstained with 4',6-diamidino-2-phenylindole (DAPI, blue dye). FISH images were obtained using MetaMorph software.

Figure 8:
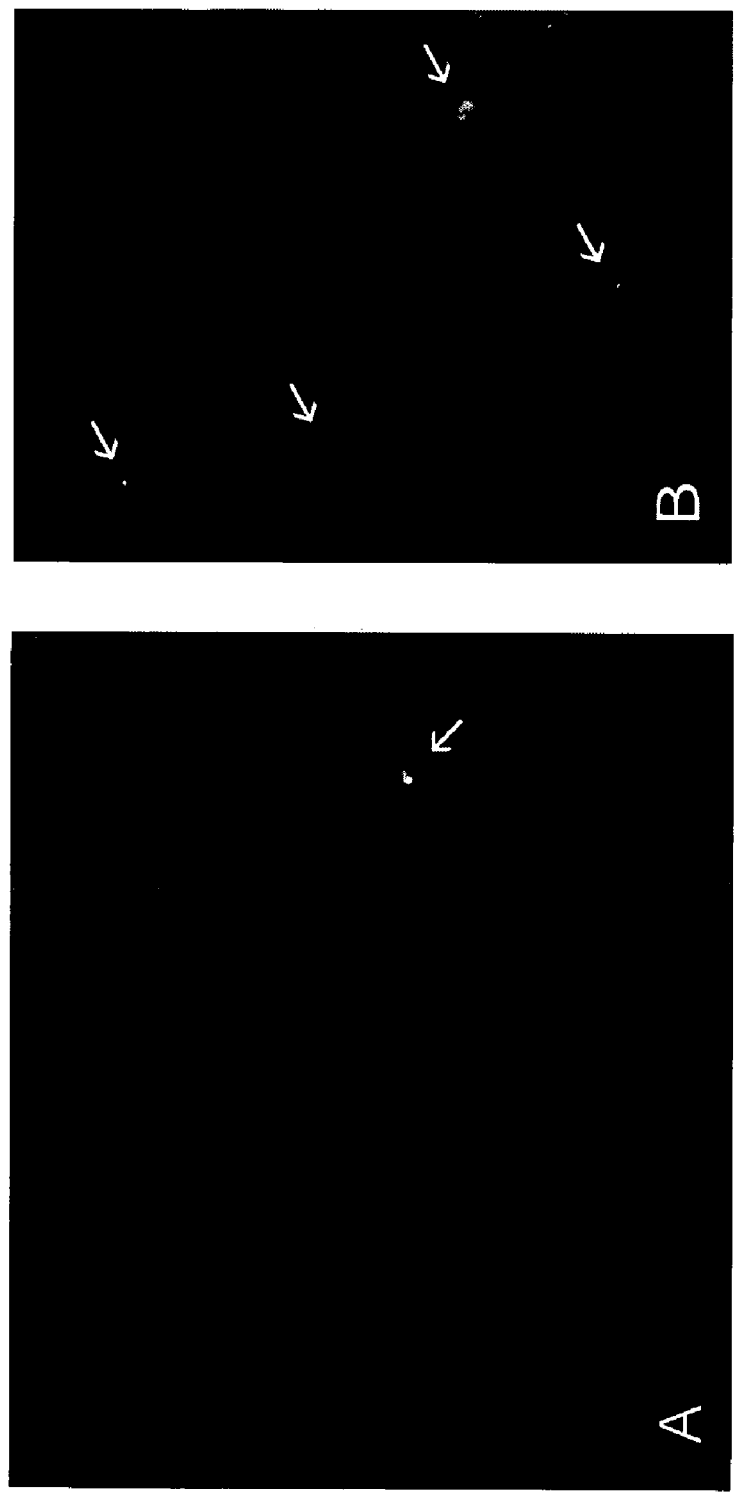

FISH images of metaphase chromosomes and interphase nuclei showing the transgene are shown in FIG. 8. The transgene signal is located towards the "q" terminal end on a mid to large sized autosomal chromosome. FISH analysis is consistent with the existence of a single transgene integration site.

Lactation Induction

Female animals twelve months of age or older are induced to lactate by hormone therapy and hand stimulation over a 12 day period. During the first 4 days, the animal receive subcutaneous injections of 0.1 mg/kg of estradiol 17-β and 0.25 mg/kg of progesterone dissolved in 100% ethanol. This daily amount is divided between morning and evening injections. The udder is palpated once daily and the teats are hand-stimulated for 5–10 minutes each morning. Lactating transgenic females are milked manually twice per day and the milk is stored frozen at −20° C.

Protein Purification

Transgenic goat milk containing rHuAFP or ng.HuAFP is clarified by tangential flow filtration to remove casein micelles and other contaminating proteins. The resultant filtrate (whey fraction) containing the rHuAFP or ng.HuAFP is filtered through a 22 μm filter. The pH and ionic strength are adjusted by adding an equal volume of 20 mM imidazole, pH 6.7, and the rHuAFP or ng.HuAFP is purified from the whey fraction by passing the solution through a column containing Pharmacia Blue SEPHAROSE® 6 Fast flow beads equilibrated with 20 mM imidazole, pH 6.7. The rHuAFP or ng.HuAFP in the flow through is captured with a column containing Pharmacia Q HP beads equilibrated with 20 mM Imidazole pH 6.7. The rHuAFP or ng.HuAFP is eluted with a gradient of 0 to 250 mM NaCl in 20 mM imidazole, pH 6.7. Fractions containing rHuAFP or ng.HuAFP, determined by western blot, ELISA, or Coomassie-stained SDS-PAGE gel, are pooled, and the NaCl concentration is adjusted to. 725 mM. These pooled fractions are then applied to a column containing Pharmacia Phenyl HiSub beads equilibrated with 1 M NaCl, 20 mM imidazole, pH 6.7. The rHuAFP or ng.HuAFP is eluted with a gradient of 1 to 10 mM NaCl in 20 mM Imidazole, pH 6.7. Fractions containing rHuAFP or ng.HuAFP, determined by western blot, ELISA, or Coomassie-stained SDS-PAGE gel, are pooled and concentrated by ultrafiltration.

Final purification of rHuAFP or ng.HuAFP is achieved by applying the concentrated sample onto a SUPERDEX® 200 HR column equilibrated in phosphate buffered saline. Fractions containing rHuAFP or ng.HuAFP, determined by western blot, ELISA, or Coomassie-stained SDS-PAGE gel, are pooled.

The results presented above demonstrate that recombinant native human AFP, as well as a recombinant non-glycosylated form of human alpha-fetoprotein (ng.HuAFP) were cloned and expressed in the milk of several lines of transgenic mice as a genomic "mini-gene." The expression of this gene is under the control of goat β-casein regulatory elements. Expression levels in non-mosaic mice (mice able to pass the transgene on to subsequent generations) ranged from 1.0 to 20 mg/mL. As predicted from previous studies, the genomic expression constructs appear to give higher levels of ng.HuAFP expression, though ng.HuAFP expression was also quite high (5–10 mg/mL) in the animals derived from cDNA constructs. The transgene products from all constructs were immunoreactive with a hAFP-specific antibody.

We have also generated a founder transgenic goat bearing the same genomic transgene used to express high levels of ng.HuAFP in mice. Genetic analysis of several tissues from this goat, F093, confirms that she is indeed transgenic and harbors approximately two copies of the ng.HuAFP transgene in a single integration site.

OTHER EMBODIMENTS

The publications listed hereafter describe the generation, detection, and analysis of transgenic animals that secrete recombinant proteins into milk, as well as purification of the recombinant proteins. These publications are herein incorporated by reference: Hurwitz et al., U.S. Pat. No. 5,648,243

(goats); Meade, et al., U.S. Pat. No. 5,827,690 (goats); DiTulio et al., U.S. Pat. No. 5,843,705 (goats); Clark et al., U.S. Pat. No. 5,322,775 (sheep); Garner et al., U.S. Pat. No. 5,639,940 (sheep); Deboer et al., U.S. Pat. No. 5,633,076 (cows); and Drohan et al., U.S. Pat. No. 5,589,604 (pigs and mice). Kerr et al., Nat. Biotechnol. 16:75–79, 1998, herein incorporated by reference, describes the generation and analysis of transgenic animals that excrete recombinant proteins into urine, as well as purification of the recombinant proteins.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. Non-glycosylated HuAFP (ng.HuAFP) comprising a glutamine residue at position 233 of SEQ ID NO: 4.

2. A polypeptide comprising the amino acid sequence set forth in SEQ ID NO: 6, wherein said polypeptide comprises a glutamine residue at position 251.

3. A substantially pure biologically-active fragment of non-glycosylated human alpha-fetoprotein, wherein said fragment comprises the amino acid sequence set forth in SEQ ID NO: 15 (Domain II), SEQ ID NO: 16 (Domain I+II), or SEQ ID NO: 17 (Domain I+III), or two or more of said amino acid sequences.

* * * * *

SEQUENCE LISTING

```
<160> NUMBER OF SEQ ID NOS: 26

<210> SEQ ID NO 1
<211> LENGTH: 2027
<212> TYPE: DNA
<213> ORGANISM: Homo sapiens
<220> FEATURE:
<221> NAME/KEY: CDS
<222> LOCATION: (45)...(1874)

<400> SEQUENCE: 1
atattgtgct tccaccactg ccaataacaa ataactagc aacc atg aag tgg gtg        56
                                              Met Lys Trp Val
                                                1 gaa tca att ttt tta att ttc cta cta aat ttt act gaa tcc aga aca       104
Glu Ser Ile Phe Leu Ile Phe Leu Leu Asn Phe Thr Glu Ser Arg Thr
  5                  10                  15                  20 ctg cat aga aat gaa tat gga ata gct tcc ata ttg gat tct tac caa       152
Leu His Arg Asn Glu Tyr Gly Ile Ala Ser Ile Leu Asp Ser Tyr Gln
                 25                  30                  35 tgt act gca gag ata agt tta gct gac ctg gct acc ata ttt ttt gcc       200
Cys Thr Ala Glu Ile Ser Leu Ala Asp Leu Ala Thr Ile Phe Phe Ala
             40                  45                  50 cag ttt gtt caa gaa gcc act tac aag gaa gta agc aaa atg gtg aaa       248
Gln Phe Val Gln Glu Ala Thr Tyr Lys Glu Val Ser Lys Met Val Lys
         55                  60                  65 gat gca ttg act gca att gag aaa ccc act gga gat gaa cag tct tca       296
Asp Ala Leu Thr Ala Ile Glu Lys Pro Thr Gly Asp Glu Gln Ser Ser
     70                  75                  80 ggg tgt tta gaa aac cag cta cct gcc ttt ctg gaa gaa ctt tgc cat       344
Gly Cys Leu Glu Asn Gln Leu Pro Ala Phe Leu Glu Glu Leu Cys His
 85                  90                  95                 100 gag aaa gaa att ttg gag aag tac gga cat tca gac tgc tgc agc caa       392
Glu Lys Glu Ile Leu Glu Lys Tyr Gly His Ser Asp Cys Cys Ser Gln
                105                 110                 115 agt gaa gag gga aga cat aac tgt ttt ctt gca cac aaa aag ccc act       440
Ser Glu Glu Gly Arg His Asn Cys Phe Leu Ala His Lys Lys Pro Thr
            120                 125                 130 cca gca tcg atc cca ctt ttc caa gtt cca gaa cct gtc aca agc tgt       488
Pro Ala Ser Ile Pro Leu Phe Gln Val Pro Glu Pro Val Thr Ser Cys
        135                 140                 145 gaa gca tat gaa gaa gac agg gag aca ttc atg aac aaa ttc att tat       536
Glu Ala Tyr Glu Glu Asp Arg Glu Thr Phe Met Asn Lys Phe Ile Tyr
    150                 155                 160 gag ata gca aga agg cat ccc ttc ctg tat gca cct aca att ctt ctt       584
Glu Ile Ala Arg Arg His Pro Phe Leu Tyr Ala Pro Thr Ile Leu Leu
165                 170                 175                 180
```

```
tgg gct gct cgc tat gac aaa ata att cca tct tgc tgc aaa gct gaa      632
Trp Ala Ala Arg Tyr Asp Lys Ile Ile Pro Ser Cys Cys Lys Ala Glu
                185                 190                 195 aat gca gtt gaa tgc ttc caa aca aag gca gca aca gtt aca aaa gaa      680
Asn Ala Val Glu Cys Phe Gln Thr Lys Ala Ala Thr Val Thr Lys Glu
        200                 205                 210 tta aga gaa agc agc ttg tta aat caa cat gca tgt gca gta atg aaa      728
Leu Arg Glu Ser Ser Leu Leu Asn Gln His Ala Cys Ala Val Met Lys
            215                 220                 225 aat ttt ggg acc cga act ttc caa gcc ata act gtt act aaa ctg agt      776
Asn Phe Gly Thr Arg Thr Phe Gln Ala Ile Thr Val Thr Lys Leu Ser
230                 235                 240 cag aag ttt acc aaa gtt aat ttt act gaa atc cag aaa cta gtc ctg      824
Gln Lys Phe Thr Lys Val Asn Phe Thr Glu Ile Gln Lys Leu Val Leu
245                 250                 255                 260 gat gtg gcc cat gta cat gag cac tgt tgc aga gga gat gtg ctg gat      872
Asp Val Ala His Val His Glu His Cys Cys Arg Gly Asp Val Leu Asp
                265                 270                 275 tgt ctg cag gat ggg gaa aaa atc atg tcc tac ata tgt tct caa caa      920
Cys Leu Gln Asp Gly Glu Lys Ile Met Ser Tyr Ile Cys Ser Gln Gln
            280                 285                 290 gac act ctg tca aac aaa ata aca gaa tgc tgc aaa ctg acc acg ctg      968
Asp Thr Leu Ser Asn Lys Ile Thr Glu Cys Cys Lys Leu Thr Thr Leu
        295                 300                 305 gaa cgt ggt caa tgt ata att cat gca gaa aat gat gaa aaa cct gaa      1016
Glu Arg Gly Gln Cys Ile Ile His Ala Glu Asn Asp Glu Lys Pro Glu
    310                 315                 320 ggt cta tct cca aat cta aac agg ttt tta gga gat aga gat ttt aac      1064
Gly Leu Ser Pro Asn Leu Asn Arg Phe Leu Gly Asp Arg Asp Phe Asn
325                 330                 335                 340 caa ttt tct tca ggg gaa aaa aat atc ttc ttg gca agt ttt gtt cat      1112
Gln Phe Ser Ser Gly Glu Lys Asn Ile Phe Leu Ala Ser Phe Val His
                345                 350                 355 gaa tat tca aga aga cat cct cag ctt gct gtc tca gta att cta aga      1160
Glu Tyr Ser Arg Arg His Pro Gln Leu Ala Val Ser Val Ile Leu Arg
            360                 365                 370 gtt gct aaa gga tac cag gag tta ttg gag aag tgt ttc cag act gaa      1208
Val Ala Lys Gly Tyr Gln Glu Leu Leu Glu Lys Cys Phe Gln Thr Glu
        375                 380                 385 aac cct ctt gaa tgc caa gat aaa gga gaa gaa gaa tta cag aaa tac      1256
Asn Pro Leu Glu Cys Gln Asp Lys Gly Glu Glu Glu Leu Gln Lys Tyr
    390                 395                 400 atc cag gag agc caa gca ttg gca aag cga agc tgc ggc ctc ttc cag      1304
Ile Gln Glu Ser Gln Ala Leu Ala Lys Arg Ser Cys Gly Leu Phe Gln
405                 410                 415                 420 aaa cta gga gaa tat tac tta caa aat gcg ttt ctc gtt gct tac aca      1352
Lys Leu Gly Glu Tyr Tyr Leu Gln Asn Ala Phe Leu Val Ala Tyr Thr
                425                 430                 435 aag aaa gcc ccc cag ctg acc tcg tcg gag ctg atg gcc atc acc aga      1400
Lys Lys Ala Pro Gln Leu Thr Ser Ser Glu Leu Met Ala Ile Thr Arg
            440                 445                 450 aaa atg gca gcc aca gca gcc act tgt tgc caa ctc agt gag gac aaa      1448
Lys Met Ala Ala Thr Ala Ala Thr Cys Cys Gln Leu Ser Glu Asp Lys
        455                 460                 465 cta ttg gcc tgt ggc gag gga gcg gct gac att att atc gga cac tta      1496
Leu Leu Ala Cys Gly Glu Gly Ala Ala Asp Ile Ile Ile Gly His Leu
    470                 475                 480 tgt atc aga cat gaa atg act cca gta aac cct ggt gtt ggc cag tgc      1544
Cys Ile Arg His Glu Met Thr Pro Val Asn Pro Gly Val Gly Gln Cys
485                 490                 495                 500
```

```
tgc act tct tca tat gcc aac agg agg cca tgc ttc agc agc ttg gtg    1592
Cys Thr Ser Ser Tyr Ala Asn Arg Arg Pro Cys Phe Ser Ser Leu Val
                505                 510                 515 gtg gat gaa aca tat gtc cct cct gca ttc tct gat gac aag ttc att    1640
Val Asp Glu Thr Tyr Val Pro Pro Ala Phe Ser Asp Asp Lys Phe Ile
        520                 525                 530 ttc cat aag gat ctg tgc caa gct cag ggt gta gcg ctg caa acg atg    1688
Phe His Lys Asp Leu Cys Gln Ala Gln Gly Val Ala Leu Gln Thr Met
            535                 540                 545 aag caa gag ttt ctc att aac ctt gtg aag caa aag cca caa ata aca    1736
Lys Gln Glu Phe Leu Ile Asn Leu Val Lys Gln Lys Pro Gln Ile Thr
550                 555                 560 gag gaa caa ctt gag gct gtc att gca gat ttc tca ggc ctg ttg gag    1784
Glu Glu Gln Leu Glu Ala Val Ile Ala Asp Phe Ser Gly Leu Leu Glu
565                 570                 575                 580 aaa tgc tgc caa ggc cag gaa cag gaa gtc tgc ttt gct gaa gag gga    1832
Lys Cys Cys Gln Gly Gln Glu Gln Glu Val Cys Phe Ala Glu Glu Gly
            585                 590                 595 caa aaa ctg att tca aaa act cgt gct gct ttg gga gtt taa            1874
Gln Lys Leu Ile Ser Lys Thr Arg Ala Ala Leu Gly Val *
        600                 605 attacttcag gggaagagaa gacaaaacga gtctttcatt cggtgtgaac ttttctcttt  1934
aattttaact gatttaacac tttttgtgaa ttaatgaaat gataaagact tttatgtgag  1994
atttccttat cacagaaata aaatatctcc aaa                              2027

<210> SEQ ID NO 2
<211> LENGTH: 609
<212> TYPE: PRT
<213> ORGANISM: Homo sapiens

<400> SEQUENCE: 2

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190
```

```
Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
        210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
            245                 250                 255

Lys Leu Val Leu Asp Val Ala His Val His Glu His Cys Cys Arg Gly
                260                 265                 270

Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
        290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
        370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Thr Cys Cys Gln Leu
        450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
            485                 490                 495

Val Gly Gln Cys Cys Thr Ser Ser Tyr Ala Asn Arg Arg Pro Cys Phe
        500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
        530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
            565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val
```

-continued

```
<210> SEQ ID NO 3
<211> LENGTH: 1776
<212> TYPE: DNA
<213> ORGANISM: Homo sapiens
<220> FEATURE:
<221> NAME/KEY: CDS
<222> LOCATION: (1)...(1776)

<400> SEQUENCE: 3
```

| | | | | | | | | | | | | | | | | |
|---|---|---|---|---|---|---|---|---|---|---|---|---|---|---|---|---|
| aga | aca | ctg | cat | aga | aat | gaa | tat | gga | ata | gct | tcc | ata | ttg | gat | tct | 48 |
| Arg | Thr | Leu | His | Arg | Asn | Glu | Tyr | Gly | Ile | Ala | Ser | Ile | Leu | Asp | Ser | |
| 1 | | | | 5 | | | | | 10 | | | | | 15 | | |
| tac | caa | tgt | act | gca | gag | ata | agt | tta | gct | gac | ctg | gct | acc | ata | ttt | 96 |
| Tyr | Gln | Cys | Thr | Ala | Glu | Ile | Ser | Leu | Ala | Asp | Leu | Ala | Thr | Ile | Phe | |
| | | 20 | | | | | 25 | | | | | 30 | | | | |
| ttt | gcc | cag | ttt | gtt | caa | gaa | gcc | act | tac | aag | gaa | gta | agc | aaa | atg | 144 |
| Phe | Ala | Gln | Phe | Val | Gln | Glu | Ala | Thr | Tyr | Lys | Glu | Val | Ser | Lys | Met | |
| | 35 | | | | | 40 | | | | | 45 | | | | | |
| gtg | aaa | gat | gca | ttg | act | gca | att | gag | aaa | ccc | act | gga | gat | gaa | cag | 192 |
| Val | Lys | Asp | Ala | Leu | Thr | Ala | Ile | Glu | Lys | Pro | Thr | Gly | Asp | Glu | Gln | |
| 50 | | | | | 55 | | | | | 60 | | | | | | |
| tct | tca | ggg | tgt | tta | gaa | aac | cag | cta | cct | gcc | ttt | ctg | gaa | gaa | ctt | 240 |
| Ser | Ser | Gly | Cys | Leu | Glu | Asn | Gln | Leu | Pro | Ala | Phe | Leu | Glu | Glu | Leu | |
| 65 | | | | 70 | | | | | 75 | | | | | 80 | | |
| tgc | cat | gag | aaa | gaa | att | ttg | gag | aag | tac | gga | cat | tca | gac | tgc | tgc | 288 |
| Cys | His | Glu | Lys | Glu | Ile | Leu | Glu | Lys | Tyr | Gly | His | Ser | Asp | Cys | Cys | |
| | | | 85 | | | | | 90 | | | | | 95 | | | |
| agc | caa | agt | gaa | gag | gga | aga | cat | aac | tgt | ttt | ctt | gca | cac | aaa | aag | 336 |
| Ser | Gln | Ser | Glu | Glu | Gly | Arg | His | Asn | Cys | Phe | Leu | Ala | His | Lys | Lys | |
| | | 100 | | | | | 105 | | | | | 110 | | | | |
| ccc | act | cca | gca | tcg | atc | cca | ctt | ttc | caa | gtt | cca | gaa | cct | gtc | aca | 384 |
| Pro | Thr | Pro | Ala | Ser | Ile | Pro | Leu | Phe | Gln | Val | Pro | Glu | Pro | Val | Thr | |
| | 115 | | | | | 120 | | | | | 125 | | | | | |
| agc | tgt | gaa | gca | tat | gaa | gaa | gac | agg | gag | aca | ttc | atg | aac | aaa | ttc | 432 |
| Ser | Cys | Glu | Ala | Tyr | Glu | Glu | Asp | Arg | Glu | Thr | Phe | Met | Asn | Lys | Phe | |
| 130 | | | | | 135 | | | | | 140 | | | | | | |
| att | tat | gag | ata | gca | aga | agg | cat | ccc | ttc | ctg | tat | gca | cct | aca | att | 480 |
| Ile | Tyr | Glu | Ile | Ala | Arg | Arg | His | Pro | Phe | Leu | Tyr | Ala | Pro | Thr | Ile | |
| 145 | | | | 150 | | | | | 155 | | | | | 160 | | |
| ctt | ctt | tgg | gct | gct | cgc | tat | gac | aaa | ata | att | cca | tct | tgc | tgc | aaa | 528 |
| Leu | Leu | Trp | Ala | Ala | Arg | Tyr | Asp | Lys | Ile | Ile | Pro | Ser | Cys | Cys | Lys | |
| | | | 165 | | | | | 170 | | | | | 175 | | | |
| gct | gaa | aat | gca | gtt | gaa | tgc | ttc | caa | aca | aag | gca | gca | aca | gtt | aca | 576 |
| Ala | Glu | Asn | Ala | Val | Glu | Cys | Phe | Gln | Thr | Lys | Ala | Ala | Thr | Val | Thr | |
| | | 180 | | | | | 185 | | | | | 190 | | | | |
| aaa | gaa | tta | aga | gaa | agc | agc | ttg | tta | aat | caa | cat | gca | tgt | gca | gta | 624 |
| Lys | Glu | Leu | Arg | Glu | Ser | Ser | Leu | Leu | Asn | Gln | His | Ala | Cys | Ala | Val | |
| | 195 | | | | | 200 | | | | | 205 | | | | | |
| atg | aaa | aat | ttt | ggg | acc | cga | act | ttc | caa | gcc | ata | act | gtt | act | aaa | 672 |
| Met | Lys | Asn | Phe | Gly | Thr | Arg | Thr | Phe | Gln | Ala | Ile | Thr | Val | Thr | Lys | |
| 210 | | | | | 215 | | | | | 220 | | | | | | |
| ctg | agt | cag | aag | ttt | acc | aaa | gtt | aat | ttt | act | gaa | atc | cag | aaa | cta | 720 |
| Leu | Ser | Gln | Lys | Phe | Thr | Lys | Val | Asn | Phe | Thr | Glu | Ile | Gln | Lys | Leu | |
| 225 | | | | 230 | | | | | 235 | | | | | 240 | | |
| gtc | ctg | gat | gtg | gcc | cat | gta | cat | gag | cac | tgt | tgc | aga | gga | gat | gtg | 768 |
| Val | Leu | Asp | Val | Ala | His | Val | His | Glu | His | Cys | Cys | Arg | Gly | Asp | Val | |
| | | | 245 | | | | | 250 | | | | | 255 | | | |
| ctg | gat | tgt | ctg | cag | gat | ggg | gaa | aaa | atc | atg | tcc | tac | ata | tgt | tct | 816 |
| Leu | Asp | Cys | Leu | Gln | Asp | Gly | Glu | Lys | Ile | Met | Ser | Tyr | Ile | Cys | Ser | |
| | | 260 | | | | | 265 | | | | | 270 | | | | |

-continued

| | |
|---|---|
| caa caa gac act ctg tca aac aaa ata aca gaa tgc tgc aaa ctg acc<br>Gln Gln Asp Thr Leu Ser Asn Lys Ile Thr Glu Cys Cys Lys Leu Thr<br>275                280                   285 | 864 |
| acg ctg gaa cgt ggt caa tgt ata att cat gca gaa aat gat gaa aaa<br>Thr Leu Glu Arg Gly Gln Cys Ile Ile His Ala Glu Asn Asp Glu Lys<br>    290                   295                 300 | 912 |
| cct gaa ggt cta tct cca aat cta aac agg ttt tta gga gat aga gat<br>Pro Glu Gly Leu Ser Pro Asn Leu Asn Arg Phe Leu Gly Asp Arg Asp<br>305                310                 315            320 | 960 |
| ttt aac caa ttt tct tca ggg gaa aaa aat atc ttc ttg gca agt ttt<br>Phe Asn Gln Phe Ser Ser Gly Glu Lys Asn Ile Phe Leu Ala Ser Phe<br>                325                 330            335 | 1008 |
| gtt cat gaa tat tca aga aga cat cct cag ctt gct gtc tca gta att<br>Val His Glu Tyr Ser Arg Arg His Pro Gln Leu Ala Val Ser Val Ile<br>            340                 345            350 | 1056 |
| cta aga gtt gct aaa gga tac cag gag tta ttg gag aag tgt ttc cag<br>Leu Arg Val Ala Lys Gly Tyr Gln Glu Leu Leu Glu Lys Cys Phe Gln<br>                355                 360            365 | 1104 |
| act gaa aac cct ctt gaa tgc caa gat aaa gga gaa gaa gaa tta cag<br>Thr Glu Asn Pro Leu Glu Cys Gln Asp Lys Gly Glu Glu Glu Leu Gln<br>370                375                 380 | 1152 |
| aaa tac atc cag gag agc caa gca ttg gca aag cga agc tgc ggc ctc<br>Lys Tyr Ile Gln Glu Ser Gln Ala Leu Ala Lys Arg Ser Cys Gly Leu<br>385                390                 395            400 | 1200 |
| ttc cag aaa cta gga gaa tat tac tta caa aat gcg ttt ctc gtt gct<br>Phe Gln Lys Leu Gly Glu Tyr Tyr Leu Gln Asn Ala Phe Leu Val Ala<br>                405                 410            415 | 1248 |
| tac aca aag aaa gcc ccc cag ctg acc tcg tcg gag ctg atg gcc atc<br>Tyr Thr Lys Lys Ala Pro Gln Leu Thr Ser Ser Glu Leu Met Ala Ile<br>            420                 425            430 | 1296 |
| acc aga aaa atg gca gcc aca gca gcc act tgt tgc caa ctc agt gag<br>Thr Arg Lys Met Ala Ala Thr Ala Ala Thr Cys Cys Gln Leu Ser Glu<br>                435                 440            445 | 1344 |
| gac aaa cta ttg gcc tgt ggc gag gga gcg gct gac att att atc gga<br>Asp Lys Leu Leu Ala Cys Gly Glu Gly Ala Ala Asp Ile Ile Ile Gly<br>450                455                 460 | 1392 |
| cac tta tgt atc aga cat gaa atg act cca gta aac cct ggt gtt ggc<br>His Leu Cys Ile Arg His Glu Met Thr Pro Val Asn Pro Gly Val Gly<br>465                470                 475            480 | 1440 |
| cag tgc tgc act tct tca tat gcc aac agg agg cca tgc ttc agc agc<br>Gln Cys Cys Thr Ser Ser Tyr Ala Asn Arg Arg Pro Cys Phe Ser Ser<br>                485                 490            495 | 1488 |
| ttg gtg gtg gat gaa aca tat gtc cct cct gca ttc tct gat gac aag<br>Leu Val Val Asp Glu Thr Tyr Val Pro Pro Ala Phe Ser Asp Asp Lys<br>            500                 505            510 | 1536 |
| ttc att ttc cat aag gat ctg tgc caa gct cag ggt gta gcg ctg caa<br>Phe Ile Phe His Lys Asp Leu Cys Gln Ala Gln Gly Val Ala Leu Gln<br>                515                 520            525 | 1584 |
| acg atg aag caa gag ttt ctc att aac ctt gtg aag caa aag cca caa<br>Thr Met Lys Gln Glu Phe Leu Ile Asn Leu Val Lys Gln Lys Pro Gln<br>            530                 535            540 | 1632 |
| ata aca gag gaa caa ctt gag gct gtc att gca gat ttc tca ggc ctg<br>Ile Thr Glu Glu Gln Leu Glu Ala Val Ile Ala Asp Phe Ser Gly Leu<br>545                550                 555            560 | 1680 |
| ttg gag aaa tgc tgc caa ggc cag gaa cag gaa gtc tgc ttt gct gaa<br>Leu Glu Lys Cys Cys Gln Gly Gln Glu Gln Glu Val Cys Phe Ala Glu<br>                565                 570            575 | 1728 |
| gag gga caa aaa ctg att tca aaa act cgt gct gct ttg gga gtt taa<br>Glu Gly Gln Lys Leu Ile Ser Lys Thr Arg Ala Ala Leu Gly Val *<br>            580                 585            590 | 1776 |

```
<210> SEQ ID NO 4
<211> LENGTH: 591
<212> TYPE: PRT
<213> ORGANISM: Homo sapiens

<400> SEQUENCE: 4
```

| | | | | | | | | | | | | | | | |
|---|---|---|---|---|---|---|---|---|---|---|---|---|---|---|---|
| Arg | Thr | Leu | His | Arg | Asn | Glu | Tyr | Gly | Ile | Ala | Ser | Ile | Leu | Asp | Ser |
| 1 | | | | 5 | | | | | 10 | | | | | 15 | |
| Tyr | Gln | Cys | Thr | Ala | Glu | Ile | Ser | Leu | Ala | Asp | Leu | Ala | Thr | Ile | Phe |
| | | | 20 | | | | | 25 | | | | | 30 | | |
| Phe | Ala | Gln | Phe | Val | Gln | Glu | Ala | Thr | Tyr | Lys | Glu | Val | Ser | Lys | Met |
| | | | | 35 | | | | | 40 | | | | | 45 | |
| Val | Lys | Asp | Ala | Leu | Thr | Ala | Ile | Glu | Lys | Pro | Thr | Gly | Asp | Glu | Gln |
| | 50 | | | | | 55 | | | | | 60 | | | | |
| Ser | Ser | Gly | Cys | Leu | Glu | Asn | Gln | Leu | Pro | Ala | Phe | Leu | Glu | Glu | Leu |
| 65 | | | | | 70 | | | | | 75 | | | | | 80 |
| Cys | His | Glu | Lys | Glu | Ile | Leu | Glu | Lys | Tyr | Gly | His | Ser | Asp | Cys | Cys |
| | | | | 85 | | | | | 90 | | | | | 95 | |
| Ser | Gln | Ser | Glu | Glu | Gly | Arg | His | Asn | Cys | Phe | Leu | Ala | His | Lys | Lys |
| | | | 100 | | | | | 105 | | | | | 110 | | |
| Pro | Thr | Pro | Ala | Ser | Ile | Pro | Leu | Phe | Gln | Val | Pro | Glu | Pro | Val | Thr |
| | | | | 115 | | | | | 120 | | | | | 125 | |
| Ser | Cys | Glu | Ala | Tyr | Glu | Glu | Asp | Arg | Glu | Thr | Phe | Met | Asn | Lys | Phe |
| | 130 | | | | | 135 | | | | | 140 | | | | |
| Ile | Tyr | Glu | Ile | Ala | Arg | Arg | His | Pro | Phe | Leu | Tyr | Ala | Pro | Thr | Ile |
| 145 | | | | | 150 | | | | | 155 | | | | | 160 |
| Leu | Leu | Trp | Ala | Ala | Arg | Tyr | Asp | Lys | Ile | Ile | Pro | Ser | Cys | Cys | Lys |
| | | | | 165 | | | | | 170 | | | | | 175 | |
| Ala | Glu | Asn | Ala | Val | Glu | Cys | Phe | Gln | Thr | Lys | Ala | Ala | Thr | Val | Thr |
| | | | 180 | | | | | 185 | | | | | 190 | | |
| Lys | Glu | Leu | Arg | Glu | Ser | Ser | Leu | Leu | Asn | Gln | His | Ala | Cys | Ala | Val |
| | | | | 195 | | | | | 200 | | | | | 205 | |
| Met | Lys | Asn | Phe | Gly | Thr | Arg | Thr | Phe | Gln | Ala | Ile | Thr | Val | Thr | Lys |
| | 210 | | | | | 215 | | | | | 220 | | | | |
| Leu | Ser | Gln | Lys | Phe | Thr | Lys | Val | Asn | Phe | Thr | Glu | Ile | Gln | Lys | Leu |
| 225 | | | | | 230 | | | | | 235 | | | | | 240 |
| Val | Leu | Asp | Val | Ala | His | Val | His | Glu | His | Cys | Cys | Arg | Gly | Asp | Val |
| | | | | 245 | | | | | 250 | | | | | 255 | |
| Leu | Asp | Cys | Leu | Gln | Asp | Gly | Glu | Lys | Ile | Met | Ser | Tyr | Ile | Cys | Ser |
| | | | 260 | | | | | 265 | | | | | 270 | | |
| Gln | Gln | Asp | Thr | Leu | Ser | Asn | Lys | Ile | Thr | Glu | Cys | Cys | Lys | Leu | Thr |
| | | | | 275 | | | | | 280 | | | | | 285 | |
| Thr | Leu | Glu | Arg | Gly | Gln | Cys | Ile | Ile | His | Ala | Glu | Asn | Asp | Glu | Lys |
| | 290 | | | | | 295 | | | | | 300 | | | | |
| Pro | Glu | Gly | Leu | Ser | Pro | Asn | Leu | Asn | Arg | Phe | Leu | Gly | Asp | Arg | Asp |
| 305 | | | | | 310 | | | | | 315 | | | | | 320 |
| Phe | Asn | Gln | Phe | Ser | Ser | Gly | Glu | Lys | Asn | Ile | Phe | Leu | Ala | Ser | Phe |
| | | | | 325 | | | | | 330 | | | | | 335 | |
| Val | His | Glu | Tyr | Ser | Arg | Arg | His | Pro | Gln | Leu | Ala | Val | Ser | Val | Ile |
| | | | 340 | | | | | 345 | | | | | 350 | | |
| Leu | Arg | Val | Ala | Lys | Gly | Tyr | Gln | Glu | Leu | Leu | Glu | Lys | Cys | Phe | Gln |
| | | | | 355 | | | | | 360 | | | | | 365 | |
| Thr | Glu | Asn | Pro | Leu | Glu | Cys | Gln | Asp | Lys | Gly | Glu | Glu | Glu | Leu | Gln |
| | 370 | | | | | 375 | | | | | 380 | | | | |

```
Lys Tyr Ile Gln Glu Ser Gln Ala Leu Ala Lys Arg Ser Cys Gly Leu
385                 390                 395                 400

Phe Gln Lys Leu Gly Glu Tyr Leu Gln Asn Ala Phe Leu Val Ala
            405                 410                 415

Tyr Thr Lys Lys Ala Pro Gln Leu Thr Ser Ser Glu Leu Met Ala Ile
            420                 425                 430

Thr Arg Lys Met Ala Ala Thr Ala Thr Cys Cys Gln Leu Ser Glu
        435                 440                 445

Asp Lys Leu Leu Ala Cys Gly Glu Gly Ala Ala Asp Ile Ile Ile Gly
        450                 455                 460

His Leu Cys Ile Arg His Glu Met Thr Pro Val Asn Pro Gly Val Gly
465                 470                 475                 480

Gln Cys Cys Thr Ser Ser Tyr Ala Asn Arg Arg Pro Cys Phe Ser Ser
                485                 490                 495

Leu Val Val Asp Glu Thr Tyr Val Pro Pro Ala Phe Ser Asp Asp Lys
            500                 505                 510

Phe Ile Phe His Lys Asp Leu Cys Gln Ala Gln Gly Val Ala Leu Gln
            515                 520                 525

Thr Met Lys Gln Glu Phe Leu Ile Asn Leu Val Lys Gln Lys Pro Gln
        530                 535                 540

Ile Thr Glu Glu Gln Leu Glu Ala Val Ile Ala Asp Phe Ser Gly Leu
545                 550                 555                 560

Leu Glu Lys Cys Cys Gln Gly Gln Glu Gln Glu Val Cys Phe Ala Glu
                565                 570                 575

Glu Gly Gln Lys Leu Ile Ser Lys Thr Arg Ala Ala Leu Gly Val
            580                 585                 590

<210> SEQ ID NO 5
<211> LENGTH: 2027
<212> TYPE: DNA
<213> ORGANISM: Homo sapiens
<220> FEATURE:
<221> NAME/KEY: CDS
<222> LOCATION: (45)...(1874)
<220> FEATURE:
<221> NAME/KEY: misc_feature
<222> LOCATION: 797
<223> OTHER INFORMATION: n = A or G

<400> SEQUENCE: 5
atattgtgct tccaccactg ccaataacaa ataactagc aacc atg aag tgg gtg      56
                                              Met Lys Trp Val
                                                1 gaa tca att ttt tta att ttc cta cta aat ttt act gaa tcc aga aca     104
Glu Ser Ile Phe Leu Ile Phe Leu Leu Asn Phe Thr Glu Ser Arg Thr
 5                  10                  15                  20 ctg cat aga aat gaa tat gga ata gct tcc ata ttg gat tct tac caa    152
Leu His Arg Asn Glu Tyr Gly Ile Ala Ser Ile Leu Asp Ser Tyr Gln
                25                  30                  35 tgt act gca gag ata agt tta gct gac ctg gct acc ata ttt ttt gcc    200
Cys Thr Ala Glu Ile Ser Leu Ala Asp Leu Ala Thr Ile Phe Phe Ala
            40                  45                  50 cag ttt gtt caa gaa gcc act tac aag gaa gta agc aaa atg gtg aaa    248
Gln Phe Val Gln Glu Ala Thr Tyr Lys Glu Val Ser Lys Met Val Lys
        55                  60                  65 gat gca ttg act gca att gag aaa ccc act gga gat gaa cag tct tca    296
Asp Ala Leu Thr Ala Ile Glu Lys Pro Thr Gly Asp Glu Gln Ser Ser
    70                  75                  80
```

-continued

| | |
|---|---|
| ggg tgt tta gaa aac cag cta cct gcc ttt ctg gaa gaa ctt tgc cat<br>Gly Cys Leu Glu Asn Gln Leu Pro Ala Phe Leu Glu Glu Leu Cys His<br>85                 90                 95                100 | 344 |
| gag aaa gaa att ttg gag aag tac gga cat tca gac tgc tgc agc caa<br>Glu Lys Glu Ile Leu Glu Lys Tyr Gly His Ser Asp Cys Cys Ser Gln<br>105                110                115 | 392 |
| agt gaa gag gga aga cat aac tgt ttt ctt gca cac aaa aag ccc act<br>Ser Glu Glu Gly Arg His Asn Cys Phe Leu Ala His Lys Lys Pro Thr<br>120                125                130 | 440 |
| cca gca tcg atc cca ctt ttc caa gtt cca gaa cct gtc aca agc tgt<br>Pro Ala Ser Ile Pro Leu Phe Gln Val Pro Glu Pro Val Thr Ser Cys<br>135                140                145 | 488 |
| gaa gca tat gaa gaa gac agg gag aca ttc atg aac aaa ttc att tat<br>Glu Ala Tyr Glu Glu Asp Arg Glu Thr Phe Met Asn Lys Phe Ile Tyr<br>150                155                160 | 536 |
| gag ata gca aga agg cat ccc ttc ctg tat gca cct aca att ctt ctt<br>Glu Ile Ala Arg Arg His Pro Phe Leu Tyr Ala Pro Thr Ile Leu Leu<br>165                170                175                180 | 584 |
| tgg gct gct cgc tat gac aaa ata att cca tct tgc tgc aaa gct gaa<br>Trp Ala Ala Arg Tyr Asp Lys Ile Ile Pro Ser Cys Cys Lys Ala Glu<br>185                190                195 | 632 |
| aat gca gtt gaa tgc ttc caa aca aag gca gca aca gtt aca aaa gaa<br>Asn Ala Val Glu Cys Phe Gln Thr Lys Ala Ala Thr Val Thr Lys Glu<br>200                205                210 | 680 |
| tta aga gaa agc agc ttg tta aat caa cat gca tgt gca gta atg aaa<br>Leu Arg Glu Ser Ser Leu Leu Asn Gln His Ala Cys Ala Val Met Lys<br>215                220                225 | 728 |
| aat ttt ggg acc cga act ttc caa gcc ata act gtt act aaa ctg agt<br>Asn Phe Gly Thr Arg Thr Phe Gln Ala Ile Thr Val Thr Lys Leu Ser<br>230                235                240 | 776 |
| cag aag ttt acc aaa gtt can ttt act gaa atc cag aaa cta gtc ctg<br>Gln Lys Phe Thr Lys Val Xaa Phe Thr Glu Ile Gln Lys Leu Val Leu<br>245                250                255                260 | 824 |
| gat gtg gcc cat gta cat gag cac tgt tgc aga gga gat gtg ctg gat<br>Asp Val Ala His Val His Glu His Cys Cys Arg Gly Asp Val Leu Asp<br>265                270                275 | 872 |
| tgt ctg cag gat ggg gaa aaa atc atg tcc tac ata tgt tct caa caa<br>Cys Leu Gln Asp Gly Glu Lys Ile Met Ser Tyr Ile Cys Ser Gln Gln<br>280                285                290 | 920 |
| gac act ctg tca aac aaa ata aca gaa tgc tgc aaa ctg acc acg ctg<br>Asp Thr Leu Ser Asn Lys Ile Thr Glu Cys Cys Lys Leu Thr Thr Leu<br>295                300                305 | 968 |
| gaa cgt ggt caa tgt ata att cat gca gaa aat gat gaa aaa cct gaa<br>Glu Arg Gly Gln Cys Ile Ile His Ala Glu Asn Asp Glu Lys Pro Glu<br>310                315                320 | 1016 |
| ggt cta tct cca aat cta aac agg ttt tta gga gat aga gat ttt aac<br>Gly Leu Ser Pro Asn Leu Asn Arg Phe Leu Gly Asp Arg Asp Phe Asn<br>325                330                335                340 | 1064 |
| caa ttt tct tca ggg gaa aaa aat atc ttc ttg gca agt ttt gtt cat<br>Gln Phe Ser Ser Gly Glu Lys Asn Ile Phe Leu Ala Ser Phe Val His<br>345                350                355 | 1112 |
| gaa tat tca aga aga cat cct cag ctt gct gtc tca gta att cta aga<br>Glu Tyr Ser Arg Arg His Pro Gln Leu Ala Val Ser Val Ile Leu Arg<br>360                365                370 | 1160 |
| gtt gct aaa gga tac cag gag tta ttg gag aag tgt ttc cag act gaa<br>Val Ala Lys Gly Tyr Gln Glu Leu Leu Glu Lys Cys Phe Gln Thr Glu<br>375                380                385 | 1208 |
| aac cct ctt gaa tgc caa gat aaa gga gaa gaa gaa tta cag aaa tac<br>Asn Pro Leu Glu Cys Gln Asp Lys Gly Glu Glu Glu Leu Gln Lys Tyr<br>390                395                400 | 1256 |

-continued

| | | |
|---|---|---|
| atc cag gag agc caa gca ttg gca aag cga agc tgc ggc ctc ttc cag<br>Ile Gln Glu Ser Gln Ala Leu Ala Lys Arg Ser Cys Gly Leu Phe Gln<br>405                   410                    415                   420 | 1304 |
| aaa cta gga gaa tat tac tta caa aat gcg ttt ctc gtt gct tac aca<br>Lys Leu Gly Glu Tyr Tyr Leu Gln Asn Ala Phe Leu Val Ala Tyr Thr<br>                      425                    430                   435 | 1352 |
| aag aaa gcc ccc cag ctg acc tcg tcg gag ctg atg gcc atc acc aga<br>Lys Lys Ala Pro Gln Leu Thr Ser Ser Glu Leu Met Ala Ile Thr Arg<br>            440                    445                   450 | 1400 |
| aaa atg gca gcc aca gca gcc act tgt tgc caa ctc agt gag gac aaa<br>Lys Met Ala Ala Thr Ala Ala Thr Cys Cys Gln Leu Ser Glu Asp Lys<br>           455                    460                   465 | 1448 |
| cta ttg gcc tgt ggc gag gga gcg gct gac att att atc gga cac tta<br>Leu Leu Ala Cys Gly Glu Gly Ala Ala Asp Ile Ile Ile Gly His Leu<br>470                   475                    480 | 1496 |
| tgt atc aga cat gaa atg act cca gta aac cct ggt gtt ggc cag tgc<br>Cys Ile Arg His Glu Met Thr Pro Val Asn Pro Gly Val Gly Gln Cys<br>485                   490                    495                   500 | 1544 |
| tgc act tct tca tat gcc aac agg agg cca tgc ttc agc agc ttg gtg<br>Cys Thr Ser Ser Tyr Ala Asn Arg Arg Pro Cys Phe Ser Ser Leu Val<br>                      505                    510                   515 | 1592 |
| gtg gat gaa aca tat gtc cct cct gca ttc tct gat gac aag ttc att<br>Val Asp Glu Thr Tyr Val Pro Pro Ala Phe Ser Asp Asp Lys Phe Ile<br>           520                    525                   530 | 1640 |
| ttc cat aag gat ctg tgc caa gct cag ggt gta gcg ctg caa acg atg<br>Phe His Lys Asp Leu Cys Gln Ala Gln Gly Val Ala Leu Gln Thr Met<br>535                   540                    545 | 1688 |
| aag caa gag ttt ctc att aac ctt gtg aag caa aag cca caa ata aca<br>Lys Gln Glu Phe Leu Ile Asn Leu Val Lys Gln Lys Pro Gln Ile Thr<br>           550                    555                   560 | 1736 |
| gag gaa caa ctt gag gct gtc att gca gat ttc tca ggc ctg ttg gag<br>Glu Glu Gln Leu Glu Ala Val Ile Ala Asp Phe Ser Gly Leu Leu Glu<br>565                   570                   575                   580 | 1784 |
| aaa tgc tgc caa ggc cag gaa cag gaa gtc tgc ttt gct gaa gag gga<br>Lys Cys Cys Gln Gly Gln Glu Gln Glu Val Cys Phe Ala Glu Glu Gly<br>                      585                    590                   595 | 1832 |
| caa aaa ctg att tca aaa act cgt gct gct ttg gga gtt taa<br>Gln Lys Leu Ile Ser Lys Thr Arg Ala Ala Leu Gly Val *<br>           600                    605 | 1874 |
| attacttcag gggaagagaa gacaaaacga gtctttcatt cggtgtgaac ttttctcttt | 1934 |
| aattttaact gatttaacac tttttgtgaa ttaatgaaat gataaagact tttatgtgag | 1994 |
| atttccttat cacagaaata aaatatctcc aaa | 2027 |

<210> SEQ ID NO 6
<211> LENGTH: 609
<212> TYPE: PRT
<213> ORGANISM: Homo sapiens
<220> FEATURE:
<221> NAME/KEY: VARIANT
<222> LOCATION: 251
<223> OTHER INFORMATION: Xaa = Any Amino Acid

<400> SEQUENCE: 6

Met Lys Trp Val Glu Ser Ile Phe Leu Ile Phe Leu Leu Asn Phe Thr
1                 5                    10                  15

Glu Ser Arg Thr Leu His Arg Asn Glu Tyr Gly Ile Ala Ser Ile Leu
                 20                    25                   30

Asp Ser Tyr Gln Cys Thr Ala Glu Ile Ser Leu Ala Asp Leu Ala Thr
             35                      40                   45

-continued

```
Ile Phe Phe Ala Gln Phe Val Gln Glu Ala Thr Tyr Lys Glu Val Ser
 50                  55                  60

Lys Met Val Lys Asp Ala Leu Thr Ala Ile Glu Lys Pro Thr Gly Asp
 65                  70                  75                  80

Glu Gln Ser Ser Gly Cys Leu Glu Asn Gln Leu Pro Ala Phe Leu Glu
                 85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
                180                 185                 190

Cys Lys Ala Glu Asn Ala Val Glu Cys Phe Gln Thr Lys Ala Ala Thr
                195                 200                 205

Val Thr Lys Glu Leu Arg Glu Ser Ser Leu Leu Asn Gln His Ala Cys
210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Xaa Phe Thr Glu Ile Gln
                245                 250                 255

Lys Leu Val Leu Asp Val Ala His Val His Glu His Cys Cys Arg Gly
                260                 265                 270

Asp Val Leu Asp Cys Leu Gln Asp Gly Glu Lys Ile Met Ser Tyr Ile
                275                 280                 285

Cys Ser Gln Gln Asp Thr Leu Ser Asn Lys Ile Thr Glu Cys Cys Lys
            290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
            370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Thr Cys Cys Gln Leu
450                 455                 460
```

-continued

```
Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val

<210> SEQ ID NO 7
<211> LENGTH: 1776
<212> TYPE: DNA
<213> ORGANISM: Homo sapiens
<220> FEATURE:
<221> NAME/KEY: CDS
<222> LOCATION: (1)...(1776)
<220> FEATURE:
<221> NAME/KEY: misc_feature
<222> LOCATION: 699
<223> OTHER INFORMATION: n = A or G

<400> SEQUENCE: 7 aga aca ctg cat aga aat gaa tat gga ata gct tcc ata ttg gat tct        48
Arg Thr Leu His Arg Asn Glu Tyr Gly Ile Ala Ser Ile Leu Asp Ser
1               5                   10                  15 tac caa tgt act gca gag ata agt tta gct gac ctg gct acc ata ttt        96
Tyr Gln Cys Thr Ala Glu Ile Ser Leu Ala Asp Leu Ala Thr Ile Phe
                20                  25                  30 ttt gcc cag ttt gtt caa gaa gcc act tac aag gaa gta agc aaa atg       144
Phe Ala Gln Phe Val Gln Glu Ala Thr Tyr Lys Glu Val Ser Lys Met
            35                  40                  45 gtg aaa gat gca ttg act gca att gag aaa ccc act gga gat gaa cag       192
Val Lys Asp Ala Leu Thr Ala Ile Glu Lys Pro Thr Gly Asp Glu Gln
        50                  55                  60 tct tca ggg tgt tta gaa aac cag cta cct gcc ttt ctg gaa gaa ctt       240
Ser Ser Gly Cys Leu Glu Asn Gln Leu Pro Ala Phe Leu Glu Glu Leu
65                  70                  75                  80 tgc cat gag aaa gaa att ttg gag aag tac gga cat tca gac tgc tgc       288
Cys His Glu Lys Glu Ile Leu Glu Lys Tyr Gly His Ser Asp Cys Cys
                85                  90                  95 agc caa agt gaa gag gga aga cat aac tgt ttt ctt gca cac aaa aag       336
Ser Gln Ser Glu Glu Gly Arg His Asn Cys Phe Leu Ala His Lys Lys
            100                 105                 110 ccc act cca gca tcg atc cca ctt ttc caa gtt cca gaa cct gtc aca       384
Pro Thr Pro Ala Ser Ile Pro Leu Phe Gln Val Pro Glu Pro Val Thr
        115                 120                 125 agc tgt gaa gca tat gaa gaa gac agg gag aca ttc atg aac aaa ttc       432
Ser Cys Glu Ala Tyr Glu Glu Asp Arg Glu Thr Phe Met Asn Lys Phe
    130                 135                 140
```

-continued

| | | | | | | | | | | | | | | | | |
|---|---|---|---|---|---|---|---|---|---|---|---|---|---|---|---|---|
| att | tat | gag | ata | gca | aga | agg | cat | ccc | ttc | ctg | tat | gca | cct | aca | att | 480 |
| Ile | Tyr | Glu | Ile | Ala | Arg | Arg | His | Pro | Phe | Leu | Tyr | Ala | Pro | Thr | Ile | |
| 145 | | | | 150 | | | | | 155 | | | | | 160 | | |
| ctt | ctt | tgg | gct | gct | cgc | tat | gac | aaa | ata | att | cca | tct | tgc | tgc | aaa | 528 |
| Leu | Leu | Trp | Ala | Ala | Arg | Tyr | Asp | Lys | Ile | Ile | Pro | Ser | Cys | Cys | Lys | |
| | | | | 165 | | | | | 170 | | | | | 175 | | |
| gct | gaa | aat | gca | gtt | gaa | tgc | ttc | caa | aca | aag | gca | gca | aca | gtt | aca | 576 |
| Ala | Glu | Asn | Ala | Val | Glu | Cys | Phe | Gln | Thr | Lys | Ala | Ala | Thr | Val | Thr | |
| | | 180 | | | | | 185 | | | | | 190 | | | | |
| aaa | gaa | tta | aga | gaa | agc | agc | ttg | tta | aat | caa | cat | gca | tgt | gca | gta | 624 |
| Lys | Glu | Leu | Arg | Glu | Ser | Ser | Leu | Leu | Asn | Gln | His | Ala | Cys | Ala | Val | |
| | | | 195 | | | | | 200 | | | | | 205 | | | |
| atg | aaa | aat | ttt | ggg | acc | cga | act | ttc | caa | gcc | ata | act | gtt | act | aaa | 672 |
| Met | Lys | Asn | Phe | Gly | Thr | Arg | Thr | Phe | Gln | Ala | Ile | Thr | Val | Thr | Lys | |
| | 210 | | | | | 215 | | | | | 220 | | | | | |
| ctg | agt | cag | aag | ttt | acc | aaa | gtt | can | ttt | act | gaa | atc | cag | aaa | cta | 720 |
| Leu | Ser | Gln | Lys | Phe | Thr | Lys | Val | Xaa | Phe | Thr | Glu | Ile | Gln | Lys | Leu | |
| 225 | | | | | 230 | | | | | 235 | | | | | 240 | |
| gtc | ctg | gat | gtg | gcc | cat | gta | cat | gag | cac | tgt | tgc | aga | gga | gat | gtg | 768 |
| Val | Leu | Asp | Val | Ala | His | Val | His | Glu | His | Cys | Cys | Arg | Gly | Asp | Val | |
| | | | | 245 | | | | | 250 | | | | | 255 | | |
| ctg | gat | tgt | ctg | cag | gat | ggg | gaa | aaa | atc | atg | tcc | tac | ata | tgt | tct | 816 |
| Leu | Asp | Cys | Leu | Gln | Asp | Gly | Glu | Lys | Ile | Met | Ser | Tyr | Ile | Cys | Ser | |
| | | 260 | | | | | 265 | | | | | 270 | | | | |
| caa | caa | gac | act | ctg | tca | aac | aaa | ata | aca | gaa | tgc | tgc | aaa | ctg | acc | 864 |
| Gln | Gln | Asp | Thr | Leu | Ser | Asn | Lys | Ile | Thr | Glu | Cys | Cys | Lys | Leu | Thr | |
| | | 275 | | | | | 280 | | | | | 285 | | | | |
| acg | ctg | gaa | cgt | ggt | caa | tgt | ata | att | cat | gca | gaa | aat | gat | gaa | aaa | 912 |
| Thr | Leu | Glu | Arg | Gly | Gln | Cys | Ile | Ile | His | Ala | Glu | Asn | Asp | Glu | Lys | |
| | 290 | | | | | 295 | | | | | 300 | | | | | |
| cct | gaa | ggt | cta | tct | cca | aat | cta | aac | agg | ttt | tta | gga | gat | aga | gat | 960 |
| Pro | Glu | Gly | Leu | Ser | Pro | Asn | Leu | Asn | Arg | Phe | Leu | Gly | Asp | Arg | Asp | |
| 305 | | | | | 310 | | | | | 315 | | | | | 320 | |
| ttt | aac | caa | ttt | tct | tca | ggg | gaa | aaa | aat | atc | ttc | ttg | gca | agt | ttt | 1008 |
| Phe | Asn | Gln | Phe | Ser | Ser | Gly | Glu | Lys | Asn | Ile | Phe | Leu | Ala | Ser | Phe | |
| | | | | 325 | | | | | 330 | | | | | 335 | | |
| gtt | cat | gaa | tat | tca | aga | aga | cat | cct | cag | ctt | gct | gtc | tca | gta | att | 1056 |
| Val | His | Glu | Tyr | Ser | Arg | Arg | His | Pro | Gln | Leu | Ala | Val | Ser | Val | Ile | |
| | | | 340 | | | | | 345 | | | | | 350 | | | |
| cta | aga | gtt | gct | aaa | gga | tac | cag | gag | tta | ttg | gag | aag | tgt | ttc | cag | 1104 |
| Leu | Arg | Val | Ala | Lys | Gly | Tyr | Gln | Glu | Leu | Leu | Glu | Lys | Cys | Phe | Gln | |
| | | 355 | | | | | 360 | | | | | 365 | | | | |
| act | gaa | aac | cct | ctt | gaa | tgc | caa | gat | aaa | gga | gaa | gaa | gaa | tta | cag | 1152 |
| Thr | Glu | Asn | Pro | Leu | Glu | Cys | Gln | Asp | Lys | Gly | Glu | Glu | Glu | Leu | Gln | |
| 370 | | | | | 375 | | | | | 380 | | | | | | |
| aaa | tac | atc | cag | gag | agc | caa | gca | ttg | gca | aag | cga | agc | tgc | ggc | ctc | 1200 |
| Lys | Tyr | Ile | Gln | Glu | Ser | Gln | Ala | Leu | Ala | Lys | Arg | Ser | Cys | Gly | Leu | |
| 385 | | | | | 390 | | | | | 395 | | | | | 400 | |
| ttc | cag | aaa | cta | gga | gaa | tat | tac | tta | caa | aat | gcg | ttt | ctc | gtt | gct | 1248 |
| Phe | Gln | Lys | Leu | Gly | Glu | Tyr | Tyr | Leu | Gln | Asn | Ala | Phe | Leu | Val | Ala | |
| | | | | 405 | | | | | 410 | | | | | 415 | | |
| tac | aca | aag | aaa | gcc | ccc | cag | ctg | acc | tcg | tcg | gag | ctg | atg | gcc | atc | 1296 |
| Tyr | Thr | Lys | Lys | Ala | Pro | Gln | Leu | Thr | Ser | Ser | Glu | Leu | Met | Ala | Ile | |
| | | | 420 | | | | | 425 | | | | | 430 | | | |
| acc | aga | aaa | atg | gca | gcc | aca | gca | gcc | act | tgt | tgc | caa | ctc | agt | gag | 1344 |
| Thr | Arg | Lys | Met | Ala | Ala | Thr | Ala | Ala | Thr | Cys | Cys | Gln | Leu | Ser | Glu | |
| | | | 435 | | | | | 440 | | | | | 445 | | | |
| gac | aaa | cta | ttg | gcc | tgt | ggc | gag | gga | gcg | gct | gac | att | att | atc | gga | 1392 |
| Asp | Lys | Leu | Leu | Ala | Cys | Gly | Glu | Gly | Ala | Ala | Asp | Ile | Ile | Ile | Gly | |
| 450 | | | | | 455 | | | | | 460 | | | | | | |

```
cac tta tgt atc aga cat gaa atg act cca gta aac cct ggt gtt ggc      1440
His Leu Cys Ile Arg His Glu Met Thr Pro Val Asn Pro Gly Val Gly
465                 470                 475                 480 cag tgc tgc act tct tca tat gcc aac agg agg cca tgc ttc agc agc      1488
Gln Cys Cys Thr Ser Ser Tyr Ala Asn Arg Arg Pro Cys Phe Ser Ser
                485                 490                 495 ttg gtg gtg gat gaa aca tat gtc cct cct gca ttc tct gat gac aag      1536
Leu Val Val Asp Glu Thr Tyr Val Pro Pro Ala Phe Ser Asp Asp Lys
            500                 505                 510 ttc att ttc cat aag gat ctg tgc caa gct cag ggt gta gcg ctg caa      1584
Phe Ile Phe His Lys Asp Leu Cys Gln Ala Gln Gly Val Ala Leu Gln
        515                 520                 525 acg atg aag caa gag ttt ctc att aac ctt gtg aag caa aag cca caa      1632
Thr Met Lys Gln Glu Phe Leu Ile Asn Leu Val Lys Gln Lys Pro Gln
    530                 535                 540 ata aca gag gaa caa ctt gag gct gtc att gca gat ttc tca ggc ctg      1680
Ile Thr Glu Glu Gln Leu Glu Ala Val Ile Ala Asp Phe Ser Gly Leu
545                 550                 555                 560 ttg gag aaa tgc tgc caa ggc cag gaa cag gaa gtc tgc ttt gct gaa      1728
Leu Glu Lys Cys Cys Gln Gly Gln Glu Gln Glu Val Cys Phe Ala Glu
                565                 570                 575 gag gga caa aaa ctg att tca aaa act cgt gct gct ttg gga gtt taa      1776
Glu Gly Gln Lys Leu Ile Ser Lys Thr Arg Ala Ala Leu Gly Val *
            580                 585                 590
```

<210> SEQ ID NO 8
<211> LENGTH: 591
<212> TYPE: PRT
<213> ORGANISM: Homo sapiens

<400> SEQUENCE: 8

```
Arg Thr Leu His Arg Asn Glu Tyr Gly Ile Ala Ser Ile Leu Asp Ser
 1               5                  10                  15

Tyr Gln Cys Thr Ala Glu Ile Ser Leu Ala Asp Leu Ala Thr Ile Phe
                20                  25                  30

Phe Ala Gln Phe Val Gln Glu Ala Thr Tyr Lys Glu Val Ser Lys Met
            35                  40                  45

Val Lys Asp Ala Leu Thr Ala Ile Glu Lys Pro Thr Gly Asp Glu Gln
        50                  55                  60

Ser Ser Gly Cys Leu Glu Asn Gln Leu Pro Ala Phe Leu Glu Glu Leu
 65                  70                  75                  80

Cys His Glu Lys Glu Ile Leu Glu Lys Tyr Gly His Ser Asp Cys Cys
                85                  90                  95

Ser Gln Ser Glu Glu Gly Arg His Asn Cys Phe Leu Ala His Lys Lys
            100                 105                 110

Pro Thr Pro Ala Ser Ile Pro Leu Phe Gln Val Pro Glu Pro Val Thr
        115                 120                 125

Ser Cys Glu Ala Tyr Glu Glu Asp Arg Glu Thr Phe Met Asn Lys Phe
    130                 135                 140

Ile Tyr Glu Ile Ala Arg Arg His Pro Phe Leu Tyr Ala Pro Thr Ile
145                 150                 155                 160

Leu Leu Trp Ala Ala Arg Tyr Asp Lys Ile Ile Pro Ser Cys Cys Lys
                165                 170                 175

Ala Glu Asn Ala Val Glu Cys Phe Gln Thr Lys Ala Ala Thr Val Thr
            180                 185                 190

Lys Glu Leu Arg Glu Ser Ser Leu Leu Asn Gln His Ala Cys Ala Val
        195                 200                 205
```

```
Met Lys Asn Phe Gly Thr Arg Thr Phe Gln Ala Ile Thr Val Thr Lys
    210                 215                 220
Leu Ser Gln Lys Phe Thr Lys Val Gln Phe Thr Glu Ile Gln Lys Leu
225                 230                 235                 240
Val Leu Asp Val Ala His Val His Glu His Cys Cys Arg Gly Asp Val
                    245                 250                 255
Leu Asp Cys Leu Gln Asp Gly Glu Lys Ile Met Ser Tyr Ile Cys Ser
            260                 265                 270
Gln Gln Asp Thr Leu Ser Asn Lys Ile Thr Glu Cys Cys Lys Leu Thr
        275                 280                 285
Thr Leu Glu Arg Gly Gln Cys Ile Ile His Ala Glu Asn Asp Glu Lys
290                 295                 300
Pro Glu Gly Leu Ser Pro Asn Leu Asn Arg Phe Leu Gly Asp Arg Asp
305                 310                 315                 320
Phe Asn Gln Phe Ser Ser Gly Glu Lys Asn Ile Phe Leu Ala Ser Phe
                    325                 330                 335
Val His Glu Tyr Ser Arg Arg His Pro Gln Leu Ala Val Ser Val Ile
                340                 345                 350
Leu Arg Val Ala Lys Gly Tyr Gln Glu Leu Leu Glu Lys Cys Phe Gln
            355                 360                 365
Thr Glu Asn Pro Leu Glu Cys Gln Asp Lys Gly Glu Glu Glu Leu Gln
370                 375                 380
Lys Tyr Ile Gln Glu Ser Gln Ala Leu Ala Lys Arg Ser Cys Gly Leu
385                 390                 395                 400
Phe Gln Lys Leu Gly Glu Tyr Tyr Leu Gln Asn Ala Phe Leu Val Ala
                    405                 410                 415
Tyr Thr Lys Lys Ala Pro Gln Leu Thr Ser Ser Glu Leu Met Ala Ile
                420                 425                 430
Thr Arg Lys Met Ala Ala Thr Ala Ala Thr Cys Cys Gln Leu Ser Glu
            435                 440                 445
Asp Lys Leu Leu Ala Cys Gly Glu Gly Ala Ala Asp Ile Ile Ile Gly
450                 455                 460
His Leu Cys Ile Arg His Glu Met Thr Pro Val Asn Pro Gly Val Gly
465                 470                 475                 480
Gln Cys Cys Thr Ser Ser Tyr Ala Asn Arg Arg Pro Cys Phe Ser Ser
                    485                 490                 495
Leu Val Val Asp Glu Thr Tyr Val Pro Pro Ala Phe Ser Asp Asp Lys
                500                 505                 510
Phe Ile Phe His Lys Asp Leu Cys Gln Ala Gln Gly Val Ala Leu Gln
            515                 520                 525
Thr Met Lys Gln Glu Phe Leu Ile Asn Leu Val Lys Gln Lys Pro Gln
530                 535                 540
Ile Thr Glu Glu Gln Leu Glu Ala Val Ile Ala Asp Phe Ser Gly Leu
545                 550                 555                 560
Leu Glu Lys Cys Cys Gln Gly Gln Glu Gln Glu Val Cys Phe Ala Glu
                    565                 570                 575
Glu Gly Gln Lys Leu Ile Ser Lys Thr Arg Ala Ala Leu Gly Val
                580                 585                 590

<210> SEQ ID NO 9
<211> LENGTH: 198
<212> TYPE: PRT
<213> ORGANISM: Homo sapiens
```

```
<400> SEQUENCE: 9

Arg Thr Leu His Arg Asn Glu Tyr Gly Ile Ala Ser Ile Leu Asp Ser
 1               5                  10                  15

Tyr Gln Cys Thr Ala Glu Ile Ser Leu Ala Asp Leu Ala Thr Ile Phe
             20                  25                  30

Phe Ala Gln Phe Val Gln Glu Ala Thr Tyr Lys Glu Val Ser Lys Met
         35                  40                  45

Val Lys Asp Ala Leu Thr Ala Ile Glu Lys Pro Thr Gly Asp Glu Gln
     50                  55                  60

Ser Ser Gly Cys Leu Glu Asn Gln Leu Pro Ala Phe Leu Glu Glu Leu
 65                  70                  75                  80

Cys His Glu Lys Glu Ile Leu Glu Lys Tyr Gly His Ser Asp Cys Cys
                 85                  90                  95

Ser Gln Ser Glu Glu Gly Arg His Asn Cys Phe Leu Ala His Lys Lys
            100                 105                 110

Pro Thr Pro Ala Ser Ile Pro Leu Phe Gln Val Pro Glu Pro Val Thr
        115                 120                 125

Ser Cys Glu Ala Tyr Glu Glu Asp Arg Glu Thr Phe Met Asn Lys Phe
130                 135                 140

Ile Tyr Glu Ile Ala Arg Arg His Pro Phe Leu Tyr Ala Pro Thr Ile
145                 150                 155                 160

Leu Leu Trp Ala Ala Arg Tyr Asp Lys Ile Ile Pro Ser Cys Cys Lys
                165                 170                 175

Ala Glu Asn Ala Val Glu Cys Phe Gln Thr Lys Ala Ala Thr Val Thr
            180                 185                 190

Lys Glu Leu Arg Glu Ser
        195

<210> SEQ ID NO 10
<211> LENGTH: 192
<212> TYPE: PRT
<213> ORGANISM: Homo sapiens

<400> SEQUENCE: 10

Ser Leu Leu Asn Gln His Ala Cys Ala Val Met Lys Asn Phe Gly Thr
 1               5                  10                  15

Arg Thr Phe Gln Ala Ile Thr Val Thr Lys Leu Ser Gln Lys Phe Thr
             20                  25                  30

Lys Val Asn Phe Thr Glu Ile Gln Lys Leu Val Leu Asp Val Ala His
         35                  40                  45

Val His Glu His Cys Cys Arg Gly Asp Val Leu Asp Cys Leu Gln Asp
     50                  55                  60

Gly Glu Lys Ile Met Ser Tyr Ile Cys Ser Gln Gln Asp Thr Leu Ser
 65                  70                  75                  80

Asn Lys Ile Thr Glu Cys Cys Lys Leu Thr Thr Leu Glu Arg Gly Gln
                 85                  90                  95

Cys Ile Ile His Ala Glu Asn Asp Glu Lys Pro Glu Gly Leu Ser Pro
            100                 105                 110

Asn Leu Asn Arg Phe Leu Gly Asp Arg Asp Phe Asn Gln Phe Ser Ser
        115                 120                 125

Gly Glu Lys Asn Ile Phe Leu Ala Ser Phe Val His Glu Tyr Ser Arg
    130                 135                 140

Arg His Pro Gln Leu Ala Val Ser Val Ile Leu Arg Val Ala Lys Gly
145                 150                 155                 160
```

```
Tyr Gln Glu Leu Leu Glu Lys Cys Phe Gln Thr Glu Asn Pro Leu Glu
                165                 170                 175

Cys Gln Asp Lys Gly Glu Glu Leu Gln Lys Tyr Ile Gln Glu Ser
        180                 185                 190
```

<210> SEQ ID NO 11
<211> LENGTH: 201
<212> TYPE: PRT
<213> ORGANISM: Homo sapiens

<400> SEQUENCE: 11

```
Gln Ala Leu Ala Lys Arg Ser Cys Gly Leu Phe Gln Lys Leu Gly Glu
  1               5                  10                  15

Tyr Tyr Leu Gln Asn Glu Phe Leu Val Ala Tyr Thr Lys Lys Ala Pro
                 20                  25                  30

Gln Leu Thr Ser Ser Ala Leu Met Ala Ile Thr Arg Lys Met Ala Ala
             35                  40                  45

Thr Ala Ala Thr Cys Cys Gln Leu Ser Glu Asp Lys Leu Leu Ala Cys
 50                  55                  60

Gly Glu Gly Ala Ala Asp Ile Ile Ile Gly His Leu Cys Ile Arg His
 65                  70                  75                  80

Glu Met Thr Pro Val Asn Pro Gly Val Gly Gln Cys Cys Thr Ser Ser
                 85                  90                  95

Tyr Ala Asn Arg Arg Pro Cys Phe Ser Ser Leu Val Val Asp Glu Thr
                100                 105                 110

Tyr Val Pro Pro Ala Phe Ser Asp Asp Lys Phe Ile Phe His Lys Asp
            115                 120                 125

Leu Cys Gln Ala Gln Gly Val Ala Leu Gln Thr Met Lys Gln Glu Phe
130                 135                 140

Leu Ile Asn Leu Val Lys Gln Lys Pro Gln Ile Thr Glu Glu Gln Leu
145                 150                 155                 160

Glu Ala Val Ile Ala Asp Phe Ser Gly Leu Leu Glu Lys Cys Cys Gln
                165                 170                 175

Gly Gln Glu Gln Glu Val Cys Phe Ala Glu Glu Gly Gln Lys Leu Ile
            180                 185                 190

Ser Lys Thr Arg Ala Ala Leu Gly Val
            195                 200
```

<210> SEQ ID NO 12
<211> LENGTH: 390
<212> TYPE: PRT
<213> ORGANISM: Homo sapiens

<400> SEQUENCE: 12

```
Arg Thr Leu His Arg Asn Glu Tyr Gly Ile Ala Ser Ile Leu Asp Ser
  1               5                  10                  15

Tyr Gln Cys Thr Ala Glu Ile Ser Leu Ala Asp Leu Ala Thr Ile Phe
                 20                  25                  30

Phe Ala Gln Phe Val Gln Glu Ala Thr Tyr Lys Glu Val Ser Lys Met
             35                  40                  45

Val Lys Asp Ala Leu Thr Ala Ile Glu Lys Pro Thr Gly Asp Glu Gln
 50                  55                  60

Ser Ser Gly Cys Leu Glu Asn Gln Leu Pro Ala Phe Leu Glu Glu Leu
 65                  70                  75                  80

Cys His Glu Lys Glu Ile Leu Glu Lys Tyr Gly His Ser Asp Cys Cys
                 85                  90                  95
```

```
Ser Gln Ser Glu Glu Gly Arg His Asn Cys Phe Leu Ala His Lys Lys
            100                 105                 110

Pro Thr Pro Ala Ser Ile Pro Leu Phe Gln Val Pro Glu Pro Val Thr
        115                 120                 125

Ser Cys Glu Ala Tyr Glu Asp Arg Glu Thr Phe Met Asn Lys Phe
130                 135                 140

Ile Tyr Glu Ile Ala Arg Arg His Pro Phe Leu Tyr Ala Pro Thr Ile
145                 150                 155                 160

Leu Leu Trp Ala Ala Arg Tyr Asp Lys Ile Ile Pro Ser Cys Cys Lys
                165                 170                 175

Ala Glu Asn Ala Val Glu Cys Phe Gln Thr Lys Ala Ala Thr Val Thr
            180                 185                 190

Lys Glu Leu Arg Glu Ser Ser Leu Leu Asn Gln His Ala Cys Ala Val
        195                 200                 205

Met Lys Asn Phe Gly Thr Arg Thr Phe Gln Ala Ile Thr Val Thr Lys
    210                 215                 220

Leu Ser Gln Lys Phe Thr Lys Val Asn Phe Thr Glu Ile Gln Lys Leu
225                 230                 235                 240

Val Leu Asp Val Ala His Val His Glu His Cys Cys Arg Gly Asp Val
                245                 250                 255

Leu Asp Cys Leu Gln Asp Gly Glu Lys Ile Met Ser Tyr Ile Cys Ser
            260                 265                 270

Gln Gln Asp Thr Leu Ser Asn Lys Ile Thr Glu Cys Cys Lys Leu Thr
        275                 280                 285

Thr Leu Glu Arg Gly Gln Cys Ile Ile His Ala Glu Asn Asp Glu Lys
    290                 295                 300

Pro Glu Gly Leu Ser Pro Asn Leu Asn Arg Phe Leu Gly Asp Arg Asp
305                 310                 315                 320

Phe Asn Gln Phe Ser Ser Gly Glu Lys Asn Ile Phe Leu Ala Ser Phe
                325                 330                 335

Val His Glu Tyr Ser Arg Arg His Pro Gln Leu Ala Val Ser Val Ile
            340                 345                 350

Leu Arg Val Ala Lys Gly Tyr Gln Glu Leu Leu Glu Lys Cys Phe Gln
        355                 360                 365

Thr Glu Asn Pro Leu Glu Cys Gln Asp Lys Gly Glu Glu Glu Leu Gln
    370                 375                 380

Lys Tyr Ile Gln Glu Ser
385                 390

<210> SEQ ID NO 13
<211> LENGTH: 393
<212> TYPE: PRT
<213> ORGANISM: Homo sapiens

<400> SEQUENCE: 13

Ser Leu Leu Asn Gln His Ala Cys Ala Val Met Lys Asn Phe Gly Thr
1               5                   10                  15

Arg Thr Phe Gln Ala Ile Thr Val Thr Lys Leu Ser Gln Lys Phe Thr
                20                  25                  30

Lys Val Asn Phe Thr Glu Ile Gln Lys Leu Val Leu Asp Val Ala His
            35                  40                  45

Val His Glu His Cys Cys Arg Gly Asp Val Leu Asp Cys Leu Gln Asp
        50                  55                  60

Gly Glu Lys Ile Met Ser Tyr Ile Cys Ser Gln Gln Asp Thr Leu Ser
65                  70                  75                  80
```

-continued

```
Asn Lys Ile Thr Glu Cys Cys Lys Leu Thr Thr Leu Glu Arg Gly Gln
                85                  90                  95
Cys Ile Ile His Ala Glu Asn Asp Glu Lys Pro Glu Gly Leu Ser Pro
            100                 105                 110
Asn Leu Asn Arg Phe Leu Gly Asp Arg Asp Phe Asn Gln Phe Ser Ser
        115                 120                 125
Gly Glu Lys Asn Ile Phe Leu Ala Ser Phe Val His Glu Tyr Ser Arg
    130                 135                 140
Arg His Pro Gln Leu Ala Val Ser Val Ile Leu Arg Val Ala Lys Gly
145                 150                 155                 160
Tyr Gln Glu Leu Leu Glu Lys Cys Phe Gln Thr Glu Asn Pro Leu Glu
                165                 170                 175
Cys Gln Asp Lys Gly Glu Glu Leu Gln Lys Tyr Ile Gln Glu Ser
            180                 185                 190
Gln Ala Leu Ala Lys Arg Ser Cys Gly Leu Phe Gln Lys Leu Gly Glu
        195                 200                 205
Tyr Tyr Leu Gln Asn Glu Phe Leu Val Ala Tyr Thr Lys Lys Ala Pro
    210                 215                 220
Gln Leu Thr Ser Ser Ala Leu Met Ala Ile Thr Arg Lys Met Ala Ala
225                 230                 235                 240
Thr Ala Ala Thr Cys Cys Gln Leu Ser Glu Asp Lys Leu Leu Ala Cys
                245                 250                 255
Gly Glu Gly Ala Ala Asp Ile Ile Gly His Leu Cys Ile Arg His
            260                 265                 270
Glu Met Thr Pro Val Asn Pro Gly Val Gly Gln Cys Cys Thr Ser Ser
        275                 280                 285
Tyr Ala Asn Arg Arg Pro Cys Phe Ser Ser Leu Val Val Asp Glu Thr
    290                 295                 300
Tyr Val Pro Pro Ala Phe Ser Asp Asp Lys Phe Ile Phe His Lys Asp
305                 310                 315                 320
Leu Cys Gln Ala Gln Gly Val Ala Leu Gln Thr Met Lys Gln Glu Phe
                325                 330                 335
Leu Ile Asn Leu Val Lys Gln Lys Pro Gln Ile Thr Glu Glu Gln Leu
            340                 345                 350
Glu Ala Val Ile Ala Asp Phe Ser Gly Leu Leu Glu Lys Cys Cys Gln
        355                 360                 365
Gly Gln Glu Gln Glu Val Cys Phe Ala Glu Glu Gly Gln Lys Leu Ile
    370                 375                 380
Ser Lys Thr Arg Ala Ala Leu Gly Val
385                 390

<210> SEQ ID NO 14
<211> LENGTH: 325
<212> TYPE: PRT
<213> ORGANISM: Homo sapiens

<400> SEQUENCE: 14

Met Ser Tyr Ile Cys Ser Gln Gln Asp Thr Leu Ser Asn Lys Ile Thr
  1               5                  10                  15
Glu Cys Cys Lys Leu Thr Thr Leu Glu Arg Gly Gln Cys Ile Ile His
                20                  25                  30
Ala Glu Asn Asp Glu Lys Pro Glu Gly Leu Ser Pro Asn Leu Asn Arg
            35                  40                  45
Phe Leu Gly Asp Arg Asp Phe Asn Gln Phe Ser Ser Gly Glu Lys Asn
        50                  55                  60
```

```
Ile Phe Leu Ala Ser Phe Val His Glu Tyr Ser Arg Arg His Pro Gln
 65                  70                  75                  80

Leu Ala Val Ser Val Ile Leu Arg Val Ala Lys Gly Tyr Gln Glu Leu
                 85                  90                  95

Leu Glu Lys Cys Phe Gln Thr Glu Asn Pro Leu Glu Cys Gln Asp Lys
            100                 105                 110

Gly Glu Glu Glu Leu Gln Lys Tyr Ile Gln Glu Ser Gln Ala Leu Ala
        115                 120                 125

Lys Arg Ser Cys Gly Leu Phe Gln Lys Leu Gly Glu Tyr Tyr Leu Gln
    130                 135                 140

Asn Glu Phe Leu Val Ala Tyr Thr Lys Lys Ala Pro Gln Leu Thr Ser
145                 150                 155                 160

Ser Ala Leu Met Ala Ile Thr Arg Lys Met Ala Ala Thr Ala Ala Thr
                165                 170                 175

Cys Cys Gln Leu Ser Glu Asp Lys Leu Leu Ala Cys Gly Glu Gly Ala
            180                 185                 190

Ala Asp Ile Ile Ile Gly His Leu Cys Ile Arg His Glu Met Thr Pro
        195                 200                 205

Val Asn Pro Gly Val Gly Gln Cys Cys Thr Ser Ser Tyr Ala Asn Arg
    210                 215                 220

Arg Pro Cys Phe Ser Ser Leu Val Val Asp Glu Thr Tyr Val Pro Pro
225                 230                 235                 240

Ala Phe Ser Asp Asp Lys Phe Ile Phe His Lys Asp Leu Cys Gln Ala
                245                 250                 255

Gln Gly Val Ala Leu Gln Thr Met Lys Gln Glu Phe Leu Ile Asn Leu
            260                 265                 270

Val Lys Gln Lys Pro Gln Ile Thr Glu Glu Gln Leu Glu Ala Val Ile
    275                 280                 285

Ala Asp Phe Ser Gly Leu Leu Glu Lys Cys Cys Gln Gly Gln Glu Gln
        290                 295                 300

Glu Val Cys Phe Ala Glu Gly Gln Lys Leu Ile Ser Lys Thr Arg
305                 310                 315                 320

Ala Ala Leu Gly Val
                325

<210> SEQ ID NO 15
<211> LENGTH: 192
<212> TYPE: PRT
<213> ORGANISM: Homo sapiens

<400> SEQUENCE: 15

Ser Leu Leu Asn Gln His Ala Cys Ala Val Met Lys Asn Phe Gly Thr
 1               5                  10                  15

Arg Thr Phe Gln Ala Ile Thr Val Thr Lys Leu Ser Gln Lys Phe Thr
                20                  25                  30

Lys Val Gln Phe Thr Glu Ile Gln Lys Leu Val Leu Asp Val Ala His
            35                  40                  45

Val His Glu His Cys Cys Arg Gly Asp Val Leu Asp Cys Leu Gln Asp
    50                  55                  60

Gly Glu Lys Ile Met Ser Tyr Ile Cys Ser Gln Gln Asp Thr Leu Ser
 65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
            100                 105                 110
```

-continued

Asn Leu Asn Arg Phe Leu Gly Asp Arg Asp Phe Asn Gln Phe Ser Ser
            115                 120                 125

Gly Glu Lys Asn Ile Phe Leu Ala Ser Phe Val His Glu Tyr Ser Arg
130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Leu Gln Lys Tyr Ile Gln Glu Ser
                180                 185                 190

<210> SEQ ID NO 16
<211> LENGTH: 390
<212> TYPE: PRT
<213> ORGANISM: Homo sapiens

<400> SEQUENCE: 16

Arg Thr Leu His Arg Asn Glu Tyr Gly Ile Ala Ser Ile Leu Asp Ser
1               5                   10                  15

Tyr Gln Cys Thr Ala Glu Ile Ser Leu Ala Asp Leu Ala Thr Ile Phe
                20                  25                  30

Phe Ala Gln Phe Val Gln Glu Ala Thr Tyr Lys Glu Val Ser Lys Met
            35                  40                  45

Val Lys Asp Ala Leu Thr Ala Ile Glu Lys Pro Thr Gly Asp Glu Gln
        50                  55                  60

Ser Ser Gly Cys Leu Glu Asn Gln Leu Pro Ala Phe Leu Glu Glu Leu
65                  70                  75                  80

Cys His Glu Lys Glu Ile Leu Glu Lys Tyr Gly His Ser Asp Cys Cys
                85                  90                  95

Ser Gln Ser Glu Glu Gly Arg His Asn Cys Phe Leu Ala His Lys Lys
                100                 105                 110

Pro Thr Pro Ala Ser Ile Pro Leu Phe Gln Val Pro Glu Pro Val Thr
            115                 120                 125

Ser Cys Glu Ala Tyr Glu Glu Asp Arg Glu Thr Phe Met Asn Lys Phe
130                 135                 140

Ile Tyr Glu Ile Ala Arg Arg His Pro Phe Leu Tyr Ala Pro Thr Ile
145                 150                 155                 160

Leu Leu Trp Ala Ala Arg Tyr Asp Lys Ile Ile Pro Ser Cys Cys Lys
                165                 170                 175

Ala Glu Asn Ala Val Glu Cys Phe Gln Thr Lys Ala Ala Thr Val Thr
                180                 185                 190

Lys Glu Leu Arg Glu Ser Ser Leu Leu Asn Gln His Ala Cys Ala Val
                195                 200                 205

Met Lys Asn Phe Gly Thr Arg Thr Phe Gln Ala Ile Thr Val Thr Lys
210                 215                 220

Leu Ser Gln Lys Phe Thr Lys Val Gln Phe Thr Glu Ile Gln Lys Leu
225                 230                 235                 240

Val Leu Asp Val Ala His Val His Glu His Cys Cys Arg Gly Asp Val
                245                 250                 255

Leu Asp Cys Leu Gln Asp Gly Glu Lys Ile Met Ser Tyr Ile Cys Ser
                260                 265                 270

Gln Gln Asp Thr Leu Ser Asn Lys Ile Thr Glu Cys Cys Lys Leu Thr
                275                 280                 285

Thr Leu Glu Arg Gly Gln Cys Ile Ile His Ala Glu Asn Asp Glu Lys
290                 295                 300

```
Pro Glu Gly Leu Ser Pro Asn Leu Asn Arg Phe Leu Gly Asp Arg Asp
305                 310                 315                 320

Phe Asn Gln Phe Ser Ser Gly Glu Lys Asn Ile Phe Leu Ala Ser Phe
            325                 330                 335

Val His Glu Tyr Ser Arg Arg His Pro Gln Leu Ala Val Ser Val Ile
            340                 345                 350

Leu Arg Val Ala Lys Gly Tyr Gln Glu Leu Leu Glu Lys Cys Phe Gln
            355                 360                 365

Thr Glu Asn Pro Leu Glu Cys Gln Asp Lys Gly Glu Glu Leu Gln
            370                 375                 380

Lys Tyr Ile Gln Glu Ser
385                 390

<210> SEQ ID NO 17
<211> LENGTH: 393
<212> TYPE: PRT
<213> ORGANISM: Homo sapiens

<400> SEQUENCE: 17

Ser Leu Leu Asn Gln His Ala Cys Ala Val Met Lys Asn Phe Gly Thr
 1               5                  10                  15

Arg Thr Phe Gln Ala Ile Thr Val Thr Lys Leu Ser Gln Lys Phe Thr
                20                  25                  30

Lys Val Gln Phe Thr Glu Ile Gln Lys Leu Val Leu Asp Val Ala His
            35                  40                  45

Val His Glu His Cys Cys Arg Gly Asp Val Leu Asp Cys Leu Gln Asp
 50                  55                  60

Gly Glu Lys Ile Met Ser Tyr Ile Cys Ser Gln Gln Asp Thr Leu Ser
65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
            100                 105                 110

Asn Leu Asn Arg Phe Leu Gly Asp Arg Asp Phe Asn Gln Phe Ser Ser
            115                 120                 125

Gly Glu Lys Asn Ile Phe Leu Ala Ser Phe Val His Glu Tyr Ser Arg
130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Glu Leu Gln Lys Tyr Ile Gln Glu Ser
            180                 185                 190

Gln Ala Leu Ala Lys Arg Ser Cys Gly Leu Phe Gln Lys Leu Gly Glu
        195                 200                 205

Tyr Tyr Leu Gln Asn Ala Phe Leu Val Ala Tyr Thr Lys Lys Ala Pro
210                 215                 220

Gln Leu Thr Ser Ser Glu Leu Met Ala Ile Thr Arg Lys Met Ala Ala
225                 230                 235                 240

Thr Ala Ala Thr Cys Cys Gln Leu Ser Glu Asp Lys Leu Leu Ala Cys
                245                 250                 255

Gly Glu Gly Ala Ala Asp Ile Ile Ile Gly His Leu Cys Ile Arg His
            260                 265                 270

Glu Met Thr Pro Val Asn Pro Gly Val Gly Gln Cys Cys Thr Ser Ser
            275                 280                 285
```

```
Tyr Ala Asn Arg Arg Pro Cys Phe Ser Ser Leu Val Val Asp Glu Thr
290                 295                 300

Tyr Val Pro Pro Ala Phe Ser Asp Asp Lys Phe Ile Phe His Lys Asp
305                 310                 315                 320

Leu Cys Gln Ala Gln Gly Val Ala Leu Gln Thr Met Lys Gln Glu Phe
            325                 330                 335

Leu Ile Asn Leu Val Lys Gln Lys Pro Gln Ile Thr Glu Glu Gln Leu
            340                 345                 350

Glu Ala Val Ile Ala Asp Phe Ser Gly Leu Leu Glu Lys Cys Cys Gln
            355                 360                 365

Gly Gln Glu Gln Glu Val Cys Phe Ala Glu Glu Gly Gln Lys Leu Ile
370                 375                 380

Ser Lys Thr Arg Ala Ala Leu Gly Val
385                 390
```

<210> SEQ ID NO 18
<211> LENGTH: 30
<212> TYPE: DNA
<213> ORGANISM: Artificial Sequence
<220> FEATURE:
<223> OTHER INFORMATION: Synthetic

<400> SEQUENCE: 18
atgaagtggg tggaatcaat tttttttaatt         30

<210> SEQ ID NO 19
<211> LENGTH: 28
<212> TYPE: DNA
<213> ORGANISM: Artificial Sequence
<220> FEATURE:
<223> OTHER INFORMATION: Synthetic

<400> SEQUENCE: 19
attcatttat gagatagcaa gaaggcat           28

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
aaaaaatcat gtcctacata tgttctcaa          29

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
aaactcgaga agtgggtgga a                  21

<210> SEQ ID NO 22
<211> LENGTH: 24
<212> TYPE: DNA
<213> ORGANISM: Artificial Sequence
<220> FEATURE:
<223> OTHER INFORMATION: Synthetic -continued

```
<400> SEQUENCE: 22
aaactcgagt taaactccca aagc                                                  24

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
gattgacaag taatacgctg tttcctc                                               27

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
tttgtaaacc tcttgtaaag ttacaag                                               27

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
ccaggcacag tctctagtct a                                                     21

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
ggacaggacc aagtacaggc t                                                     21
```